(12) United States Patent
Helmer et al.

(10) Patent No.: US 12,233,247 B2
(45) Date of Patent: *Feb. 25, 2025

(54) INJECTION DEVICE

(71) Applicant: Sanofi-Aventis Deutschland GMBH, Frankfurt am Main (DE)

(72) Inventors: Michael Helmer, Frankfurt am Main (DE); Michael Schabbach, Frankfurt am Main (DE); Julian Kersting, Rüsselsheim (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/449,981

(22) Filed: Aug. 15, 2023

(65) Prior Publication Data

US 2023/0381421 A1 Nov. 30, 2023

Related U.S. Application Data

(63) Continuation of application No. 16/761,212, filed as application No. PCT/EP2018/080078 on Nov. 5, 2018, now Pat. No. 11,759,575.

(30) Foreign Application Priority Data

Nov. 7, 2017 (EP) ..................................... 17200314

(51) Int. Cl.
*A61M 5/315* (2006.01)
(52) U.S. Cl.
CPC ...... *A61M 5/31553* (2013.01); *A61M 5/3156* (2013.01); *A61M 5/31563* (2013.01); *A61M 5/31585* (2013.01)

(58) Field of Classification Search
CPC ............ A61M 5/31553; A61M 5/3156; A61M 5/31563; A61M 5/31585; A61M 5/31568
See application file for complete search history.

(56) References Cited

U.S. PATENT DOCUMENTS

| 5,637,094 A | 6/1997 | Stewart, Jr. et al. |
| 2008/0071227 A1 | 3/2008 | Moser et al. |
| (Continued) | | |

FOREIGN PATENT DOCUMENTS

| CN | 103189086 | 7/2013 |
| CN | 105102031 | 11/2015 |
| (Continued) | | |

OTHER PUBLICATIONS

International Preliminary Report on Patentability in Application No. PCT/EP2018/080078, dated May 12, 2020, 6 pages.
(Continued)

*Primary Examiner* — Dung T Ulsh
(74) *Attorney, Agent, or Firm* — Fish & Richardson P.C.

(57) ABSTRACT

An injection device includes an elongated housing extending along a longitudinal axis, a piston rod to operably engage with a piston of a cartridge filled with the medicament, a dose tracker selectively operably engageable with the piston rod, wherein the dose tracker is longitudinally displaceable relative to the housing from an initial position in a proximal direction towards at least a first activation position for setting of the dose and wherein the dose tracker is longitudinally displaceable relative to the housing in a distal direction from the at least first activation position towards the initial position for dispensing of the dose, a spring to urge the dose tracker in the proximal direction relative to the housing, an interlock to lock the dose tracker in the initial position relative to the housing, and a release member to release the interlock.

15 Claims, 17 Drawing Sheets

(56) References Cited

U.S. PATENT DOCUMENTS

| | | | |
|---|---|---|---|
| 2008/0097322 A1* | 4/2008 | Markussen | A61M 5/31585 604/135 |
| 2009/0247960 A1* | 10/2009 | Kohlbrenner | A61M 5/20 604/232 |
| 2013/0218098 A1 | 8/2013 | Chung | |
| 2016/0022921 A1 | 1/2016 | Chuvashova | |
| 2016/0045668 A1* | 2/2016 | Mayer | A61M 5/31583 604/207 |
| 2020/0261656 A1 | 8/2020 | Helmer et al. | |

FOREIGN PATENT DOCUMENTS

| | | |
|---|---|---|
| CN | 105102032 | 11/2015 |
| CN | 105307711 | 2/2016 |
| CN | 107206183 | 9/2017 |
| JP | 2013-506448 | 2/2013 |
| JP | 2013-527004 | 6/2013 |
| JP | 2014-500750 | 1/2014 |
| WO | WO 2004/078239 | 9/2004 |
| WO | WO 2004/078240 | 9/2004 |
| WO | WO 2004/078241 | 9/2004 |
| WO | WO 2011/039209 | 4/2011 |
| WO | WO 2011/152772 | 12/2011 |
| WO | WO 2012/067582 | 5/2012 |
| WO | WO 2014/166907 | 10/2014 |
| WO | WO 2014/166908 | 10/2014 |
| WO | WO 2014/173434 | 10/2014 |
| WO | WO 2016/128207 | 8/2016 |
| WO | WO 2016/142501 | 9/2016 |

OTHER PUBLICATIONS

International Search Report and Written Opinion in Application No. PCT/EP2018/080078, dated Dec. 6, 2018, 8 pages.

Third Party Observations in International Application No. PCT/EP2018/080078, dated Oct. 9, 2019, 18 pages.

* cited by examiner

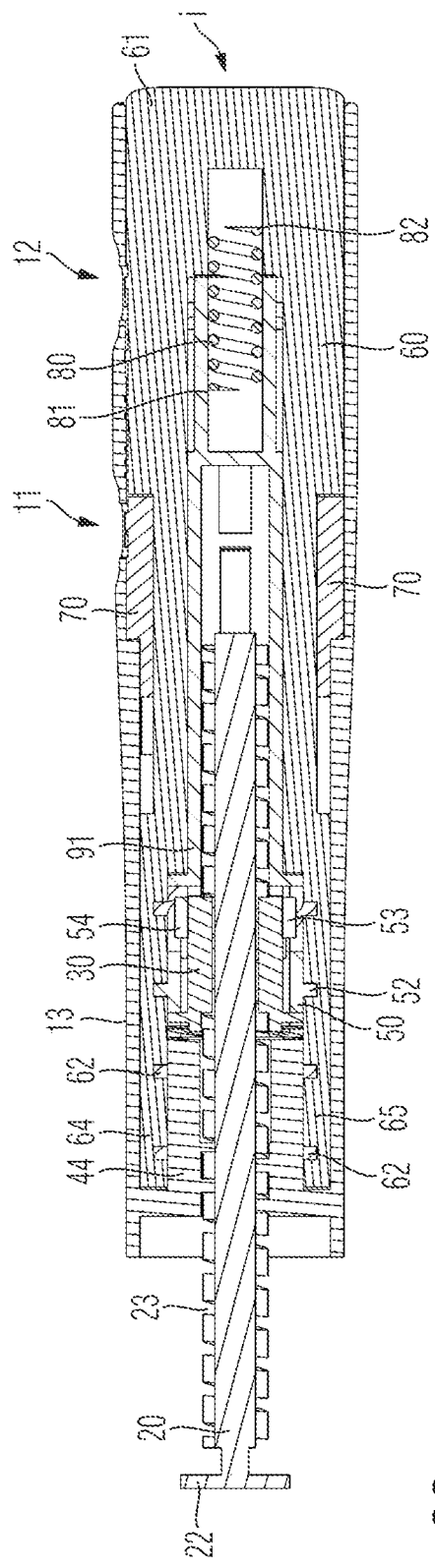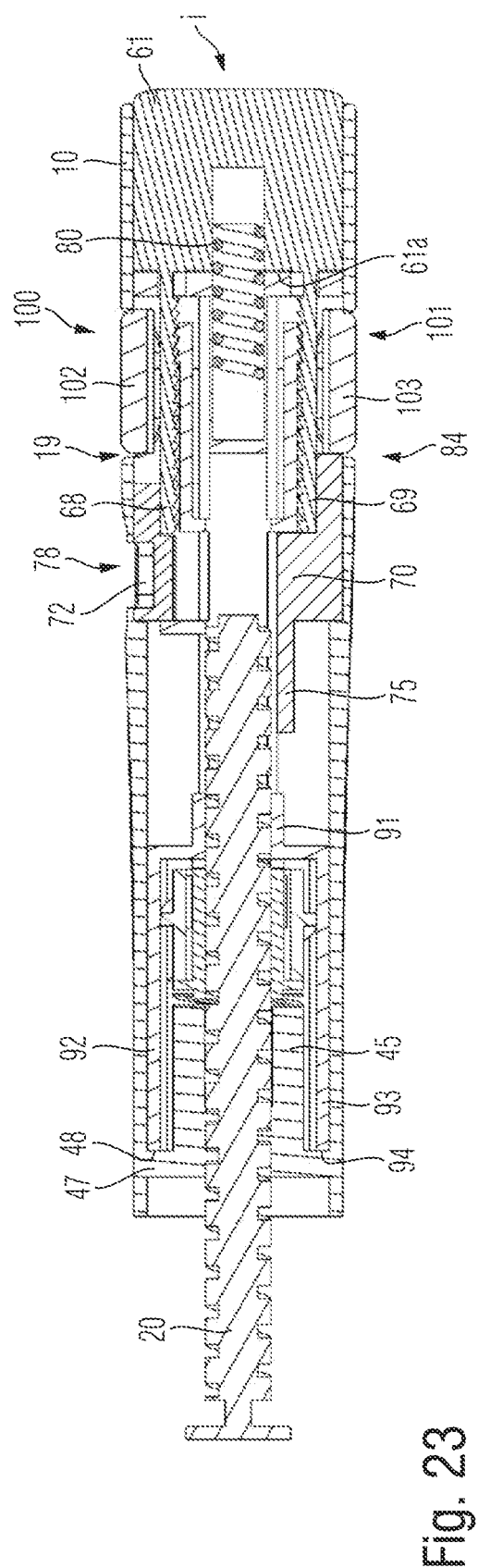

INJECTION DEVICE

CROSS REFERENCE TO RELATED APPLICATIONS

The present application is a continuation of U.S. application Ser. No. 16/761,212, filed May 1, 2020, which is the national stage entry of International Patent Application No. PCT/EP2018/080078, filed on Nov. 5, 2018, and claims priority to Application No. EP 17200314.7, filed on Nov. 7, 2017, the disclosures of which are incorporated herein by reference.

TECHNICAL FIELD

The present disclosure relates in one aspect to an injection device, such as a pen-type injector for setting and dispensing of a dose of a medicament. In particular, the disclosure relates to an injection device with a longitudinally displaceable dose tracker longitudinally displaceable relative to a housing of the device during setting and dispensing of the dose. In a further aspect the disclosure relates to a mechanically implemented injection device that provides an automated dose setting in accordance to a preselected size of a dose.

BACKGROUND

Injection devices for setting and dispensing a single or multiple doses of a liquid medicament are as such well-known in the art. Generally, such devices have substantially a similar purpose as that of an ordinary syringe.

Injection devices, in particular pen-type injectors have to meet a number of user-specific requirements. For instance, with patient's suffering chronic diseases, such as diabetes, the patient may be physically infirm and may also have impaired vision. Suitable injection devices especially intended for home medication therefore need to be robust in construction and should be easy to use. Furthermore, manipulation and general handling of the device and its components should be intelligible and easy understandable. Moreover, the dose setting as well as dose dispensing procedure must be easy to operate and has to be unambiguous.

Typically, such devices comprise a housing including a particular cartridge holder, adapted to receive a cartridge at least partially filled with the medicament to be dispensed. Such devices further comprise a drive mechanism, usually having a displaceable piston rod which is adapted to operably engage with a piston of the cartridge. By means of the drive mechanism and its piston rod, the piston of the cartridge is displaceable in a distal direction or in a dispensing direction and may therefore expel a predefined amount of the medicament via a piercing assembly, which is to be releasably coupled with a distal end section of the housing of the injection device.

The medicament to be dispensed by the injection device is provided and contained in a multi-dose cartridge. Such cartridges typically comprise a vitreous barrel sealed in a distal direction by means of a pierceable seal and being further sealed in proximal direction by the piston. With reusable injection devices an empty cartridge is replaceable by a new one. In contrast, injection devices of disposable type are to be discarded when the medicament in the cartridge has been dispensed or used-up.

For some applications it can be advantageous to limit a maximum size of a dose that can be dispensed or expelled from the cartridge. This may help to prevent unintended overdosing of the medicament could.

SUMMARY

The present disclosure relates to an injection device that offers an increased patient safety and which comprises a mechanism that prevents unintended overdosing or underdosing of a medicament. The injection device may provide a limited capability to set and to dispense doses of different sizes. The injection device may at least temporally provide setting and dispensing of only one or a few differently sized doses. In particular, the injection device may be configured to allow and to enable repeated and multiple setting and dispensing of only a few, e.g. of two, three or four differently sized doses of the medicament.

The injection device may be intuitive and simple to use even for patients suffering side effects or having an impaired vision. The injection device may provide a clearly visible feedback and/or mechanical or haptic feedback to a user thereby indicating that a dose of a predefined size is set and that the device is ready for initiating a dispensing procedure.

The injection device may also provide a rather automated dose setting procedure in accordance to a predefined or preselected dose of the medicament.

In one aspect there is provided an injection device for setting and for injecting or dispensing of a dose of a medicament. The injection device comprises an elongated housing extending along a longitudinal axis. The housing comprises a distal end and a proximal end. The distal end is closest to a dispensing end of the device whereas the proximal end is located at an opposite end of the elongated housing. The injection device further comprises a piston rod to operably engage with a piston of a cartridge filled with the medicament. The cartridge typically comprises a barrel, such as a vitreous and tubular shaped barrel filled with a liquid medicament. A distal end of the cartridge is sealed, e.g. by a pierceable seal, such as a septum. Towards a proximal end, the cartridge is sealed by a piston slidably displaceable along the longitudinal direction of the cartridge. The piston is displaceable along the longitudinal axis or along an axial direction by means of the piston rod which is configured to be advanced in distal direction by a drive mechanism of the injection device. In this way a predefined amount of the medicament can be expelled from the cartridge.

The injection device further comprises a dose tracker that is selectively operably engageable with the piston rod. The dose tracker is longitudinally displaceable relative to the housing from an initial position in a proximal direction towards at least a first activation position during detting of the dose and/or for setting of the dose. For dispensing or for injecting of the dose the dose tracker is displaceable in the opposite direction. Hence, the dose tracker is longitudinally displaceable relative to the housing in the distal direction from the at least first activation position towards the initial position for dispensing of the dose.

The injection device further comprises a spring to urge the dose tracker in the proximal direction relative to the housing. In this way an automated dose setting can be provided. By means of the spring the dose tracker can be automatically displaced from the initial position towards and into the at least first activation position. The injection device further comprises an interlock to lock the dose tracker in the initial position relative to the housing. By means of the interlock the dose tracker can be immobilized relative to the housing at least with regard to the longitudinal or axial direction. It can be fixed to the housing by means of the interlock to prevent unintended dose setting and/or dose dispensing.

The injection device further comprises at least one release member configured to release the interlock. Typically, the release member is operably engaged with the interlock or is a component of the interlock. The release member may comprise a trigger or an actuation member that can be actuated, i.e. depressed or dialed by a user in order to initiate an automated dose setting procedure. By means of the mutual interaction of the spring, the interlock and the at least one release member the process of dose setting can be facilitated. For setting of a dose a user only has to actuate or to depress the at least one release member so as to release the interlock. With a released interlock the dose tracker is released with regard to a longitudinal displacement. It is then free to be moved under the action of the relaxing spring. Typically, the spring comprises a first end connected to or in abutment with the dose tracker. The spring further comprises a second end connected to or in abutment with the housing of the injection device. In this way the dose tracker is displaceable from the initial position towards the proximal direction under the effect of the spring. For and during dispensing of a dose the dose tracker is displaceable or depressible, e.g. by a thumb of a user against the action of the spring. Hence, during dose dispensing mechanical energy can be stored in the spring, which energy can be released for a subsequent dose setting procedure.

According to a further example the injection device comprises at least a first tracking stop feature provided on one of the dose tracker and the housing. The tracking stop feature is configured to lock and/or to block a longitudinal displacement of the dose tracker relative to the housing when reaching the at least first activation position. The at least one tracking stop feature may be configured to mechanically engage with the housing or with a component rigidly connected to the housing when the dose tracker reaches the at least first activation position. With examples wherein the first tracking stop feature is provided on the housing the tracking stop feature is configured to mechanically engage with the dose tracker or with a component rigidly connected or coupled to the dose tracker, such as a preselector.

By means of the at least one tracking stop feature the at least first activation position of the dose tracker and hence the longitudinal or axial position of the dose tracker relative to the housing can be defined.

Typically, the at least one tracking stop feature is configured to axially abut with the housing of the injection device or with a component fixed to the housing of the injection device. In this way a proximally directed displacement of the dose tracker can be limited and the dose tracker can be fixed in at least a first well-defined activation position.

In a further example the injection device comprises a preselector comprising at least a first preselector stop feature to engage with the at least first tracking stop feature. The preselector is at least one of translationally and rotationally displaceable relative to the housing between at least two preselection positional states. The preselector stop feature is configured to mechanically engage with the at least first tracking stop feature in order to block and to impede a displacement of the dose tracker beyond a predefined activation position. The preselector stop feature is configured to block a proximally directed displacement of the dose tracker when engaged with the tracking stop feature or when in abutment with the tracking stop feature.

In examples, where the at least first tracking stop feature is provided on the housing of the injection device the preselector may be axially or longitudinally engaged with the dose tracker. It is then that the at least first preselector stop feature engages the at least first tracking stop feature when the preselector connected to or engaged with the dose tracker reaches the at least first activation position.

The preselector defines a maximum length of a displacement path of the dose tracker relative to the housing during a dose setting procedure. The length of this displacement path correlates to the size of the dose actually set and to be dispensed during a subsequent dispensing operation of the injection device. During setting of the dose and also during dispensing of the dose the preselector is stationary relative to the housing. It may be fixed or locked to the housing.

Since the preselector is at least one of translationally or rotationally displaceable relative to the housing the position of the at least first preselector stop feature relative to the at least one tracking stop feature of the dose tracker can be varied. In this way the displacement path for the dose tracker from the initial position to the at least first activation position can be varied. By moving the preselector relative to the housing preselected doses of different size can be defined.

When the preselector is translationally displaceable relative to the housing between at least two preselection positional states the length of a longitudinal displacement path of the dose tracker can be changed respectively. If the preselector is rotationally displaceable relative to the housing it may comprise not only a first preselector stop feature but also a second and/or a third preselector stop feature. The first, second or third preselector stop features may be provided at different positions with regards to the longitudinal axis of the housing. By rotating the preselector relative to the housing only one of a plurality of preselector stop features, e.g. a first preselector stop feature can be aligned with the tracking stop feature of the dose tracker, thereby defining e.g. a first displacement path for the dose tracker of a first specific length.

When rotating the preselector relative to the housing in another positional or rotational state another preselector stop feature, e.g. a second preselector stop feature will be aligned with the tracking stop feature, thereby defining a second displacement path for the dose tracker. The length of the second displacement path differs from the length of the first displacement path, because the longitudinal position of the first preselector stop feature differs from the longitudinal position of the second preselector stop feature. In this way doses of different sizes can be set by rotating the preselector from one positional state to another positional state.

According to a further example the preselector is lockable to the housing in any of the at least two preselection positional states. For this there may be provided a first locking feature provided on the preselector and a second locking feature provided on the housing. The first and the second locking features may be configured to positively engage. For instance, the first locking feature may comprise a catch or detent structure and the second locking feature may comprise a catch or a counter detent structure. One of the detent structure and the counter detent structure may comprise a protrusion whereas the other one of the detent structure and the counter detent structure comprises numerous recesses to receive and to lock the protrusion. The recesses are spaced from each other with regards to a displacement direction of the preselector relative to the housing. If the preselector is rotationally displaceable relative to the housing the recesses are spaced apart from each other along the circumference of a sidewall of the housing. If the preselector is longitudinally displaceable relative to the housing the recesses will be spaced apart from each other along the longitudinal direction. The recesses may be spaced equidistantly.

Typically, the preselector is accessible to a user from outside the injection device. The preselector may flush with an outside surface of the housing. The preselector or a portion thereof may protrude from an outside surface of the housing. Alternatively, the preselector may be arranged in a recess of the outside surface of the housing. Eventually and for impeding unauthorized access to the preselector the preselector may be covered by a protector, such as an adhesive label or the like cover. The preselector may be configured to become displaced only by means of a specific tool. In this way unauthorized displacement or manipulation of the preselector can be prevented. Access to the preselector may be provided only to trained medical staff or caregivers.

In a further example the preselector is rotationally supported on or in at least one of the housing and the dose tracker. The preselector comprises at least a second preselector stop feature being at least one of tangentially and longitudinally offset from the first preselector stop feature. Alternatively, at least one of the dose tracker and the housing comprises at least a second tracking stop feature being at least one of tangentially and longitudinally offset from the first tracking stop feature.

There may be examples with only one tracking stop feature provided on the dose tracker or on the housing. With such examples the preselector comprises at least a first and a second preselector stop feature one of which being configured to engage with the tracking stop feature in accordance to the positional state of the preselector. In other examples there may be provided only one preselector stop feature. With such examples the at least one of the dose tracker and the housing comprises at least a first and a second tracking stop feature one of which being configured to engage with the preselector stop feature in accordance to the positional state of the preselector.

The preselector comprises at least a second preselector stop feature that is at least one of tangentially and longitudinally offset from the first preselector stop feature. Depending on the preselection positional state, hence depending on the rotational state or orientation of the preselector relative to the housing only one of the first and the second preselector stop features is in longitudinal alignment with the tracking stop feature of the dose tracker. When the interlock is released by the at least one release member the dose tracker is displaced towards the proximal direction under the action of the spring until the tracking stop feature of the dose tracker engages with one of the first or second preselector stop features when arriving at a first activation position or at a second activation position of the dose tracker. Here, it may be sufficient, when there is provided only a single tracking stop feature.

As an alternative, at least one of the dose tracker and the housing comprises at least a first and a second tracking stop feature being at least one of tangentially and longitudinally offset from the first tracking stop feature. Also here and depending on the preselection positional state, hence depending on the rotational state or orientation of the preselector relative to the housing, only one of the first and the second tracking stop features is in longitudinal alignment with the preselector stop feature. When the interlock is released by the at least one release member, the dose tracker is displaced towards the proximal direction under the action of the spring until that particular tracking stop feature which is in alignment with the preselector stop feature engages with the respective preselector stop feature when arriving at a respective activation position that is defined by the preselection positional state of the preselector. Here, it may be sufficient, when there is provided only a single preselector stop feature.

Since one of the preselector, the dose tracker and the housing comprises at least a first and a second preselector stop feature or at least a first and a second tracking stop feature that are located at a predefined longitudinal or tangential distance from each other, and which distance extends nonparallel to a direction along which the preselector is displaceable relative to the housing, there can be provided a variety of well-defined stop position for the dose tracker with regard to the housing each defining a dose of the medicament of different size.

According to another example the at least first preselector stop feature comprises a stop face to abut with a stop face of the tracking stop feature. Typically, the stop faces of the preselector stop feature and the tracking stop feature are axial or tangential stop faces. Typically, the stop face or stop faces of the preselector or of the preselector stop feature face towards the distal direction whereas the axial stop face or axial stop faces of the tracking stop feature face towards the proximal direction. When the dose tracker is displaced under the action of the spring towards the proximal direction the stop face of the tracking stop feature gets in axial and/or or tangential abutment with the stop face of the first preselector stop feature or with any other stop face of any further of the second or third preselector stop features. When the preselector is axially fixed to the housing any further proximally directed displacement of the dose tracker relative to the housing is effectively prevented.

It is further conceivable, that the preselector stop feature not only comprises a single stop face but several stop faces configured to simultaneously abut with numerous correspondingly shaped stop faces of the dose tracker or of the tracking stop feature. In this way an improved abutment, e.g. axial abutment or tangential abutment, between the preselector and the dose tracker can be provided. Mechanical forces and mechanical momentum can be transferred between the dose tracker and the housing rather reliable and failure safe.

The stop face of the preselector may be regarded as a first stop face of the preselector. The stop face of the tracking stop feature may be regarded as a first stop face of the tracking stop feature.

According to another example the at least second preselector stop feature comprises a second stop face that is longitudinally and/or tangentially offset from the first stop face. In this way, the second stop face of the preselector is longitudinally and/or tangentially offset from the first stop face of the preselector. For instance, the first stop face may be located proximally from the second stop face. The first stop face may define a maximum size of a dose to be set and dispensed with the injection device. If the first axial stop face is aligned with the tracking stop feature the dose tracker can be subject to a maximum longitudinal displacement relative to the housing during a dose setting procedure. If the second stop face of the preselector is aligned with the tracking stop feature the axial displacement of the dose tracker will be shorter during a dose setting procedure.

When the second stop face of the preselector is aligned with the tracking stop feature the dose tracker will be displaceable towards and into a second activation position relative to the housing. With the first stop face of the preselector aligned with the tracking stop feature, the dose tracker will reach the first activation position at the end of the dose setting procedure. Here, the first activation position of the dose tracker may be located proximally offset from the second activation position.

With other examples the tracking stop feature may comprise a first and a second stop face, wherein the second stop face is longitudinally and/or tangentially offset from the first stop face. For instance, the first stop face may be located distally from the second stop face. When the first stop face is in alignment with a correspondingly shaped stop face of the preselector it may define a maximum size of a dose to be set and dispensed with the injection device. The dose tracker can then be subject to a maximum longitudinal displacement relative to the housing during a dose setting procedure.

In another example one of the at least first tracking stop feature and the at least first preselector stop feature comprises a first radial protrusion and the other one of the at least first tracking stop feature and the preselector stop feature comprises at least one of: a) a second radial protrusion to abut with the first radial protrusion and b) a groove configured to slidably receive the first radial protrusion.

Here, the first tracking stop feature may comprise a radially outwardly extending protrusion to engage with a radially inwardly extending protrusion of the preselector stop feature. The first tracking stop feature may comprise at least one radially outwardly extending protrusion to slidably engage with a longitudinally or helically shaped groove of the preselector stop feature. In another example, the preselector stop feature comprises at least one radially inwardly extending protrusion to engage with a radially outwardly extending protrusion of the tracking stop feature. In other examples, the preselector stop feature comprises a radially inwardly extending protrusion slidably engaged with a longitudinally or helically shaped groove on an outside surface of the dose tracker.

In further examples the preselector stop feature comprises a radially inwardly extending protrusion slidably engaged with at least one longitudinally shaped or helically shaped groove of the tracking stop feature provided on the housing. Alternatively, the tracking stop feature of the housing comprises a radial protrusion slidably engaged with at least one longitudinally shaped or helically shaped groove of the preselector stop feature.

In another example the tracking stop feature comprises a radial protrusion protruding from a sidewall of the dose tracker. Typically, the radial protrusion may protrude from an outside facing surface of the tracking member configured as a tracking sleeve. The radial protrusion of the tracking stop feature may comprise a radially outwardly extending protrusion when the tracking stop feature is provided on the dose tracker. When provided on the housing the radial protrusion of the tracking stop feature may comprise a radially inwardly extending protrusion. Generally, the radial protrusion may comprise a pin or a flange.

According to another example the preselector stop feature comprises a radial protrusion protruding from a sidewall of the preselector. The preselector may also comprise a sleeve-like shape. The preselector stop feature may comprise a radially inwardly extending protrusion to engage with a radially outwardly extending protrusion of the tracking stop feature. Alternatively, the radial protrusion of the preselector stop feature may comprise a radially outwardly extending protrusion to engage with a radially inwardly extending protrusion of the tracking stop feature.

This applies in particular where the tracking stop feature is provided on the housing of the injection device. The radial protrusion of the preselector stop feature may comprise a pin or a flange. Typically, the at least one radial protrusion of the tracking stop feature and the at least one radial protrusion of the preselector stop feature are correspondingly or complementary shaped. They are arranged on a particular portion or section of the dose tracker or housing and the preselector such that upon reaching the maximum dose positional state the radial protrusions of the tracking stop feature and the preselector stop feature get in direct mechanical abutment thereby impeding any further displacement of the dose tracker relative to the housing in a dose incrementing direction.

According to another example one of the housing and the dose tracker comprises a first tracking stop feature and a second tracking stop feature. The first and the second tracking stop features each comprise a groove. Hence, the first tracking stop feature comprises a first groove and the second tracking stop feature comprises a second groove. Both grooves are configured to slidably receive the radial protrusion of the preselector. The first and the second grooves may extend parallel to each other but comprise different elongations. At an end of the first groove there is provided the first stop face. At an end of the second groove there is provided the second stop face. The first and the second stop faces are both configured to engage with the stop face of the radial protrusion.

The radial protrusion of the preselector stop feature slides along only one of the first groove and the second groove of the housing or the dose tracker. When the preselector is in a first of the two preselection positional state the radial protrusion slides along the first groove. When the preselector is in a second of the at least two preselection positional states the radial protrusion slides along the second groove.

The first and the second grooves comprise different shapes. In this way, the first and the second grooves enable and provide different relative displacement paths between the preselector and the dose tracker or the housing. Likewise, the differently shaped grooves provide different displacement path length of the dose tracker between the initial position or the zero dose positional state and the at least first activation position or the maximum dose positional state relative to the preselector or relative to the housing, respectively.

Alternatively, it may be the preselector that comprises a first preselector stop feature and a second preselector stop feature. The first preselector stop feature comprises a first groove and the second preselector stop feature comprises a second groove. Both grooves are configured to slidably receive the radial protrusion of the tracking stop feature, which is provided on the dose tracker or on the housing. The first and the second grooves may extend parallel to each other but comprise different elongations. At an end of the first groove there is provided the first stop face. At an end of the second groove there is provided the second stop face. The first and the second stop faces are both configured to engage with the stop face of the radial protrusion.

In a further example the first groove extends parallel to the second groove. The second groove is longer than the first groove. The first groove and the second groove merge into a connecting groove. The connecting groove extends along a direction that is substantially parallel to that direction along which the preselector is displaceable between the first preselection positional state and the second preselection positional state. While in the zero dose positional state the protrusion of the tracking stop feature may be located in the connecting groove. A displacement of the preselector along the elongation of the connecting groove leads to a sliding motion of the protrusion along the connecting groove.

When reaching one of the at least two preselection positional states the protrusion is still in the connecting groove but is also aligned with one of the first groove and the second groove. When the preselector is in the first preselection positional state the protrusion is aligned with the first groove. When the preselector is arranged in the second preselection positional state the protrusion is aligned with the second groove. As soon a dose setting procedure is started the protrusion slides along the first groove or along the second groove depending on the preselection positional state of the preselector.

The first stop face and/or the second stop face of the respective first and second grooves are located at an end of the groove facing away from the connecting groove. Since the first and second grooves are of different length they provide different displacement paths for the radial protrusion sliding along the respective groove. In this way differently sized maximum dose positional states of the dose tracker can be provided. Once the radial protrusion reaches an end of a respective groove facing away from the connecting groove any further displacement of the dose tracker relative to the housing is effectively impeded.

According to another example the preselector comprises a preselector sleeve. The preselector sleeve may be arranged at a proximal end of the housing. The preselector sleeve may be provided between a proximal portion of the dose tracker and a proximal end of the housing. The preselector may be located directly on or may be supported by the housing at a predefined distance from the proximal end of the housing. Here, the preselector may be located and arranged at a predefined distal offset from the proximal end of the housing.

In another example the preselector may be translationally fixed to the dose tracker but may be freely rotatable relative to the dose tracker. Here, the preselector may be in keyed engagement or may be splined to the housing, e.g. by way of one of the first and second grooves of the preselector stop feature engaged with the tracking stop feature.

Generally and in some examples the preselector is arrestable or fixable to the sidewall of the housing in at least two different discrete positions denoted as preselection positional states. The preselection positional states may be equidistantly arranged on the sidewall. A distance between neighboring preselection positional states is identical and corresponds to the longitudinal advancing motion of the dose tracker as the dose tracker may undergo a complete revolution relative to the housing. In this way it is provided, that the tracking stop feature always engages with the preselector stop feature when reaching the maximum dose positional state.

According to a further example the injection device further comprises a trigger integrally formed or longitudinally engaged with least one of the trigger and a proximal end of the dose tracker and protruding from a proximal end of the housing when in the at least first activation position. The trigger may comprise a dose button and may be integrally formed with the dose tracker. Also in any other activation position the dose button may protrude from the proximal end of the housing. In the initial position the dose button may be arranged substantially flush with the proximal end of the housing. By activating the release member and by deactivating the interlock the spring is configured to displace the dose tracker in proximal direction so that the trigger protrudes from the proximal end of the housing. For a subsequent dose dispensing or dose injection procedure the trigger or dose button is then depressible in distal direction.

The force typically provided by a user and acting on the dose tracker in distal direction is used for both, namely for advancing the piston rod in distal direction for expelling the medicament and for the biasing or tensioning the spring.

The longitudinal displacement of the dose tracker from the initial position towards the at least first activation position and hence a longitudinal distance between the initial position and the at least first activation position may directly correlate with the size of the dose to be dispensed or injected by the injection device. The larger the distance between the initial position and the at least first activation position the larger will be the size of the dose.

It is conceivable, that the dose tracker is displaceable from the initial position towards and into a multitude of different discrete activation positions. Hence, the dose tracker might be displaceable and fixable in the first activation position but also in a second or optionally in a third or in a fourth activation position. In the second, third or fourth activation positions the dose tracker is located in a stepwise increasing distance from the initial position. The second, third and fourth activation positions may be equidistantly separated along the longitudinal axis of the elongated housing. However, the distances between the first, the second, the third and the fourth activation positions may be of different sizes and may be determined by an individual configuration of the respective injection device.

In another example the spring has a first end operably connected to the housing and has a second end operably connected to the dose tracker. The first end may be connected to a further component of the injection device, which further component is at least one of rotationally or translationally locked to the housing or is in a torque proof engagement with the housing. In the same way also the second end of the spring may either be directly connected to the dose tracker or it may be connected to a component of the injection device that is at least one of translationally or rotationally locked to the dose tracker. The spring may serve and provide a mechanical drive for automatically displacing the dose tracker at least from the initial position to the at least first activation position.

The spring comprises a cylindrically shaped compression spring or a helically wound torsion spring. The spring encloses at least a portion of the dose tracker or the spring is arranged inside a hollow portion of the dose tracker. When implemented as a torsion spring the spring is configured to induce a torque to the dose tracker relative to the housing. A torsion spring is of particular benefit where the dose tracker is rotationally supported on the housing or wherein the dose tracker is threadedly engaged with the housing. The spring provides a long-lasting, durable and failure safe mechanical drive to apply a driving force to the dose tracker during a dose setting procedure.

During a dose dispensing procedure the dose tracker member returns from the at least first activation position and hence from a maximum dose positional state to the initial position that coincides with a zero dose positional state. This displacement is typically conducted manually by a force exerted and provided by a user of the device. The displacement of the dose tracker from the maximum dose positional state to the zero dose positional state is to be conducted against the action of the spring element.

In this way mechanical energy exerted to and provided to the dose tracker during dispensing of a dose is at least partially stored in the spring element. For a subsequent dose setting procedure this mechanical energy may be released again. Insofar the injection device is configured for repeated use and hence for setting and dispensing of a multitude of doses of the medicament.

In another example the dose tracker comprises a tracking sleeve that is threadedly engaged with the housing. The tracking sleeve may be cylindrically shaped. The tracking sleeve may be located inside the housing. When threadedly engaged with the housing the first end of the spring may be directly connected to the dose tracker whereas the second end of the spring may be directly connected to the housing. In this way and when released by actuation of the release member the dose tracker is free to rotate or to wound helically relative to the housing under the action of the spring.

In this way a fully automated dose setting procedure can be provided by the injection device. The end user does no longer have to take care about the dose setting process. He may only actuate the release member for that the dose setting mechanism automatically displaces the dose tracker into the at least first activation position. Selection or modification of the dose to be set is exclusively conducted by the preselector. The preselector remains fixed and stationary relative to the housing during dose setting as well as during dose dispensing. For setting and dispensing numerous doses of equal size the preselector may remain stationary relative to the housing. At least the preselector remains stationary with regard to a displacement direction along which the preselector has to be displaced for bringing the preselector from one preselection positional state to another preselection positional state. User interaction with the injection device may be limited to an actuation of the release member for setting of the dose and to the application of a driving force to a trigger or the like actuator of the injection device in order to trigger or to control a dose dispensing procedure.

According to another example the release member comprises an annular ring rotationally supported at the proximal end of the housing. One of an inside surface of the annular ring and an outside surface of the dose tracker comprises at least one catch element to engage with a protrusion on one of the other of the inside surface of the annular ring and the outside surface of the dose tracker. For releasing the dose tracker from the housing the annular ring is intended to be rotated along a tangential or circumferential direction of the housing. In this way the at least one catch element disengages from the at least one protrusion thereby liberating a displacement of the dose tracker relative to the housing.

The release member may be rotatable against the action of a spring. In this way and after rotating the release member from a locking position into a release position the spring serves to return the release member into the locking position. The catch element may comprise a beveled section to engage with the protrusion. As the dose tracker returns into the initial position at the end of the dose dispensing procedure the protrusion may slide along the catch element thereby inducing a rotation of the release member against the action of the spring. As the initial position is reached, the catch element may return into a locking configuration under the action of the spring.

With a further example the at least one release member of the injection device comprises a release button that is located in a recess of a sidewall of the housing. The release button is depressible into the housing for releasing the dose tracker. The release button may be arranged substantially flush with an outer surface of the sidewall of the housing. In this way unintentional depression of the release button can be effectively prevented. The injection device may even comprise not only one but two release members that are located at diametrically opposite portions in or on the sidewall of the housing. The housing of the injection device may be of tubular shape. Providing a first and a second release button on opposite sides of the housing further increases patient safety. The interlock is only released when both release members are actuated, e.g. depressed simultaneously. With this example depressing of only one release member will be insufficient to release the interlock. In this way misuse of the device and an unintentional depression of only one release button has no effect on the injection device and its operation.

For operating the injection device it may be only necessary to depress the at least one release button. Under the effect of the spring the dose tracker will then advance and protrude from a proximal end of the housing. The injection device is then ready for dispensing of a dose. Upon depressing of the dose tracker or the trigger a predefined size of the dose of the medicament will be dispensed and injected. When returning into the initial position the interlock is configured to automatically re-activate in order to lock the dose tracker in the initial position. For a subsequent dose setting and dispensing procedure the at least one release button has to be depressed again and the dose tracker will protrude from the housing in a manner substantially identical as described before. The user does not have to take care about the size of the dose. Once the size of a dose is defined by a respective positional state of the preselector the injection device is configured to set and to dispense always the same amount of the medicament.

In some examples the preselector may be concealed to the patient. Moreover, special tools may be necessary to modify the preselection positional state of the preselector. Authorized persons, such as healthcare professionals may have exclusive access to the preselector. Before the injection device is handed out to a patient for self-medication the healthcare professional may define a single dose size exclusively to be dispensed with the injection device. In this way the patient himself does not have to take care about the correct size of a dose to be set and dispensed. A danger of underdosing or overdosing can be reduced and patient safety can be thus increased.

According to a further example the interlock comprises a first engaging structure connected to or integral with the dose tracker and a second engaging structure connected to or integral with the at least one release member. Typically, the first and the second engaging structures are configured to positively engage with regard to the longitudinal direction when the at least one release member is in an initial position and when the dose tracker is in the initial position. The first and the second engaging structures are configured to disengage when the at least one release member is actuated, e.g. depressed. The first and second engaging structures may comprise mutually correspondingly shaped toothed sections or radial protrusions and/or recesses that are configured to transfer an axial force between the dose tracker and the housing. The first and second engaging structures may comprise mutually corresponding detent structures or snap features. Typically, the second engaging structure is displaceable in radial direction so as to disengage from the first engaging structure. In this way the first engaging structure and hence the dose tracker can be released and can be displaced towards the proximal direction under the effect of the spring.

In another example the injection device further comprises a cartridge. The cartridge comprises a barrel filled with the medicament. The barrel is sealed by a bung or piston that is axially displaceable relative to the barrel by means of the piston rod. For and during a dispensing operation the piston rod is operably engageable with the bung of the cartridge in order to displace the bung in a distal direction. Typically, a distal end of the cartridge is sealed by a pierceable membrane, such as a septum. For dispensing of the medicament the pierceable seal can be penetrated by a double-tipped injection needle. A distally directed displacement of the bung induced by a correspondingly advancing piston rod therefore leads to the expelling of the dose of the medicament.

In the present context the term 'distal' or 'distal end' relates to an end of the injection device that faces towards an injection site of a person or of an animal. The term 'proximal' or 'proximal end' relates to an opposite end of the injection device, which is furthest away from an injection site of a person or of an animal.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(02)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4 (1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(02)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2) 25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present invention without departing from the spirit and scope of the invention as defined in the appended claims. Further, it is to be noted, that any reference numerals used in the appended claims are not to be construed as limiting the scope of the invention.

BRIEF DESCRIPTION OF THE FIGURES

In the following, embodiments of the injection device are described in detail by making reference to the drawings, in which:

FIG. 22 is a longitudinal cross-section through the injection device and FIG. 23 is a longitudinal cross-section of the injection device when rotated by 90° compared to the cross-section of FIG. 22.

DETAILED DESCRIPTION

Figure 1:
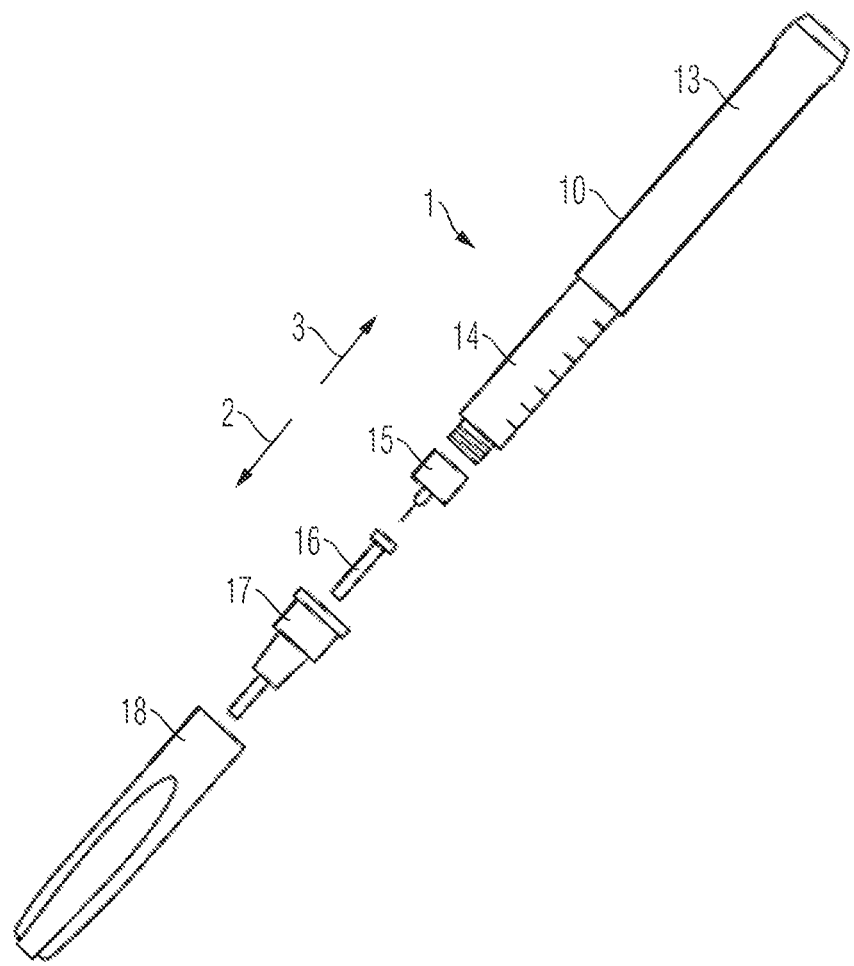
FIG. 1 shows a schematic illustration of a pen-type injection device.

The injection device 1 as shown in FIG. 1 comprises a housing 10 of tubular and elongated shape. The injection device 1 may be configured as a prefilled disposable injection device. Alternatively, it may be configured as a reusable injection device.

The injection device 1 comprises a distal end to which a needle assembly 15 can be affixed. An injection needle of the needle assembly 15 can be protected by an inner needle cap 16 and further by an outer needle cap 17. The distal end of the injection device 1 is further covered by a protective cap 18 that is releasably engageable with the housing 10 of the injection device 1. When attached to the injection device 1 the protective cap 18 covers a portion of the housing of the injection device 1 that is also denoted as a cartridge holder 14. The cartridge holder 14 is configured to accommodate a cartridge 6 filled with a medicament. The cartridge 6 comprises a tubular-shaped barrel 25. The barrel 25 is sealed in distal direction 2 by means of a pierceable seal 26.

Towards the proximal direction 3 the barrel 6 is sealed by a displaceable piston 7. The piston 7 is displaceable in distal direction 2 by means of a piston rod 20 of a drive mechanism 8 of the injection device 1 expelling a predefined amount of the medicament from the cartridge and through the injection needle of the needle assembly 15. The pierceable seal 26 is configured as a septum and is pierceable by a proximally directed tipped end of the needle assembly 15. Furthermore, the cartridge holder 14 comprises a threaded socket 28 at its distal end to threadedly engage with a correspondingly threaded portion of the needle assembly 15. By attaching the needle assembly 15 to the distal end of the cartridge holder 14 the seal 26 of the cartridge 6 is penetrated thereby establishing a fluid transferring access to the interior of the cartridge 6.

Figure 4:
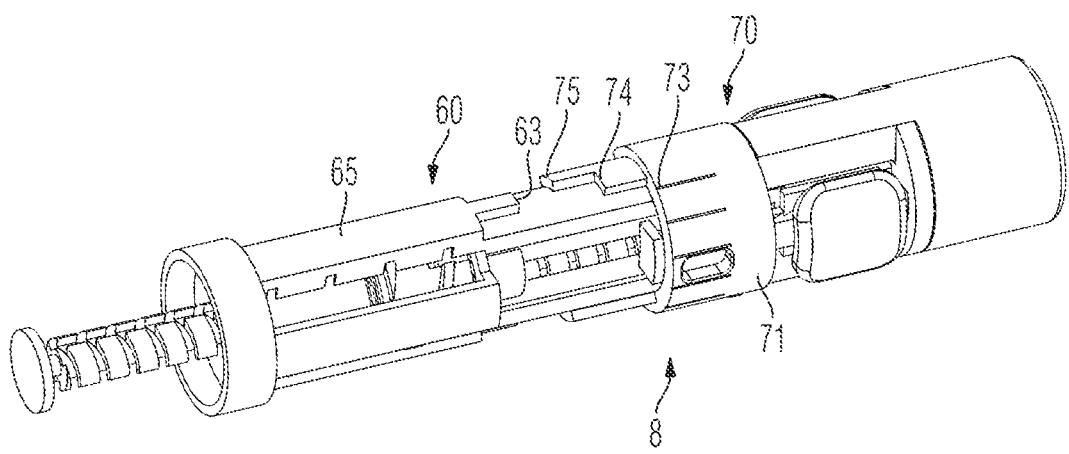
FIG. 4 is another perspective view of the drive mechanism with a preselector.
Figure 5:
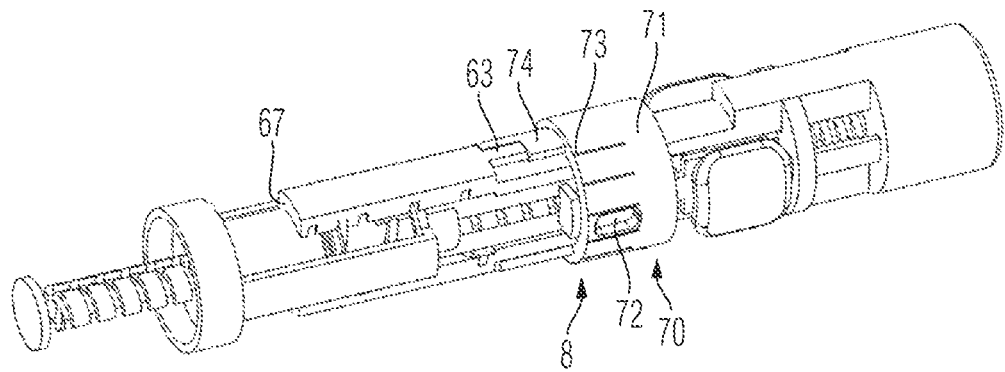
FIG. 5 shows the drive mechanism according to FIG. 4 with the dose tracker in an activation position.

The proximal portion or the main housing 10 of the injection device 1 is configured to house and to accommodate a drive mechanism 8 the entirety of which is illustrated in FIGS. 4 and 5. Here, the drive mechanism 8 is a combined drive mechanism 8 and dose setting mechanism 9. The drive mechanism 8 is configured to set and to dispense a dose of the medicament. Here, the drive mechanism 8 may coincide with a dose setting mechanism 9. In the following reference is made to the drive mechanism 8.

Figures 15, 16:
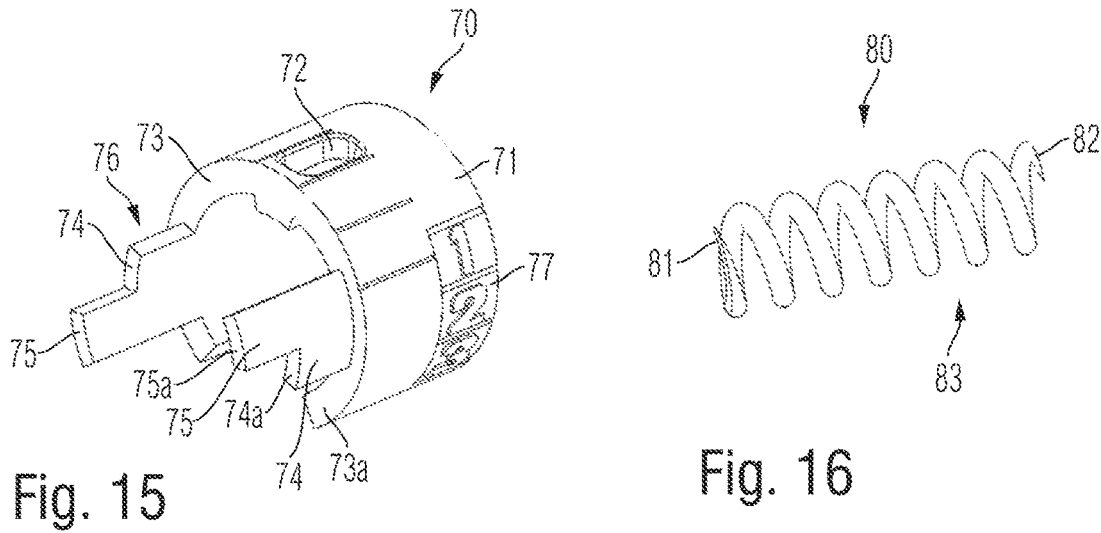
FIG. 15 shows the preselector.
FIG. 16 is a perspective view of the spring.
Figure 17:
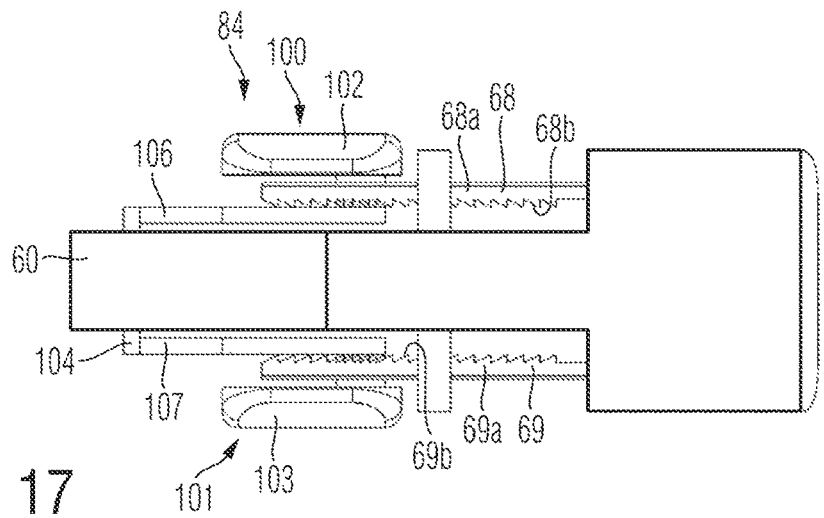
FIG. 17 is an enlarged side view of the interlock.
Figure 18:
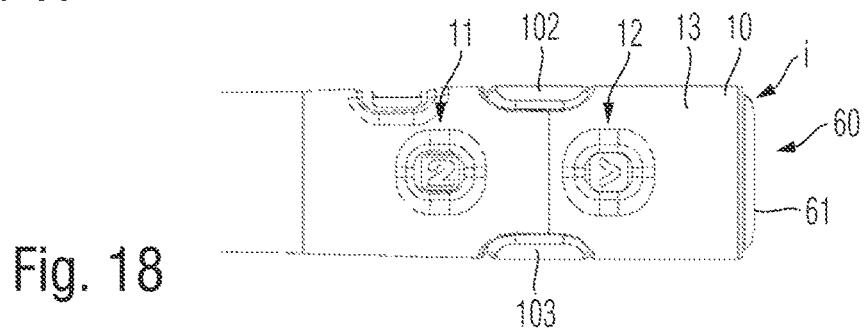
FIG. 18 shows the proximal end of the injection device with the dose tracker in the initial position.

Operation of the injection device 1 is as follows. For setting of a dose a user has to trigger a release member 100, 101, in form of a first and a second release button 102, 103. As illustrated in FIG. 17 the release members 100, 101 each comprise a release button 102, 103 that is located in a recess 19, hence in a through opening of a sidewall 13 of the housing 10 as indicated in FIG. 23. The release member 100, 101 belong to an interlock 84 that is configured to keep a dose tracker 60 in a retracted position or in an initial position i as shown in FIG. 18. The dose tracker 60 comprises a dose button 61 that is substantially flush with a proximal end face of the housing 10 when in the initial position i. The dose tracker 60 is biased in proximal direction 3 by a spring 80 as shown in FIG. 16. By activating the at least one release member, typically, e.g. by depressing both release members 100, 101 simultaneously, the interlock 84 between the dose tracker 60 and the housing 10 is deactivated or abrogated and the dose tracker 60 is free to become displaced in proximal direction 3 under the action of the spring 80. The dose tracker 60 is slidably engaged with the housing 10. It is prevented from rotating relative to the housing 10. The dose tracker 60 is configured to slide from the initial position i towards the activation position a as it is apparent from a comparison of FIG. 18 and FIG. 19.

Figure 19:
FIG. 19 shows the proximal end of the injection device with the dose tracker in an activation position.

In the activation position a as shown in FIG. 19 the dose tracker 60 is depressible, e.g. by a thumb of a user in distal direction 2 so as to advance the piston rod 20 in the distal direction 2 for displacing the piston 7 relative to the cartridge 6. In this way a predefined amount of the medicament can be expelled from the cartridge 6. For dispensing of the dose the dose tracker 60 is operably engaged with a piston rod 20. The drive mechanism 8 serves to transfer a distally advancing sliding motion of the dose tracker 60 into a rotational movement of the piston rod 20, which due to a threaded engagement with the housing 10 advances in distal direction 2 accordingly.

When the dose tracker 60 or the dose button 61 returns into the initial position as illustrated in FIG. 18 the interlock 84 is automatically reactivated so as to keep the dose tracker 60 in the initial position i against the action of the spring 80. A distally directed displacement of the dose tracker 60 acts against the force exerted by the spring 80. The spring 80 is hence biased or tensed as the dose tracker 60 is displaced in distal direction 2. When returning and arriving at the initial position i as illustrated in FIG. 18 the interlock 84 engages or re-engages. A repeated depression of at least one, typically of both release members 100, 101 disengages the interlock 84 and enables a repeated displacement of the dose tracker 60 relative to the housing 10 in proximal direction 3 towards the activation position a.

Figure 20:
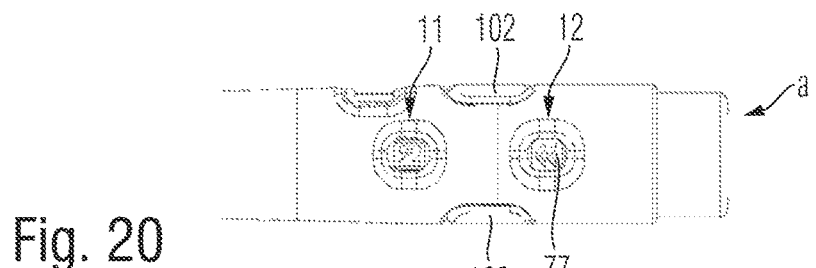
FIG. 20 shows the proximal end of the injection device with the dose tracker in another activation position.
Figure 21:
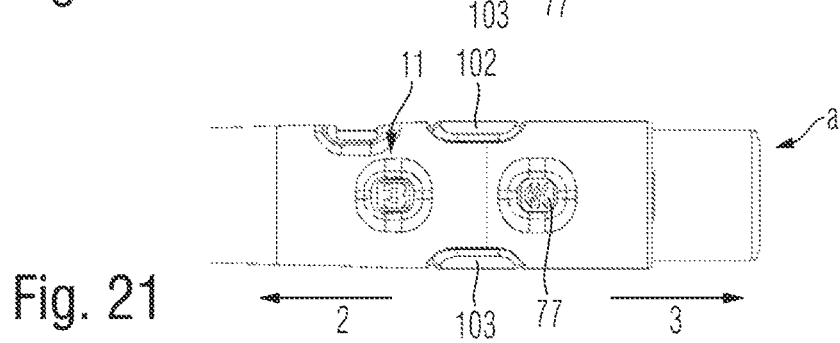
FIG. 21 shows the proximal end of the injection device with the dose tracker in a further activation position.

The length of a displacement path of the dose tracker 60 relative to the housing 10 between the initial position i as shown in FIG. 18 and one of the activation positions as shown in FIGS. 19 to 21 is correlated to the size of the dose actually set. The more the dose tracker 60 and the dose button 61 protrude from the proximal end of the housing 10 the larger is the size of the dose to be dispensed in the subsequent dose dispensing procedure.

Figure 12:
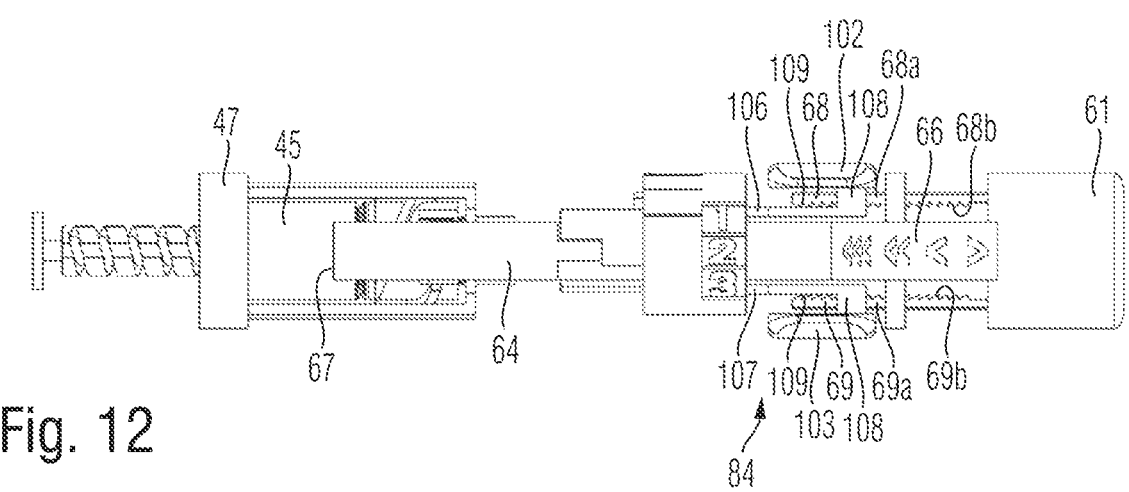
FIG. 12 is a side view of the drive mechanism.

In order to vary a size of a dose the injection device 1 there is provided a preselector 70 as illustrated in FIGS. 12 and 15. The preselector 70 is at least one of longitudinally or rotationally displaceable relative to the housing 10. It is translationally or rotationally displaceable relative to the housing 10 between at least two preselection positional states. With the example as currently illustrated the preselector 70 is rotatable relative to the housing 10. It is axially fixed to the housing 10. In any of at least two preselection positional states the preselector 70 is fixable to the housing 10. For this, the mutual engagement of the preselector 70 and the housing 10 may comprise a ratchet mechanism, such as at least one protrusion mechanically engageable with one of at least two or more recesses of corresponding shape.

The preselector 70 comprises a sleeve section 71. It is arranged inside the housing 10. An outside facing portion of the sleeve section 71 faces an inside facing portion of the sidewall 30 of the housing 10. The housing 10 comprises a preselection window 11 in a sidewall 13 of the housing 10 as illustrated in FIG. 18 to FIG. 21. On the outside surface of the sleeve section 71 of the preselector 70 there is provided at least one preselection indication 77, e.g. in form of one or several dose indicating numbers, such as 1, 2, 3. Depending on the rotational state of the preselector 70 relative to the housing 10 only one of the dose indicating numbers shows up in the preselection window 11. As shown in FIG. 19 a dose of size 1 is currently preselected. In FIG. 20 a dose of size 2 is preselected and in the configuration of FIG. 21 a dose size characterized by a number 3 is preselected.

The numbers or any other type of preselection indication, such as symbols or letters may represent several standard units of the medicament to be dispensed. For instance, a number 1 of a preselection indication 77 may represent 10 standard units of the medicament. For moving and for rotating the preselector 70 there is provided a radial recess 72 in the outside facing surface of the sleeve section 71. The recess 72 is aligned with a through opening 78 in the sidewall 13 of the housing 10 as illustrated in FIG. 23. Here, authorized persons, such as caregivers may use a tool to reach through the through opening 78 and to engage with the recess 72 of the sleeve section 71. Then, and by making use of the tool the preselector 70 can be rotated with regards to the longitudinal axis z of the elongated housing 10 as an axis of rotation. Consequently, another preselection indication 77 will show up in the preselection window 11. The through opening 78 as shown in FIG. 23 may be covered by a label, an adhesive tape or by a detachable cover so as to prevent unauthorized manipulation of the preselector 70.

As illustrated further in FIG. 15 the preselector 70 comprises numerous preselector stop features 73, 74, 75. The preselector stop features 73, 74, 75 extend in longitudinal direction and may protrude from the sleeve section 71 in distal direction 2. The preselector stop features 73, 74, 75 may be provided as stepped sections of a protrusion 76 that protrudes axially or longitudinally from the sleeve section 71 of the preselector 70.

The stop features 73, 74, 75 to be denoted as a first stop feature 73, as a second stop feature 74 and as a third stop feature 75 each comprise a respective stop face 73*a*, 74*a*, 75*a*. The stop faces 73*a*, 74*a*, 75*a* face in distal direction 2. The stop features 73, 74, 75 are configured to engage with a correspondingly shaped tracking stop feature 63 of the dose tracker 60. The tracking stop feature 63 comprises a proximally facing stop face 63*a*.

In an initial configuration as illustrated in FIG. 4 there is a longitudinal distance and a free space between the tracking stop feature 63 and any of the preselector stop features 73, 74, 75. This configuration represents the initial position i of the dose tracker 60. As the interlock 84 is released the dose tracker 60 is subject to a proximally directed advancing motion under the action of the relaxing spring 80. The dose tracker 60 is subject to the longitudinal movement until the stop face 63*a* of the tracking stop feature 63 gets in axial abutment with one stop face 73*a*, 74*a*, 75*a* of one of the preselector stop features 73, 74, 75.

In the configuration as shown in FIG. 5 the tracking stop feature 63 is in axial engagement and axial abutment with the second preselector stop feature 74. The proximally facing stop face 63*a* is in direct abutment with the distally facing stop face 74*a*. Since the stop features 63, 73, 74, 75 are located in a common radial plane and since the dose tracker 60 is in sliding engagement with the housing 10 the maximum size of the dose and hence the activation position of the dose tracker 60 is governed by the longitudinal alignment of the tracking stop feature 63 with one of the preselector stop features 73, 74, 75. Each stop feature 73, 74, 75 comprises a stop face 73*a*, 74*a*, 75*a*, wherein the stop faces of the various stop features 73, 74, 75 are axially and tangentially offset with respect to each other.

As illustrated in FIG. 15 the various preselector stop features 73, 74, 75 comprise different elongations in longitudinal or axial direction. The stop faces 73*a*, 74*a*, 75*a* of the stop features 73, 74, 75 are also located at an axial offset with respect to each other. If for instance the preselector 70 is rotated relative to the housing 10 in such a way that the distalmost stop feature 75 is aligned with the tracking stop feature 63 the displacement path of the dose tracker 60 is comparatively short as seen in proximal direction 3 until the tracking stop feature 63 gets in axial abutment with the respective stop feature 75.

If another preselector stop feature, such as the preselector stop feature 73 is in longitudinal alignment with the tracking stop feature 63 the movement of the dose tracker 60 from the initial position towards the activation position as illustrated in FIG. 21 is rather long, which corresponds to a maximum dose size. When the distalmost preselector stop feature 75 is longitudinally aligned with the tracking stop feature 63 the smallest preselection indication 77, i.e. number 1, shows up in the preselection window 11. When the most proximal preselector stop feature 73 is longitudinally aligned with the tracking stop feature 63 the largest preselection indication 77, i.e. number 3, shows up in the preselection window 11.

Starting from the configuration of FIGS. 5 and 20 and when rotating the preselector 70 in a clockwise direction as seen from the proximal end of the injection device 1 the proximal most preselector stop feature 73 becomes aligned with the tracking stop feature 63. Accordingly, a free path length for the longitudinal travel of the dose tracker 60 between the initial position i and the activation position a will be enlarged. When finally arriving in the activation position a as illustrated in FIG. 21 the dose button 61 and hence the dose tracker 60 protrudes even further from a proximal end of the housing 10 compared to the configuration of the preselector when another preselector stop feature 74 or 75 is aligned with the tracking stop feature 63.

The housing 10 further comprises a dose indicating window 12 in which the momentary state or position of the dose tracker 60 relative to the housing 10 is illustrated. In the dose indicating window 12 a dose size indicator 66 provided on an outside surface of the dose tracker 60 shows up. When in the initial position as shown in FIG. 18 a dose size indicator 66 may show up in form of an arrow indicating to a user, that the dose tracker 60 needs to be displaced towards the proximal direction 3. When reaching an activation position a as shown in any of the FIG. 19 to 21 different or identical dose size indicators 66 will show up in the dose indicating window 12 thereby indicating to a user that the injection device 1 is ready for dispensing and for expelling of the dose of the medicament. Here, the dose size indicators 66 may show an arrow pointing in the distal direction 2.

Figure 13:
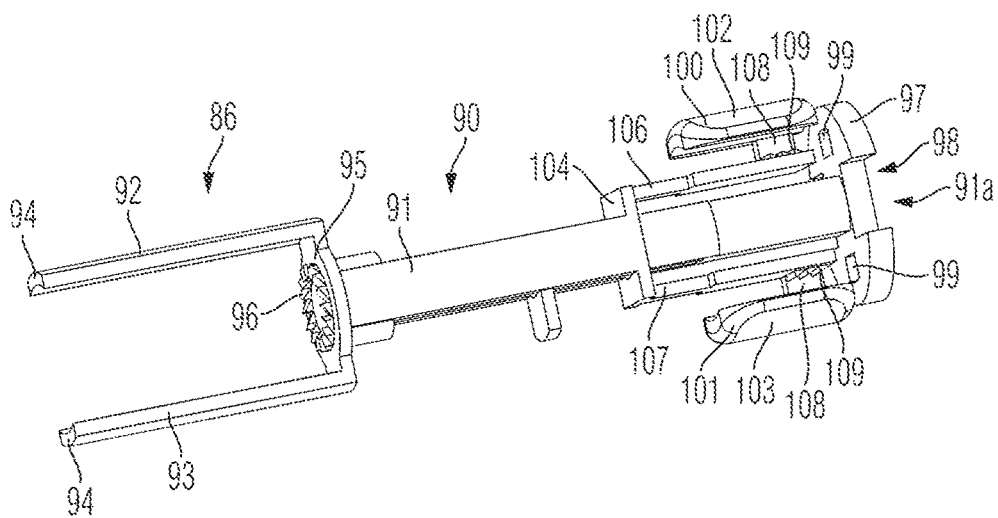
FIG. 13 is an isolated perspective view of a support fixed inside the housing of the injection device.
Figure 14:
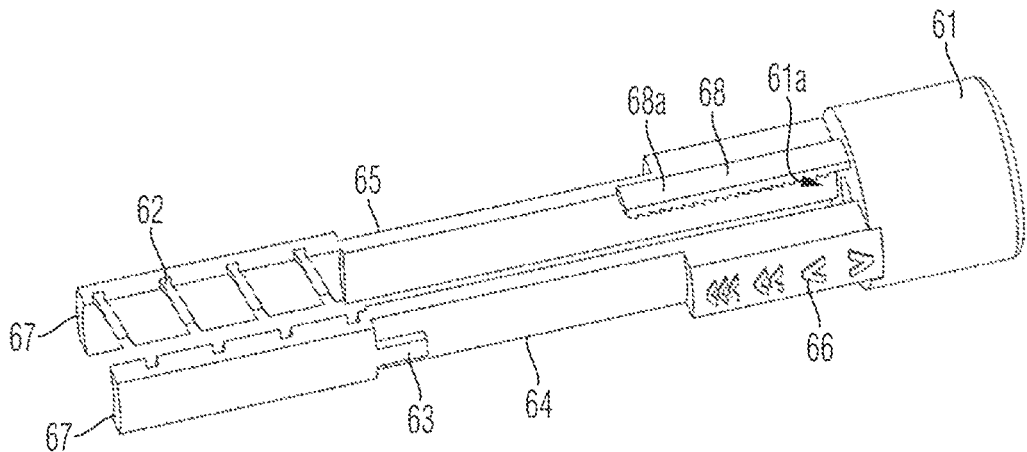
FIG. 14 is an isolated perspective view of the dose tracker.

The injection device 1 further comprises a support 90 as shown in FIG. 13. The support 90 is fixed inside the housing 10. It serves as a mounting support or mounting platform for several other components of the drive mechanism 8. The support 90 may be also integrally formed with the housing 10. For the purpose of assembly of the injection device 1 it may be beneficial to provide the support 90 as a separate component to be assembled and fixed inside the housing 10.

The support 90 comprises a body 91 of elongated shape. Towards a proximal end the body 91 comprises a radially widened flange section 97 having two diametrically oppositely located recesses 98. The dose tracker 60 comprises two elongated legs 64, 65, each of which being longitudinally guided in any one of the recesses 98. In this way the dose tracker 60 is longitudinally displaceable relative to the housing 10 and relative to the support 90. The dose tracker 60 is allowed to slide relative to the support 90 in longitudinal direction but is hindered to rotate relative to the support and/or relative to the housing 10.

The support 90 comprises two geometrically opposed and longitudinally extending strut sections 92, 93 each of which having a distal face 94. In a final assembly configuration as for instance shown in FIG. 23 the strut sections 92, 93 are in axial abutment with a threaded insert 44 or with a radially inwardly extending flange section of the housing 10. The threaded insert 44 is separately illustrated in FIG. 6. It may be integrally formed with an inside facing portion of the sidewall 13 of the housing 10. The threaded insert 44 comprises a sleeve section 45 through which the piston rod 20 extends in longitudinal direction. The sleeve section 45 and hence the threaded insert 44 comprises an inner thread 43 that is in threaded engagement with an outer thread 23 of the piston rod 20.

The threaded insert 44 comprises a radially widening socket section 47 extending radially outwardly from the sleeve section 45. The socket section 47 is connected to the sidewall 13 of the housing 10. The socket section 47 forms and comprises a radially outwardly extending shoulder portion 48. As illustrated in FIG. 23 the distal faces 94 of the strut sections 92, 93 are in axial abutment with the shoulder portion 48. In this way the support 90 can be axially fixed inside the housing 10. The elongated legs 64, 65 of the dose tracker 60 each comprise a distal face 67 that is configured to get in axial abutment with the shoulder portion 48 of the threaded insert 44 when arriving in the initial position i, e.g. at the end of a dose dispensing procedure. In this way the distally directed displacement of the dose tracker 60 can be blocked and limited thereby terminating a dose dispensing procedure.

The dose tracker 60 further comprises a tubular or knob-like shaped dose button 61 having a distally facing support face 61a. The dose button 61 forms a proximal end of the dose tracker 60. A distal end face of the dose button 61 may get in axial abutment with the flange section 97 of the support 90 as illustrated for instance in FIG. 23 in order to limit a distally directed displacement of the dose tracker 60 and in order to define the initial position i of the dose tracker 60.

In the initial position i as shown in FIG. 23 the support face 61a is in axial abutment with the flange section 97 of the support 90. Between the support 90 and the dose tracker 60 there is provided the spring 80. As illustrated in FIG. 23 the support 90 comprises a central bore in which a distal end 81 of the spring 80 is located. An opposite end of the spring, hence a proximal end 82, is located inside a bore of the dose tracker 60 or dose button 61. The distal end and/or the proximal end 81, 82 of the spring 80 are either fixed to the support 90 and to the dose tracker 60 or they are in abutment with respective abutment faces of the support 90 and the dose tracker 60.

The spring 80 comprises a helically wound compression spring 83. In the initial position of the dose tracker 60 the spring 80 is pre-tensioned at least to a predefined degree such that upon release of the interlock 84 the dose tracker 60 becomes subject to a proximally directed sliding motion relative to the support 90.

The interlock 84 is illustrated in greater detail in FIGS. 12, 17 and 23. It comprises a first engaging structure 68b, 69b connected to or integral with the dose tracker 60 and a second engaging structure 109 connected to or integral with the at least one release member 100, 101. The dose tracker 60 comprises two diametrically oppositely located and longitudinally extending interlock members 68, 69. The interlock members 68, 69 comprise longitudinally extending straight shaped arms or legs extending axially from a distal end of the dose button 61. The interlock members 68, 69 extend substantially parallel to the elongation of the legs 64, 65 of the dose tracker 60. As seen in circumferential direction the two interlock members 68, 69 are located tangentially or circumferentially between the diametrically oppositely located legs 64, 65.

The interlock members 68, 69 each extend through another recess 99 or through opening provided in the flange section 97 at the proximal end of the support 90. As shown in FIG. 17 in greater detail the interlock members 68, 69 each comprise an elongated arm 68a, 69a. Each one of the interlock members 68, 69 comprises an engaging structure 68b, 69b. In the present example the engaging structures 68b, 69b comprise a serrated or toothed surface that is selectively engageable with a correspondingly shaped engaging section 109 of the release members 100, 101.

The release members 100, 101 may be integrally formed with the support 90. Alternative, they are provided as separate components. The release members 100, 101 and the respective release buttons 102, 104 are provided at a free end of resilient arms 106, 107 of the support 90, which arms 106, 107 are deflectable in radial direction. As illustrated in FIG. 13 the resilient arms 106, 107 are provided and arranged on a flange section 104 of the support 90 protruding radially outwardly from the body 91 of the support 90.

The resilient arms 106, 170 extend substantially parallel to the arms 68a, 69a of the interlock members 68, 69. That side of the resilient arm 106 facing towards the interlock member 68 is provided with an engaging structure 109 in form of a toothed section configured to releasably engage with the engaging structure 68b. That side of the resilient arm 107 facing towards the interlock member 69 is also provided with a correspondingly shaped engaging section, in form of a toothed section 109. The teeth of the engaging sections 68b, 69b, 109 comprise a saw tooth profile thus allowing a distally directed sliding displacement of the dose tracker 60 relative to the release members 100, 101 and their respective resilient arms 106, 107.

The saw tooth profile of the engaging structures 68b, 69b, 109 is such, that the dose tracker 60 and hence the interlock members 68, 69 thereof are hindered from a proximally directed sliding displacement as long as the release member 100, 101, the release buttons 102, 103 and the resilient arms 106, 107 are located in an initial and non-depressed configuration.

As illustrated further in FIG. 17 the interlock members 68, 69 and hence the elongated arms 68a, 69a extend in longitudinally direction between the release buttons 102, 103 and the respective resilient arms 106, 107. In other words the interlock members 68, 69 each extend through a gap between the toothed section 109 and the corresponding release button 102, 103. The release buttons 102, 103 are connected to the resilient arms 106, 107 by means of a radially extending connecting piece 108 as shown in FIG. 13. The radial extension of the connecting piece 108 is larger than a radial thickness of the interlock members 68, 69, respectively.

By simultaneously depressing both release members 100, 101 and hence both release buttons 102, 103 the respective resilient arms 106, 107 are displaced radially inwardly thereby disengaging the engaging sections 109 of the release members 100, 101 from the engaging sections 68b, 69b of the interlock members 68, 69, respectively. In this way the interlock 84 is released and the dose tracker 60 is free to become displaced in proximal direction 3 under the action of the spring 80.

The support 90 further comprises a distally facing toothed section 96. The toothed section 96 may be provided in the region of or on a flange section 95 from which the two strut sections 92, 93 extend in distal direction 2. The toothed section 96 is of annular shape and faces in distal direction. The toothed section 96 comprises a saw-toothed profile.

Figure 6:
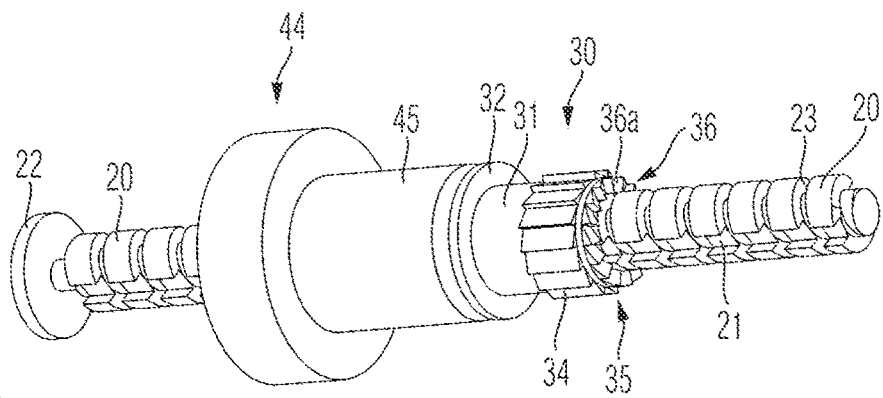
FIG. 6 is an isolated perspective view of the piston rod, a threaded insert and a driver.
Figure 7:
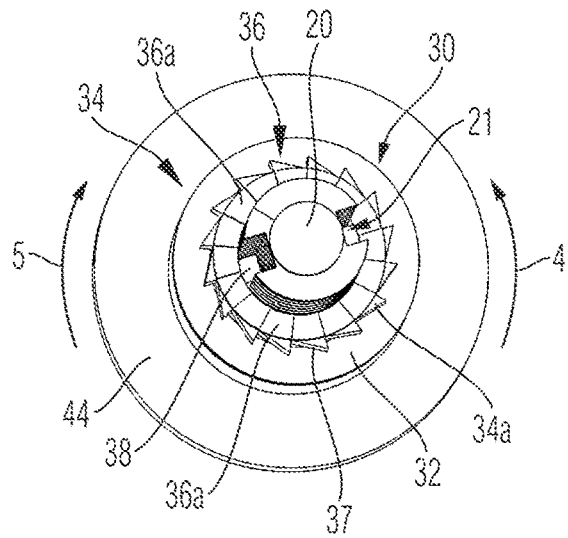
FIG. 7 is another perspective view of FIG. 6 as seen from the proximal end.

The piston rod 20 comprises a pressure foot 22 that is rotationally supported on the distal end of the piston rod 20. In this way the piston rod 20 is allowed to rotate relative to the pressure foot 22 when the pressure foot 22 is in axial abutment with a proximal thrust receiving surface of the piston 7 of the cartridge 6. A detailed view of the piston rod is shown in FIG. 6. The piston rod 20 comprises an outer thread 23 that is threadedly engaged with the inner thread 43 of the threaded insert 44. Alternative, the piston rod 20 extends through a threaded bore of the housing 10. The piston rod 20 further comprises two elongated, straight shaped and axially extending grooves 21 intersecting the outer thread 23. As illustrated in FIG. 7 the oppositely located grooves 21 are in a splined engagement with radially inwardly extending protrusions 38 of a driver 30.

Figure 10:
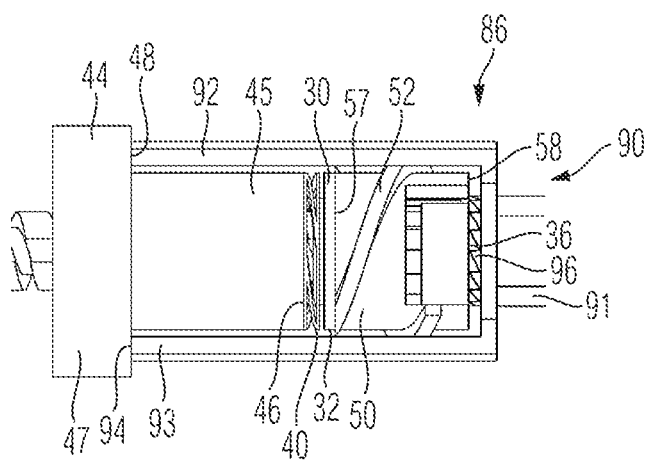
FIG. 10 is a side view of the arrangement according to FIG. 9 when arranged inside the housing of the injection device.
Figure 11:
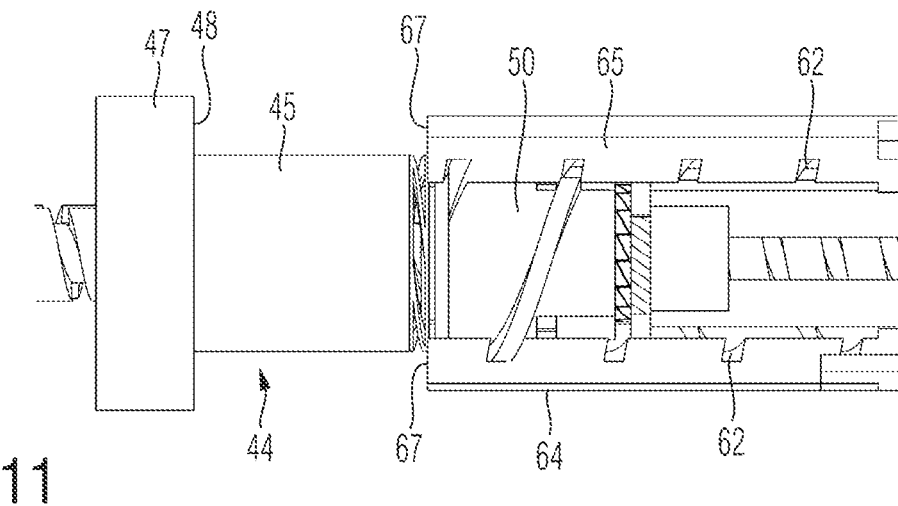
FIG. 11 is another side view of the arrangement according to FIG. 10.

The driver 30 comprises a sleeve section 31 enclosing an axial portion of the piston rod 20. The driver 30 further comprises a radially widened flange 32 near or at its distal end. The flange 30 is in axial abutment with a clutch spring 40. The clutch spring 40 as shown in FIG. 10 is axially sandwiched between a proximal face 46 of the threaded insert 44 and the distal end of the driver 30.

Figure 9:
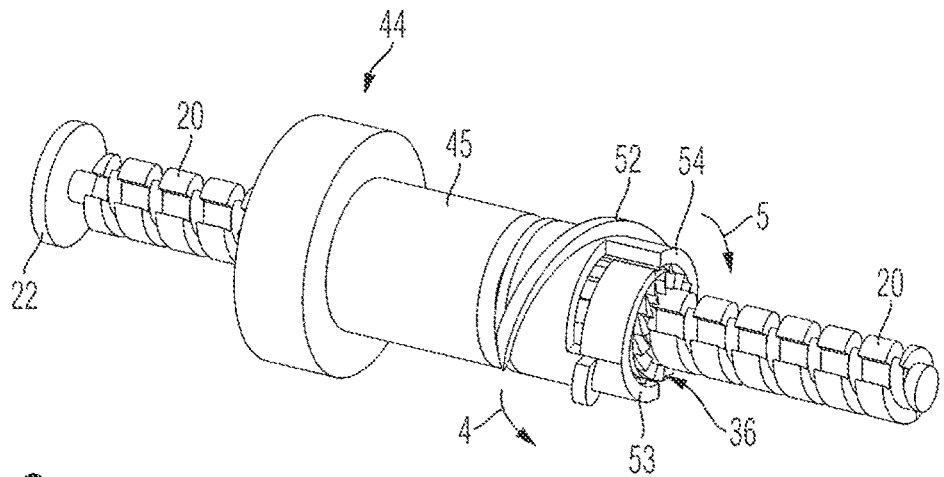
FIG. 9 is a perspective view of the components of FIG. 6 together with the clutch.

An opposite end of the driver 30, hence the proximal end thereof is provided with a first toothed section 36 that is in engagement with the toothed section 96 of the support 90. The first toothed section 36 is also of saw-toothed profile and comprises an annular shape. Both, the first toothed section 36 and the toothed section 96 may comprise or form a kind of a crown wheel. Since the first toothed section 36 and the toothed section 96 are of saw tooth profile a rotation of the driver 38 along the first sense of rotation as indicated in FIG. 9 is permanently prevented.

Since the driver 30 is in splined engagement with the piston rod 20 through the protrusion 38 a back winding or retraction of the piston rod 20 towards the proximal direction 3 is effectively impeded and prevented.

A rotation along a second sense of rotation 5 opposite to the first sense of rotation 4 is supported and allowed by the engagement of the toothed sections 36, 96. If a torque along the second sense of rotation 5 is applied to the driver 30 the teeth of the first toothed section 36 will slide along the teeth of the toothed section 96 of the support 90 thereby axially tensioning the clutch spring 40 until the tips of the teeth of the first toothed section 36 pass respective tips of the teeth of the toothed section 96. As soon the mutually corresponding teeth have passed the clutch spring 40 urges the driver 40 in proximal direction so that the teeth of the first toothed section 36 engage with circumferential consecutive teeth of the toothed section 96 of the support 90.

Hence, during a rotation along the second sense of rotation and hence during dispensing of a dose the driver 30 is subject to a stepwise discrete rotational displacement that is accompanied by a small axial displacement in accordance with the axial height of the teeth of the toothed sections 36, 96. The driver 30 further comprises a second toothed section 34 extending along the outer circumference of the sleeve section 31. The second toothed section 36 comprises teeth of saw toothed shape.

There is further provided a clutch enclosing at least a portion of the driver 30. As shown in FIGS. 9 and 10 the clutch 50 comprises a distal face 57 in axial abutment with the proximal side of the flange 32 of the driver 30. The clutch 50 comprises an outer thread 52 that is in threaded engagement with an inner thread 62 provided on a distal section of the dose tracker. 60. The inner thread 62 is provided on and/or distributed on the two legs 64, 65 of the dose tracker 64. In this way a longitudinal sliding displacement of the dose tracker 60 is transferable into a rotation of the clutch 50.

Figure 8:
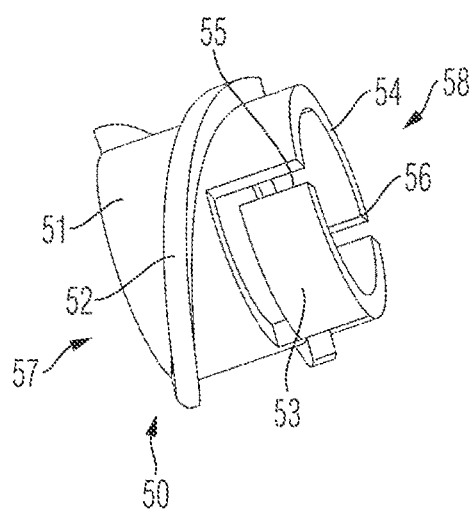
FIG. 8 is an isolated perspective view of a clutch.

The threaded engagement between the dose tracker 60 and the clutch 50 is such that a proximally directed displacement of the dose tracker 60 relative to the clutch 50 leads to a rotation of the clutch 50 along the first sense of rotation 4. A displacement of the dose tracker 60 in distal direction 2 relative to the clutch 50 leads to a rotation of the clutch 50 along the second sense of rotation 5. The clutch 50 further comprises engaging sections 55, 56 as indicated in FIG. 8. The engaging sections 55, 56 are provided at ends of resiliently deformable arc-shaped ratchet members 53, 54 provided at a proximal end of the clutch 50.

The engaging sections 55, 56 are in permanent engagement with the teeth of the second toothed section 34 of the driver 30. Due to the saw tooth profile of the second toothed section 30 the ratchet members 53, 54 of the clutch 50 slide along and relative to the second toothed section 34 along the first sense of rotation 4 during the process of dose setting and while the dose tracker is subject to a proximally directed displacement. A rotation of the clutch 50 along the first sense of rotation 4 is accompanied by an audible click sound. Such a click sound is generated each time when an engaging section 55, 56 passes a tip of a tooth of the second toothed section 34. As the clutch 50 is rotated along the first sense of rotation 4 the driver 30 is and remains in torque proof engagement with the support 90 by means of the first toothed section 36 and produced section 96. The driver 30 remains rotationally locked to the housing 10.

The free end of each of the ratchet members 53, 54 is in tangential or circumferential abutment with a steep flank of a tooth of the second toothed section 34. When subject to a rotation in the second sense of rotation 5 the engaging sections 55 remain in abutment with the steep flank of a tooth or several teeth of the second toothed section 36 thereby transferring a respective angular momentum to the driver 30 along the second sense of rotation 5.

The clutch 50 is axially or longitudinally sandwiched between the flange section 95 of the support 90 and the flange 32 of the driver 30. In this way the clutch 50 is axially fixed inside the housing 10. A proximal face 58 of the clutch 50 is in axial abutment with the support 90.

Operation of the injection device 1 is as follows. When handed out to a patient or consumer the injection device 1 may be ready for dispensing. The injection device may be preconfigured or manufactured in such a way that a priming procedure is not necessary. Alternatively, it is conceivable, that the injection device has to undergo a priming procedure or an air shot so as to make sure that the pressure foot 22 of the piston rod 20 is in direct abutment with the piston 7 of the cartridge 6.

A user has to depress the two release members 100, 101 simultaneously. In this way the two sections 109 thereof and the interlock members 68, 69 disengage and are operably released from each other. The dose tracker 60 is then free to be displaced in proximal direction 3 under the action of the releasing spring 80. This proximally directed displacement of the dose tracker 60 continues until the tracking stop feature 63 of the dose tracker 60 gets in axial abutment with one of the preselector stop features 73, 74, 75. Then and due to the proximally directed displacement of the dose tracker 60 the those button 61 thereof protrudes from a proximal end of the housing 10 as for instance illustrated in FIG. 20. The device is then ready for dispensing or for expelling of a dose of the medicament. In the preselection window 11 the preselected size of a dose is indicated. In the corresponding dose indicating window 12, e.g. two arrows show up thus indicating to the user that the dose button 61 can now be depressed in distal direction 2.

The proximal displacement of the dose tracker 60 is accompanied by a rotation of the clutch 50 in the first sense of rotation 4 as illustrated in FIG. 9. The driver 30 is kept stationary and remains in non-rotational engagement with the support 90 by the toothed sections 36 and 96. This rotational interlock is further supported by the clutch spring 40 configured to urge the driver 30 in a unidirectional torque proof and non-rotative engagement with the support 90.

During a dose dispensing procedure in which the dose tracker 60 is depressed in distal direction 2 against the action of the spring 80 the clutch 50 is subject to a rotation along the second sense of rotation 5. The ratchet members 53, 54 of the clutch 50 and their engaging sections 55, 56 are configured to transfer an angular momentum from the clutch 50 to the driver 30. Insofar the driver 30 also starts to rotate along the second sense of rotation 5. The radially inwardly extending protrusions 38 of the driver 30 are in splined engagement with respective longitudinal grooves 21 of the piston rod 20. A rotation of the driver 30 along the second sense of rotation 5 therefore transfers into a respective rotation of the piston rod 20. Due to the threaded engagement of the piston rod 20 with the housing 10 the piston rod 20 becomes subject to a respective distally directed advancing motion thereby expelling a respective amount of the medicament from the cartridge 6.

The longitudinal travel of the dose tracker 60 relative to the housing 10 between the initial position i and a respective activation position a is determined by the positional state of the preselector 70. The preselector 70 comprises at least one axially extending protrusion 76. As shown in FIG. 15 the preselector 70 may even comprise two diametrically oppositely located and symmetrically configured protrusions 76 each of which having numerous preselector stop features 75, 74. A bottom of the protrusion 76 and hence a rim of the sleeve section 71 of the preselector 70 may form or comprise another preselector stop feature 73. Each of the preselector stop features 73, 74, 75 comprises a well-defined stop face 73a, 74a, 75a. One of the stop faces 73a, 74a, 75a can be brought in axial alignment with the tracking stop feature 63. The free space between the tracking stop feature 63 and that particular stop face 73a, 74a, 75a that is in axial alignment with the tracking stop feature 63 determines the axial distance that the dose tracker 60 can be displaced between the initial position i and the at least one activation position a.

Modifying of a preselection of a dose requires a rotation of the preselector 70 with the longitudinal axis of the injection device as an axis of rotation. In this way another one of the preselector stop features 73, 74, 75 can be brought in longitudinal alignment with the tracking stop feature 63. Since the axial positions of the preselector stop features 73, 74, 75 all differ, correspondingly modified longitudinal displacement paths of the dose tracker 60 can be implemented.

The driver 30 comprises a driver sleeve section 31 enclosing an axial portion of the piston rod 20. The driver 30 comprises a radially widened flange 32 near or at its distal end. The flange 32 is in axial abutment with a clutch spring 40. The clutch spring 40 as illustrated in FIG. 10 is axially sandwiched between a proximal face 46 of the threaded insert 44 and the distal end of the driver 30. The clutch spring 40 is configured or comprises a compression spring. One end of the clutch spring 40 is supported by the proximal face 46 of the threaded insert 44 and an opposite end of the clutch spring 40 is in abutment with the flange 32 of the driver 30. The distal end of the clutch spring 40 may be alternatively in abutment with a proximal face, with a rim or with a radially inwardly extending flange section of the housing 10.

As illustrated further in FIGS. 6, 7 and 9 the driver 30 comprises a first toothed section 36 and a second toothed section 34 at or near a proximal end of the driver 30. The first toothed section 36 is provided at an axial face 35, typically at an axial end face 35 of the driver. It is provided at a proximal axial end face. It is configured to engage with a correspondingly-shaped toothed section 96 of the support 90. The support 90 is separately illustrated in FIG. 13. The first toothed section 36 is of annular shape and comprises numerous teeth 36a that are arranged next to each other along the circumference of the driver sleeve section 31. Typically, the teeth 36a of the first toothed section 36 resemble or comprise a hirth toothing, wherein the tips of the teeth 36a protrude in axial direction and wherein the grooves between consecutive teeth 36a extend radially with regard to the tubular shape of the driver sleeve section 31.

The teeth 36a of the first toothed section 36 comprise a saw tooth profile. Hence, the teeth 36a of the first toothed section 36 each comprise a saw tooth 36a. The saw teeth 36a of the first toothed section 36 comprise a steep edge and a shallow or flat edge. As illustrated in FIGS. 6 and 9 the steep edges of the teeth 36a of the first toothed section 36 face towards a first sense of rotation or in a first direction 4. The shallow or flat edges of the saw teeth 36a of the first toothed section 36 faces towards a second sense of rotation or in a second direction 5 as illustrated in FIG. 9.

The support 90 comprises a correspondingly-shaped toothed section 96 as illustrated in FIGS. 10 and 13. The correspondingly-shaped toothed section 96 also comprises numerous saw teeth that are of substantially identical shape and size compared to the saw teeth 36a of the first toothed section 36. Since the driver 30 is biased by the clutch spring 40 in proximal direction 3 the first toothed section 36 provided at the proximal end face 35 of the driver 30 is kept in abutment and in engagement with the correspondingly-shaped toothed section 96 of the support 90. Due to the mutually corresponding saw toothed profiles of the first toothed section 36 and the correspondingly-shaped toothed section 96 a rotation of the driver 30 along the first direction 4 is permanently prevented. A rotation in the opposite, hence along the second direction 5 is allowed and supported.

When the driver 30 is rotated in the second direction 5 the shallow or flat-shaped edges of the first toothed section 36 and the correspondingly-shaped toothed section 96 are allowed to slide relative to each other. Such a rotational motion of the first toothed section 36 relative to the toothed section 96 of the support 90 may be accompanied by a slight axial displacement of the driver 30 in longitudinal direction (z).

As the shallow edges of the teeth 36a of the first toothed section 36 and the correspondingly-shaped toothed section 96 are subject to a relative sliding displacement in circumferential direction the axial slope of the saw toothed profiles of the teeth of the toothed sections 36, 96 leads to a distally directed sliding motion of the driver 30 until the crest or tips of the teeth of the mutually engaged toothed sections 36, 96 pass each other. As soon as the tips of the teeth of the mutually corresponding toothed sections 36, 96 have passed, the clutch spring 40 urges the driver 30 in proximal direction 3 so that the tips or crests of the toothed section 36 engage with the grooves of the correspondingly-shaped toothed section 96 and vice versa.

The rotation of the driver 30 along and in the second direction 5 may be thus accompanied by a back and forth movement of the driver 30 in longitudinal direction. The stepwise and ratchet-like rotational movement of the driver 30 relative to the support 90 and relative to the housing 10 may be further accompanied by an audible click sound thus providing an audible feedback to the user or healthcare giver that a dispensing or drug delivery operation is currently in process.

When the driver should become subject to a torque along the first direction 4 the steep edges of the teeth 36a of the first toothed section 36 are and remain in torque-proof engagement with correspondingly-shaped steep edges of the saw teeth of the correspondingly-shaped toothed section 96 of the support 90. In this way a rotation of the driver 30 along the first direction 4 is effectively prevented.

Since the driver 30 is in permanent splined engagement with the piston rod 20 through the protrusion 38 a back winding or retraction of the piston rod 20 along or in proximal direction 3 is effectively impeded and prevented. A rotation along the second direction 5 or along the second sense of rotation opposite to the first sense of rotation or direction 4 is supported and allowed by the engagement of the toothed sections 36, 96.

The injection device 1 further comprises a clutch 50 having a hollow interior 59. The clutch 50 is configured to receive at least a portion of the driver 30 inside the hollow interior 59. At least a portion of the driver sleeve section 31 and/or a portion of the driver 30 is arranged inside the hollow interior 59 of the clutch 50. In this way a nested or interleaved configuration of the driver 30 and the clutch 50 can be provided. This allows for a rather stable and robust construction of the drive mechanism 8 of the injection device 1.

Moreover, the at least partially nested or interleaved arrangement and configuration enables a rather compact and space saving design of the injection device 1. The partially interleaved or nested configuration is also beneficial in that the driver 30 and the clutch 50 provide mutual support with regard to a rotation relative to the housing 1. For instance, the driver 30 is mechanically supported by the piston rod 20 and the interleaved or nested arrangement between the driver 30 and the clutch 50 provides a rotational support for the clutch 50. Since the clutch 50 receives at least a portion of the driver sleeve section 31 the clutch 50 is rotationally supported by the driver 30. This is beneficial for a torque transmitting engagement between the clutch 50 and the driver 30 and may reduce mechanical tolerances and backlash between the various components of the injection device 1.

As shown in FIGS. 9 and 10 the clutch 50 and in particular a clutch sleeve section 51 thereof comprises a distal face 57 in axial abutment with the proximal side of the flange 32 of the driver 30. The clutch 50 further comprises an outer thread 52 that is in threaded engagement with an inner thread 62 provided on a section of the dose tracker 60. The inner thread 62 is provided on and/or distributed on the two legs 64, 65 of the dose tracker 60. In this way a longitudinal sliding displacement of the dose tracker 60 is transferrable into a rotation of the clutch 50. The threaded engagement between the dose tracker 60 and the clutch 50 is such that a proximally directed displacement of the dose tracker 60 relative to the housing 10 or relative to the clutch 50 leads to a rotation of the clutch 50 along the first direction 4.

An oppositely directed sliding displacement of the dose tracker 60 in distal direction 2 relative to the housing 10 and hence relative to the clutch 50 leads to a rotation of the clutch 50 along the second direction 5. The clutch 50 and the dose tracker 60 are permanently threadedly engaged. Any axial sliding displacement of the dose tracker 60 relative to the housing 10 and/or relative to the clutch 50 transfers into a respective rotation of the clutch 50 along the first direction or the second direction.

The clutch 50 is in unidirectional torque transmissive engagement with the driver 30. This is achieved by a second toothed section 34 provided on an outside surface of a sidewall 37 of the driver sleeve section 31. The second toothed section 34 also comprises numerous saw teeth 34a each of which protruding radially outwardly from the outside surface of the sidewall 37 as illustrated in FIG. 7. The saw teeth 34a each comprise a steep edge facing in or along the first direction 4. The saw teeth 34a also comprise a shallow or flat edge facing towards the second direction 5.

The second toothed section 34 may be arranged axially adjacent to the first toothed section. The steep and flat or shallow edges of the teeth 36a, 34a may be in radial alignment or may flush in radial direction. Hence, the first toothed section 36 and the second toothed section 34 comprise an equal number of consecutive teeth.

The clutch 50 comprises at least one engaging section 55, 56. Typically and as illustrated in FIG. 8 the clutch 50 comprises a first and a second engaging section 55, 56. The engaging sections 56 are located at free ends 53a, 54a of a first and a second ratchet member 53, 54, respectively. Generally, the clutch 50 comprises at least one ratchet member 53, 54 that is resiliently deformable in radial direction. In the presently illustrated example the clutch 50 comprises two ratchet members, namely a first ratchet member 53 and a second ratchet member 54. The ratchet members 53, 54 are provided at a proximal end of the clutch 50 and hence at a proximal end of the clutch sleeve section 51.

A proximal face 58 of the clutch 50 is formed by or constituted by the first and the second ratchet members 53, 54. Each one of the at least first and second ratchet members 53, 54 comprises an arc-shaped geometry that is conformal to a sidewall 51a of the clutch sleeve section. Hence, the ratchet members 53, 54 are axially flush with the sidewall 51a of the clutch sleeve section 51. The ratchet members 53, 54 are integrally formed with the clutch 50 and hence with the clutch sleeve section 51. The clutch 50 may comprise or may consist of an injection molded plastic component.

The free ends 53a, 54a of the ratchet members 53, 54 are separated from the clutch sleeve section 51 by a longitudinal or L-shaped slit in the sidewall 51a of the clutch sleeve section 51. The engaging sections 55, 56 may comprise radially inwardly extending protrusions to engage with the steep edges of the saw teeth 34a of the second toothed section 34. However, it may be even sufficient that an end face of the ratchet members 53, 54 gets in engagement with the steep edges of the saw teeth 34a.

This may be attained when the outer diameter of the second toothed section 34 as measured at the tips of the saw teeth 34a is slightly larger than an inside diameter of the clutch sleeve section 51 in the region of the first and second ratchet members 53, 54. In this way the ratchet members 53, 54 are resiliently deformed radially outwardly when the second toothed section 34 is located in the free space between the at least two ratchet members 53, 54.

Alternatively it is conceivable, that the ratchet members 53, 54 are biased radially inwardly so that in an initial configuration the free ends of the ratchet members 53, 54 and hence the engaging sections 55, 56 thereof protrude radially inwardly from the inside surface of the sidewall 51a of the clutch sleeve section 51. As the clutch 50 receives the driver 30 the ratchet members 53, 54 will then be at least slightly biased radially outwardly when engaging with the second toothed section 34.

The present example shows resiliently deformable ratchet members 53, 54. However, the injection device 1 is by no way limited to resiliently deformable ratchet members. It is also conceivable, that the ratchet members 53, 54 are pivotally supported on the clutch 50. They may be pivotable radially outwardly against a restoring force that may be provided by a spring not further illustrated here. In this way, a similar ratchet effect could be attained.

As illustrated in FIG. 9 the engaging sections 55, 56 are in permanent engagement with the saw teeth 34a of the second toothed section 34 of the driver 30. The saw toothed profile of the second toothed section 34 is selected such, that the ratchet members 53, 54 of the clutch 50 slide along and relative to the second toothed section 34 as the clutch 50 is rotated along the first direction 4 during a dose setting procedure. Since the driver 30 is hindered to rotate along the first direction 4 through the engagement with the support 90 the driver 30 cannot follow the rotation of the clutch 50 that is induced by a proximally directed displacement of the dose tracker 60.

The rotation of the clutch 50 along the first direction 4 is accompanied by an audible click sound that is generated as the ratchet members 53, 54 pass a tip of the teeth 34a of the second toothed section 34. A click sound is generated each time when an engaging section 55, 56 passes over a tip of a tooth 34a of the second toothed section 34 thereby providing an audible feedback to the user of the injection device 1 that a dose setting procedure is in progress. As the clutch 50 is rotated in the first direction 4 the driver 30 is and remains in torque-proof engagement with the support 90.

When the clutch 50 is subject to a rotation in the second direction 5 the engaging sections 55, 56 remain in abutment with the steep flange or steep edge of the teeth 34a of the second toothed section 34 thereby transferring a respective angular momentum or torque to the driver 30 along the second direction 5. Consequently, the driver 30 is rotated in the second direction 5 which rotation is equally transferred to a rotation of the piston rod 20.

Due to its threaded engagement with the threaded insert 44 the piston rod 20 advances in distal direction 2 so as to expel the set dose of the medicament from the cartridge 6.

The clutch 50 is axially or longitudinally sandwiched between the flange section 95 of the support 90 and the flange 32 of the driver 30. In this way the clutch 50 is axially constrained inside the housing 10. A proximal face 58 of the clutch 50 is in axial abutment with the support 90 or with the support 90. The distal face 57 of the clutch is in axial abutment with a proximal side of the flange 32 of the driver 30. When the dose tracker 60 is depressed in distal direction 2 the clutch 50 may be subject to a distally directed displacement before it starts to rotate due to the threaded engagement with the dose tracker 60.

The axially distally directed displacement of the clutch 50 at the beginning of a dose dispensing procedure is transferred to a respective axial displacement of the driver 30 since the distal face 57 of the clutch 50 is and remains in abutment with the proximal side of the flange 32. In this way the first toothed section 36 may disengage from the toothed section 96 of the support 90. Accordingly, the driver 30 may start to rotate along the second direction 5 while being out of contact with the support 90. Consequently, a dispensing force to be applied to the dose tracker 60 in distal direction 2 can be decreased because there is no longer a friction between the first toothed section 36 and the correspondingly shaped toothed section 96 of the support 90 as long as the dose tracker 60 is depressed, e.g. by a thumb of a user.

Operation of the injection device 1 is as follows. When handed out to a patient or consumer the injection device 1 may be ready for dispensing. The injection device may be preconfigured or manufactured in such a way that a priming procedure is not necessary. Alternatively, it is conceivable, that the injection device has to undergo a priming procedure or an air shot so as to make sure that the pressure foot 22 of the piston rod 20 is in direct abutment with the piston 7 of the cartridge 6.

A user has to depress the two release members 100, 101 simultaneously. In this way the two sections 109 thereof and the interlock members 68, 69 disengage and are operably released from each other. The dose tracker 60 is then free to be displaced in proximal direction 3 under the action of the releasing spring 80. This proximally directed displacement of the dose tracker 60 continues until the tracking stop feature 63 of the dose tracker 60 gets in axial abutment with one of the preselector stop features 73, 74, 75. Then and due to the proximally directed displacement of the dose tracker 60 the those button 61 thereof protrudes from a proximal end of the housing 10 as for instance illustrated in FIG. 20. The device is then ready for dispensing or for expelling of a dose of the medicament. In the preselection window 11 the preselected size of a dose is indicated. In the corresponding dose indicating window 12, e.g. two arrows show up thus indicating to the user that the dose button 61 can now be depressed in distal direction 2.

The proximal displacement of the dose tracker 60 is accompanied by a rotation of the clutch 50 in the first sense of rotation 4 as illustrated in FIG. 9. The driver 30 is kept stationary and remains in non-rotational engagement with the support 90 by the toothed sections 36 and 96. This rotational interlock is further supported by the clutch spring 40 configured to urge the driver 30 in a unidirectional torque proof and non-rotative engagement with the support 90.

During a dose dispensing procedure in which the dose tracker 60 is depressed in distal direction 2 against the action of the spring 80 the clutch 50 is subject to a rotation along the second sense of rotation 5. The ratchet members 53, 54 of the clutch 50 and their engaging sections 55, 56 are configured to transfer an angular momentum from the clutch 50 to the driver 30. Insofar the driver 30 also starts to rotate along the second sense of rotation 5. The radially inwardly extending protrusions 38 of the driver 30 are in splined engagement with respective longitudinal grooves 21 of the piston rod 20. A rotation of the driver 30 along the second sense of rotation 5 therefore transfers into a respective rotation of the piston rod 20. Due to the threaded engagement of the piston rod 20 with the housing 10 the piston rod 20 becomes subject to a respective distally directed advancing motion thereby expelling a respective amount of the medicament from the cartridge 6.

The longitudinal travel of the dose tracker 60 relative to the housing 10 between the initial position i and a respective activation position a is determined by the positional state of the preselector 70. The preselector 70 comprises at least one axially extending protrusion 76. As shown in FIG. 15 the preselector 70 may even comprise two diametrically oppositely located and symmetrically configured protrusions 76 each of which having numerous preselector stop features 75, 74. A bottom of the protrusion 76 and hence a rim of the sleeve section 71 of the preselector 70 may form or comprise another preselector stop feature 73. Each of the preselector stop features 73, 74, 75 comprises a well-defined stop face 73a, 74a, 75a. One of the stop faces 73a, 74a, 75a can be brought in axial alignment with the tracking stop feature 63. The free space between the tracking stop feature 63 and that particular stop face 73a, 74a, 75a that is in axial alignment with the tracking stop feature 63 determines the axial distance that the dose tracker 60 can be displaced between the initial position i and the at least one activation position a.

Modifying of a preselection of a dose requires a rotation of the preselector 70 with the longitudinal axis of the injection device as an axis of rotation. In this way another one of the preselector stop features 73, 74, 75 can be brought in longitudinal alignment with the tracking stop feature 63. Since the axial positions of the preselector stop features 73, 74, 75 all differ, correspondingly modified longitudinal displacement paths of the dose tracker 60 can be implemented.

Figure 2:
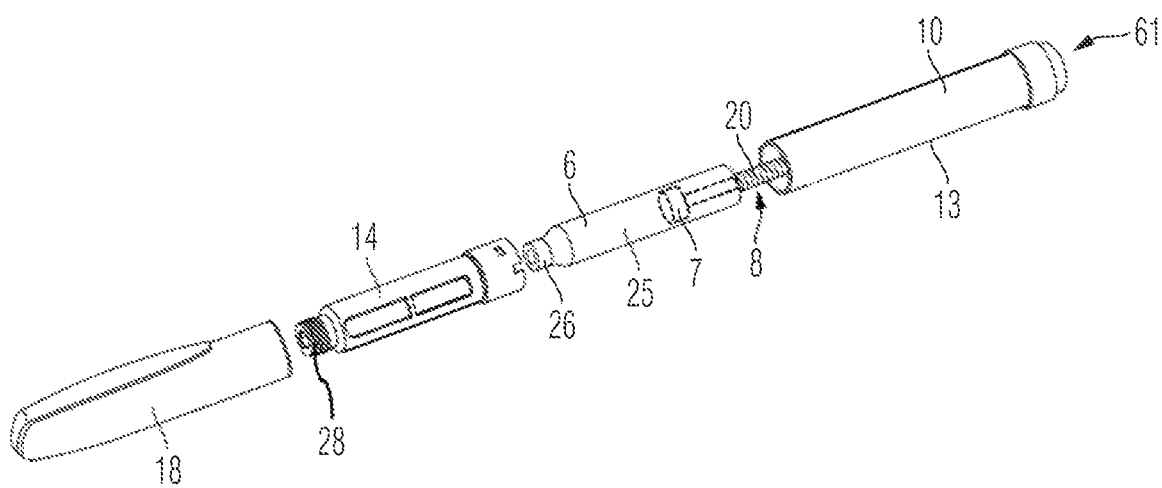
FIG. 2 is an exploded view of components of the injection device of FIG. 1.
Figure 3:
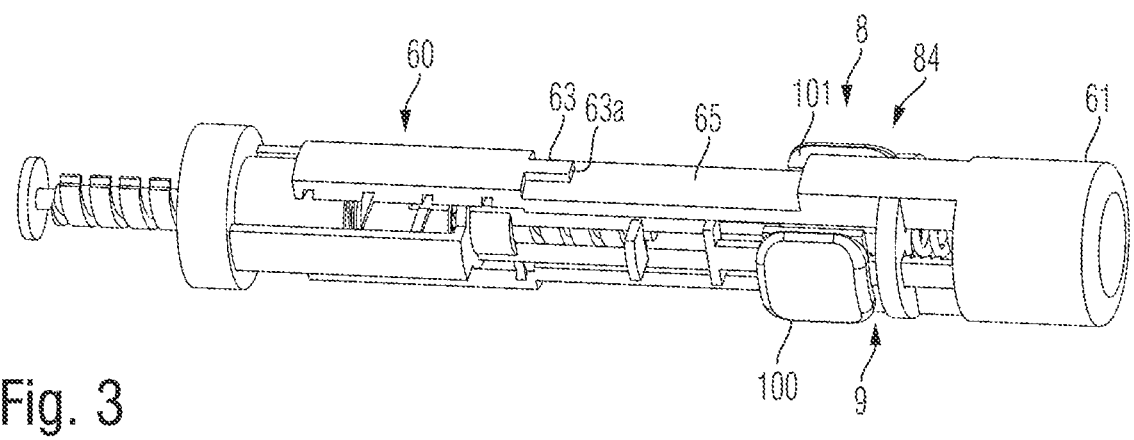
FIG. 3 shows an isolated perspective view of a drive mechanism of the injection device.
Figure 24:
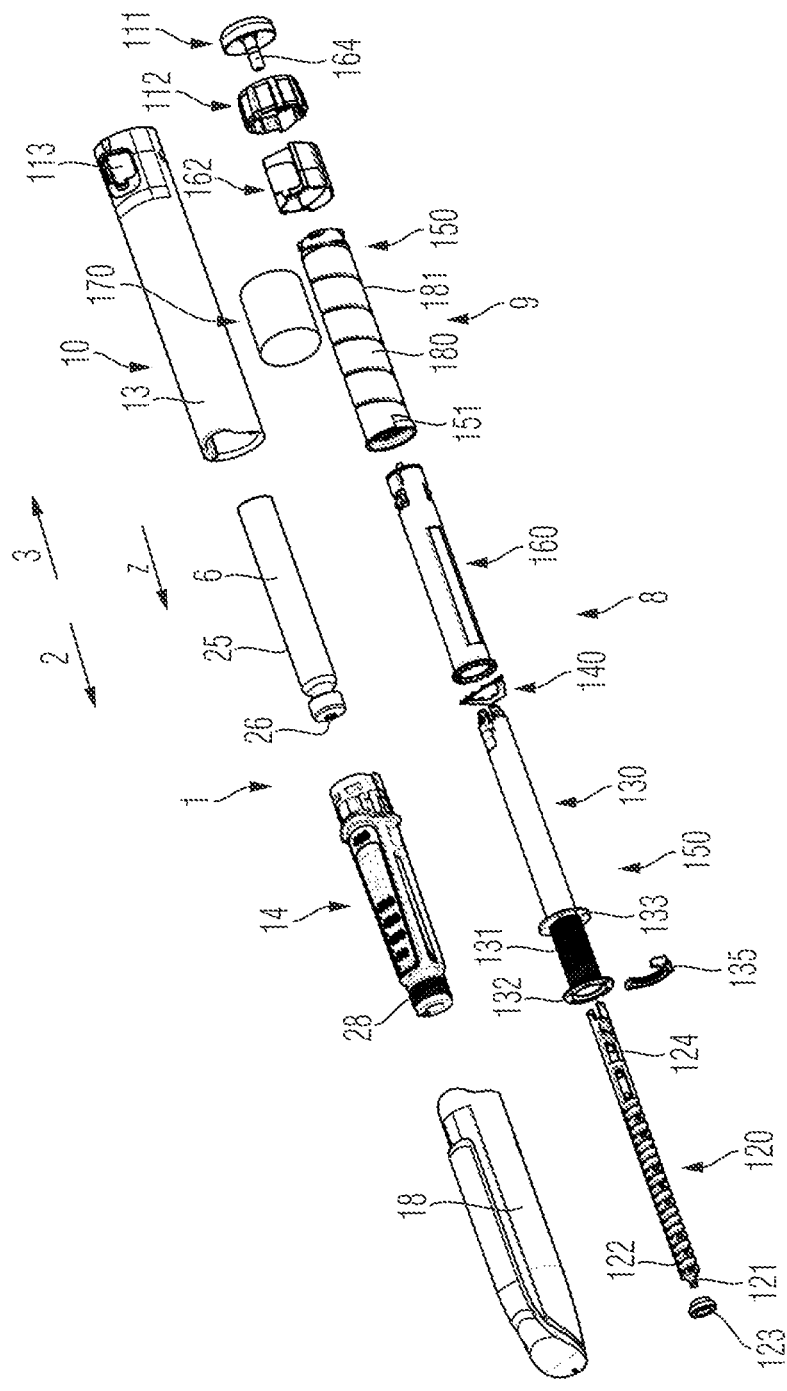
FIG. 24 shows an exploded view of components of another injection device.

The injection device 1 as shown in FIG. 24 comprises an outer structure that is similar to the structure of the device as described above in connection with FIG. 1 or FIG. 2. The injection device 1 may be configured as a pre-filled disposable injection device that comprises a housing 10 to which an injection needle 15 can be affixed. If not described otherwise, similar or identical components of the device 1 according to FIG. 24 are denoted with the like are identical reference numbers as used in connection with the injection device 1 of FIG. 1 or FIG. 2.

As shown further in FIG. 24, the housing 10 comprises a dosage window 113 that may be in the form of an aperture in the housing 10. The dosage window 113 permits a user to view a limited portion of a number sleeve 180 that is configured to move when a dose dial 112 is turned or rotated. In this way a visual indication of a currently set dose can be provided. The dose dial 112 is rotated on a helical path with respect to the housing 10 when turned during setting and/or dispensing or expelling of a dose.

The injection device 1 may be configured so that turning the dose dial 112 causes a mechanical click sound to provide acoustical feedback to a user. The number sleeve 180 mechanically interacts with a piston in the cartridge 6. When the needle 15 is stuck into a skin portion of a patient, and when the trigger 111 or injection button is pushed, the insulin dose displayed in display window 113 will be ejected from the injection device 1. When the needle 15 of the injection device 1 remains for a certain time in the skin portion after the trigger 111 is pushed, a high percentage of the dose is actually injected into the patient's body. Ejection of a dose of the medicament may also cause a mechanical click sound, which is however different from the sounds produced when using the dose dial 112.

In this embodiment, during delivery of the insulin dose, the dose dial 112 is turned to its initial position in an axial movement, that is to say without rotation, while the number sleeve 180 is rotated to return to its initial position, e.g. to display a dose of zero units.

The injection device 1 may be used for several injection processes until either the cartridge 6 is empty or the expiration date of the medicament in the injection device 1 (e.g. 28 days after the first use) is reached.

Furthermore, before using injection device 1 for the first time, it may be necessary to perform a so-called "prime shot" to remove air from the cartridge 6 and the needle 15, for instance by selecting two units of the medicament and pressing trigger 11 while holding the injection device 1 with the needle 15 upwards. For simplicity of presentation, in the following, it will be assumed that the ejected amounts substantially correspond to the injected doses, so that, for instance the amount of medicament ejected from the injection device 1 is equal to the dose received by the user.

The expelling or drive mechanism 8 as illustrated in more detail in FIG. 24 comprises numerous mechanically interacting components. A flange like support of the housing 10 comprises a threaded axial through opening threadedly engaged with a first thread or distal thread 122 of the piston rod 120. The distal end of the piston rod 120 comprises a bearing 121 on which a pressure foot 123 is free to rotate with the longitudinal axis of the piston rod 120 as an axis of rotation. The pressure foot 123 is configured to axially abut against a proximally facing thrust receiving face of the bung 7 of the cartridge 6. During a dispensing action the piston rod 120 rotates relative to the housing 10 thereby experiencing a distally directed advancing motion relative to the housing 10 and hence relative to the barrel 25 of the cartridge 6. As a consequence, the bung 7 of the cartridge 6 is displaced in distal direction 2 by a well-defined distance due to the threaded engagement of the piston rod 120 with the housing 10.

The piston rod 120 is further provided with a second thread 124 at its proximal end. The distal thread 122 and the proximal thread 124 are oppositely handed.

There is further provided a driver 130 having a hollow interior to receive the piston rod 20. The driver 130 may comprise or may form a drive sleeve. The driver 130 comprises an inner thread threadedly engaged with the proximal thread 124 of the piston rod 120. Moreover, the driver 130 comprises an outer threaded section 131 at its distal end. The threaded section 131 is axially confined between a distal flange portion 132 and another flange portion 133 located at a predefined axial distance from the distal flange portion 132. Between the two flange portions 132, 133 there is provided a last dose limiting member 135 in form of a semi-circular nut having an internal thread mating the threaded section 131 of the driver 130.

The last dose limiting member 35 further comprises a radial recess or protrusion at its outer circumference to engage with a complementary-shaped recess or protrusion at an inside of the sidewall of the housing 10. In this way the last dose limiting member 135 is splined to the housing 10. A rotation of the driver 130 in a dose incrementing direction 4 or clockwise direction during consecutive dose setting procedures leads to an accumulative axial displacement of the last dose limiting member 135 relative to the driver 130. There is further provided an annular spring 140 that is in axial abutment with a proximally facing surface of the flange portion 133. Moreover, there is provided a tubular-shaped clutch 160. At a first end the clutch 160 is provided with a series of circumferentially directed saw teeth. Towards a second opposite end of the clutch 160 there is located a radially inwardly directed flange.

The number sleeve 180 is provided outside of the spring 140 and the clutch 160 and is located radially inward of the housing 10. A helical groove 181 is provided about an outer surface of the number sleeve 180. The housing 10 is provided with the dosage window 113 through which a part of the outer surface of the number 180 can be seen. The housing 10 is further provided with a protrusion 163 or helical rib at an inside sidewall portion of an insert piece 162, which helical rib is to be seated in the helical groove 181 of the number sleeve 180. The tubular shaped insert piece 62 is inserted into the proximal end of the housing 10. It is rotationally and axially fixed to the housing 10. There may be provided first and second stops on the housing 10 to limit a dose setting procedure during which the number sleeve 180 is rotated in a helical motion relative to the housing 10. As will be explained below in greater detail, at least one of the stops is provided by a preselector stop feature 171 provided on a preselector 170.

The dose dial 112 in form of a dose dial grip is disposed about an outer surface of the proximal end of the number sleeve 180. An outer diameter of the dose dial 112 typically corresponds to and matches with the outer diameter of the housing 10. The dose dial 112 is secured to the number sleeve 180 to prevent relative movement there between. The dose dial 112 is provided with a central opening.

The trigger 111, also denoted as dose button is substantially T-shaped. It is provided at a proximal end of the injection device 10. A stem 164 of the trigger 111 extends through the opening in the dose dial 112, through an inner diameter of extensions of the driver 130 and into a receiving recess at the proximal end of the piston rod 120. The stem 164 is retained for limited axial movement in the driver 130 and against rotation with respect thereto. A head of the trigger 111 is generally circular. The trigger side wall or skirt extends from a periphery of the head and is further adapted to be seated in a proximally accessible annular recess of the dose dial 112.

To dial a dose a user rotates the dose dial 112. With the spring 140 also acting as a clicker and the clutch 160 engaged, the driver 130 the spring or clicker 140, the clutch 160 and the number sleeve 180 rotate with the dose dial 112. Audible and tactile feedback of the dose being dialed is provided by the spring 140 and by the clutch 160. Torque is transmitted through saw teeth between the spring 140 and the clutch 160. The helical groove 181 on the number sleeve 180 and a helical groove in the driver 130 have the same lead. This allows the number sleeve 180 to extend from the housing 10 and the driver 130 to climb the piston rod 120 at the same rate. At a limit of travel a radial stop on the number sleeve 180 engages either with a first stop or a second stop provided on the housing 10 provided on the pre-selector 170 to prevent further movement in a dose incrementing direction 4. A rotation of the piston rod 120 is prevented due to the opposing directions of the overall and driven threads on the piston rod 120.

The last dose limiting member 135 keyed to the housing 10 is advanced along the threaded section 131 by the rotation of the driver 130. When a final dose dispensed position is reached, a radial stop formed on a surface of the last dose limiting member 135 abuts a radial stop on the flange portion 133 of the driver 130, preventing both, the last dose limiting member 135 and the driver 130 from rotating further.

Should a user inadvertently dial beyond the desired dosage, the injection device 1, configured as a pen-injector allows the dosage to be dialed down without dispense of the medicament from the cartridge 6. For this the dose dial 112 is simply counter-rotated, in the dose decrementing direction 5. This causes the system to act in reverse. A flexible arm of the spring or clicker 140 then acts as a ratchet preventing the spring 140 from rotating. The torque transmitted through the clutch 160 causes the saw teeth to ride over one another to create the clicks corresponding to dialed dose reduction. Typically, the saw teeth are so disposed that a circumferential extent of each saw tooth corresponds to a unit dose.

When the desired dose has been dialed the user may simply dispense the set dose by depressing the trigger 111. This displaces the clutch 160 axially with respect to the number sleeve 180 causing dog teeth thereof to disengage. However, the clutch 160 remains keyed in rotation to the driver 130. The number sleeve 180 and the dose dial 112 are now free to rotate in accordance with the helical groove 181.

The axial movement deforms the flexible arm of the spring 140 to ensure the saw teeth cannot be overhauled during dispense. This prevents the driver 130 from rotating with respect to the housing 10 though it is still free to move axially with respect thereto. The deformation is subsequently used to urge the spring 140 and the clutch 160 back along the driver 130 to restore the connection between the clutch 160 and the number sleeve 180 when the distally directed dispensing pressure is removed from the trigger 111.

The longitudinal axial movement of the driver 130 causes the piston rod 120 to rotate through the through opening of the support of the housing 10, thereby to advance the bung 7 in the cartridge 6. Once the dialed dose has been dispensed, the number sleeve 180 is prevented from further rotation by contact of a plurality of members extending from the dose dial 112 with a corresponding plurality of stops. A zero dose position is finally determined by the abutment of one of axially extending edges of members of the number indicating sleeve 180 with a corresponding stop of the housing 10.

The expelling mechanism or drive mechanism 8 as described above is only exemplary for one of a plurality of differently configured drive mechanisms that are generally implementable in a disposable pen-injector. The drive mechanism as described above is explained in more detail e.g. in WO2004/078239A1, WO 2004/078240A1 or WO 2004/078241A1 the entirety of which being incorporated herein by reference.

Compared to the injection device as described in any one of the documents WO2004/078239A1, WO 2004/078240A1 or WO 2004/078241A1 the injection device according to FIGS. 24 to 47 is further provided with a preselector 170; 270, 370, 470, 570. The preselector 170 is displaceable relative to the housing 10 between at least two preselection positional states in order to define a one of a plurality of activation positions of the dose tracker or to define a maximum dose positional state of the dose tracker 150. In the example of FIG. 24 the dose tracker 150 may comprise the number sleeve 180 having a helical groove 181 that is in threaded engagement with the housing 10 or with the insert 162 that is fixed to the housing 10. Here and in the following embodiments the number sleeve 180 may represent the dose tracker 150 or may coincide with the dose tracker 150.

On an outside surface of the number sleeve 180 there may be provided consecutive numbers that show up in the dosage window 113. Selection and indication of visualization of a dose is modified with the various examples of an injection device as described hereinafter with regards to FIGS. 25 to 47. With the various examples as illustrated in FIGS. 25 to 47 the number sleeve 180 and hence by the dose tracker 150 is displaceable in unison with a trigger 111 relative to the housing 10 for setting as well as for dispensing of the dose of the medicament.

In the example of FIGS. 25 to 28 there is provided a preselector 170 that is displaceable relative to the housing 10 between at least two preselection positional states p1 and p2. Each preselection positional state p1, p2 defines a maximum dose positional state dm for the dose tracker. In the present example the preselector 170 comprises a preselector sleeve that is rotationally fixed to the tubular shaped housing 10.

As shown in FIGS. 25 to 28 the preselector 170 is provided and rotationally supported at a proximal end 142 of the housing 10. It may be rotationally supported on a side wall 13 of the housing 10. For selecting at least one of two available preselection positional states p1, p2 the preselector 170 is rotatable with regard to a rotation axis extending parallel to the longitudinal axis of the housing 10. The preselector 170 is lockable or fixable relative to the housing 10 in any one of the at least two preselection positional states p1, p2. In this way and when the preselector 170 is in a first preselection positional state p1 the preselector 170 is hindered and impeded against self-actuated displacement relative to the housing 10.

Figure 27:
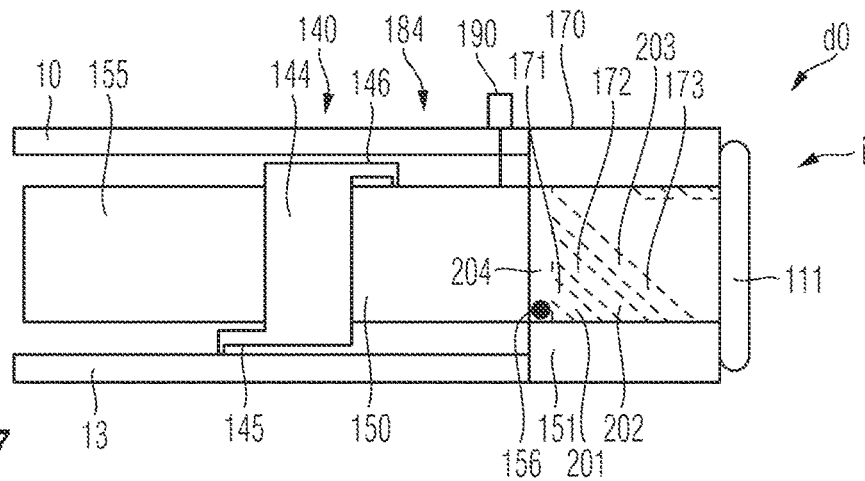
FIG. 27 shows a longitudinal cross-section of some components of the injection device according to FIG. 25.

The preselector 170 comprises a first preselector stop feature 171. The preselector stop feature 171 as illustrated in FIG. 27 comprises a first groove 201. The preselector 170 further comprises a second preselector stop feature 172. The second preselector stop feature 172 comprises a second groove 202. The grooves 201, 202 are provided on an inside facing surface of the sleeve of the preselector 170. The dose tracker 150 comprising a tracking stop feature 151. The tracking stop feature 151 comprises a radial protrusion 156 protruding radially outwardly from an outside surface of the dose tracker 150. Here, the dose tracker 150 comprises a tracking sleeve 155 that is rotationally and translationally supported inside the elongated housing 10.

Typically, the dose tracker 150 is in threaded engagement with the housing 10. As illustrated in FIG. 27 and when in the zero dose positional state the tracking stop feature 151 is located inside a connecting groove 204 interconnecting the first groove 201 and the second groove 202. One end, e.g. a first end of the first groove 201 merges into the connecting groove 204. A first end of the second groove 202 also merges into the connecting groove 204. The connecting groove 204 extends at a predefined angle relative to the elongation of the first groove 201 and the second groove 202. Typically, first and second grooves 201, 202 extend parallel to each other. As illustrated, the second groove 202 comprises a larger longitudinal extension compared to the first groove 201. There is also provided a third groove 203. Also the third groove 203 extends parallel to the first groove 201 and to the second groove 202. The third groove 203 comprises an elongation that is larger than the elongation of the second groove 202. As shown further, the second groove 202 is located between the first groove 201 and the third groove 203.

Figure 25:
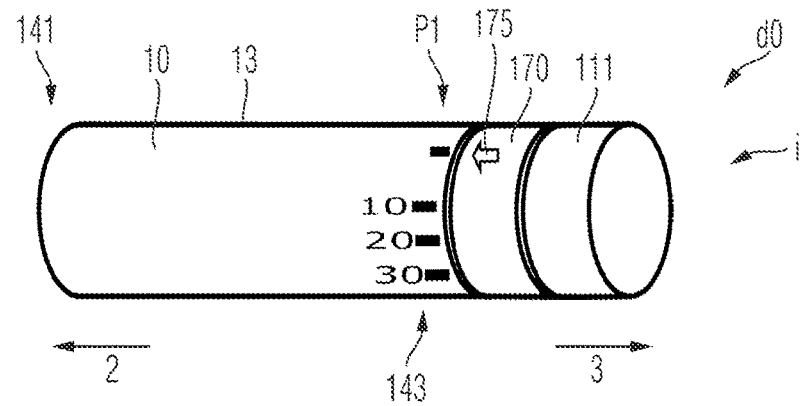
FIG. 25 is an exemplary and simplified illustration of the injection device of FIG. 24 with the dose tracker in the initial position.
Figure 26:
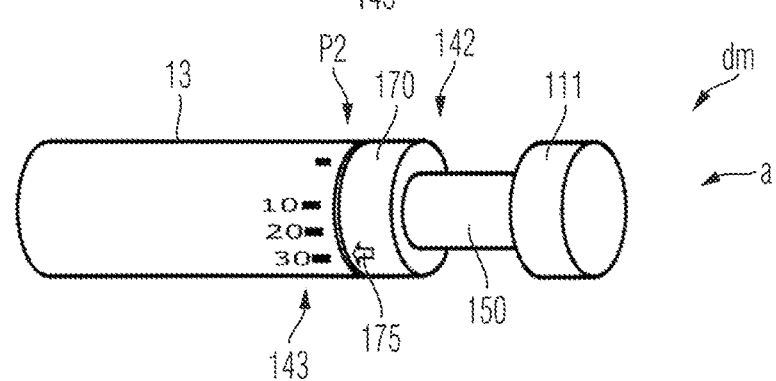
FIG. 26 is indicative of the device according to FIG. 25 with the dose tracker in an activated position.

The connecting groove 204 comprises an elongation that aligns with and/or coincides with a direction of displacement of the preselector 170 when the preselector 170 is displaced between the at least two preselection positional states p1, p2. For transferring and displacing the preselector 170 from the first preselection positional state p1 as illustrated in FIG. 25 to the second preselection positional state p2 as illustrated in FIG. 26 the preselector 170 is rotatable relative to the housing 10, e.g. in a counterclockwise direction. Accordingly, the connecting groove 204 extends in circumferential or tangential direction with regards to the tubular shaped housing 10 or with regards to the tubular shaped preselector 170.

As further illustrated in FIGS. 25 and 26 the housing 10, in particular the sidewall 13 thereof is provided with a preselection indication 143. The preselection indication 143 comprises numerous numbers or symbols arranged along a displacement path of the preselector 170. The preselector 170 comprises a correspondingly shaped preselection indication 175, e.g. in form of an arrow. In each one of the provided preselection positional states p1, p2 the preselection indication 175 of the preselector 170 aligns with one of the preselection indications 143 of the housing 10.

An alternative implementation is also conceivable here, wherein the preselection indication 143 comprises a pointer or an arrow and wherein the preselection indication 175 comprises numerous numbers or symbols arranged along a displacement path of the preselector 170. The preselection indication 175 aligning with a preselection indication 143 indicates to the user, which one of the preselection positional states p1, p2 is actually valid for the injection device 1. In the present example there may be provided three or even for preselection positional states. In a first preselection positional state the tracking stop feature 151 is in alignment with the first groove 201. In a second preselection positional state the tracking stop member 151 is in alignment with the second groove 202.

There is also provided an interlock 184. The interlock 184 is connected to one of the housing 10 and the dose tracker 150. The interlock 184 is further connectable to the other one of the housing and the dose tracker in order to establish a releasable engagement between the dose tracker 150 and housing 10. The interlock 184 may further comprise or may be operably engaged with a release member 190. The release member 190 is configured to release the interlock 184 in order to liberate and to enable a movement of the dose tracker 150 relative to the housing 10. The interaction of the interlock 184 and the release member 190 is such that the dose tracker 150 it locked to the housing 10 when in the initial position i or in the zero dose positional state d0 as illustrated in FIG. 27. In the present example there is further provided a mechanical energy reservoir in form of a spring 144. The spring 144 comprises a first end 145 connected to the housing 10 and the spring 144 comprises a second end 146 connected to the dose tracker 150. If the release member 190 is actuated in order to liberate or to release the dose tracker 150 the dose tracker 150 starts to rotate relative to the housing 10 under the action of the relaxing spring 144.

As illustrated the spring 144 comprises a cylindrically wound torsion spring 147. The spring 144 encloses at least a portion of an outside surface of the tracking sleeve 155 of the dose tracker 150. In this way and when released the spring 144 is configured to induce a torque to the dose tracker 150.

Figure 28:
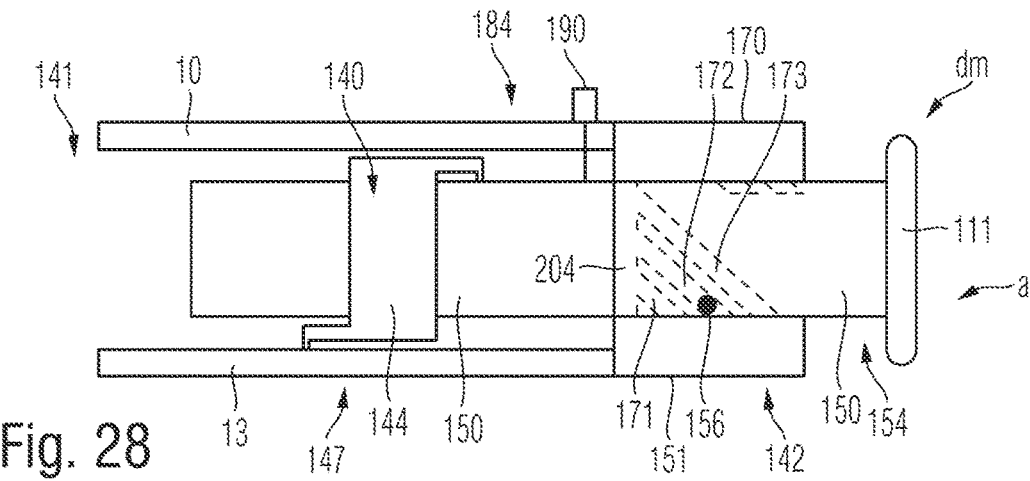
FIG. 28 shows a longitudinal cross-section of some components of the device according to FIG. 26.

In the given preselection positional state p1, p2 the preselector 170 is rotationally fixed to the housing 10. Here, the engagement of the tracking stop feature 151 with one of the grooves 201, 202, 203 provides a threaded engagement between the dose tracker 150 and the housing 10. Since the preselector 170 is translationally or axially fixed to the housing 10 the dose tracker 150 is subject to a proximally directed displacement such that a proximal end 154 of the dose tracker 150 protrudes from a proximal end of the preselector 170 and/or from a proximal end 142 of the housing 10 when reaching the maximum dose positional state dm as illustrated in FIG. 28.

The amount of displacement of the length of a displacement path of the dose tracker 150 relative to the housing 10 is indicative and is directly correlated to the size of a dose actually set. The grooves 201, 202, 203 each comprise a second end facing away from the connecting groove 204. The second end of the grooves 201, 202, 203 each provides an end stop for the tracking stop feature 151. At the second end each one of the grooves 201, 202, 203 comprises a stop face to engage or to abut with a correspondingly shaped stop face of the protrusion 156 of the tracking stop feature 151. Once the tracking stop feature 151 with its protrusion 156 reaches the second end of the second groove 202 as illustrated in FIG. 26 or 28 a further displacement of the dose tracker 150 in a dose incrementing direction, i.e. proximal direction, relative to the preselector 170 and/or relative to the housing 10 is effectively impeded and blocked.

Once the maximum dose positional state dm has reached the injection device 1 is prepared and ready for a dose dispensing procedure. For this, a user has to depress the trigger 111 in distal direction as described above with regard to FIG. 24. During a dispensing procedure the dose tracker 150 returns into the initial position i and hence back into the zero dose positional state d0. It rotates in a dose decrementing direction 5 relative to the housing 1 in accordance and along the helical path provided by the respective grooves 201, 202, 203. When reaching the initial position i as illustrated in FIGS. 25 and 27 the interlock 184 reengages and positionally fixes the dose tracker 150 to the housing 10.

Thereafter the preselector 170 may the transferred to another preselection positional state in order to vary the size of the dose if required. Otherwise, the preselector 170 remains in the present preselection positional state. A repeated actuation of the release member 190 will lead to a release of the interlock 184 thus enabling a further automated displacement of the dose tracker 150 from the initial position i to the activation position a. Accordingly, another dispensing procedure can take place.

In the example of FIGS. 25 to 28 the dose tracker 150 may be in threaded engagement with the housing 10 only via the tracking stop feature 151 sliding along the preselector stop feature 171 of the preselector 170. It is generally conceivable, that the insert 162 as described in connection with FIG. 24 is replaced by the preselector 170. In this way, only minor modifications have to be implemented in the injection device 1 as described in any of the documents WO2004/078239A1, WO 2004/078240A1 or WO 2004/078241A1 in order to implement a preselection of only a limited number of different dose sizes.

Figure 29:
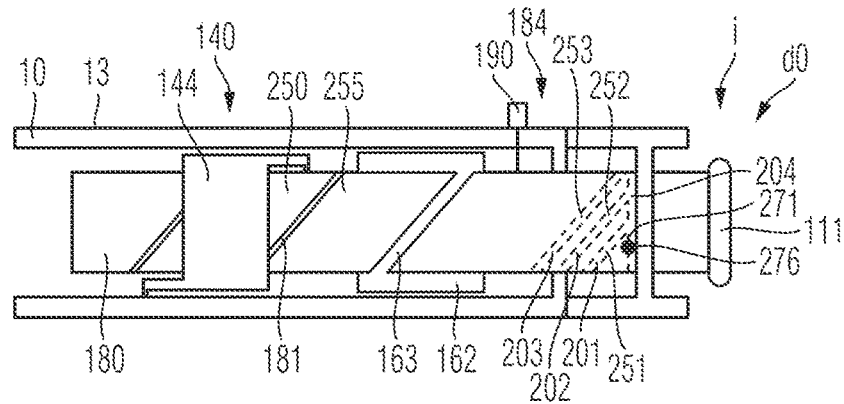
FIG. 29 is illustrative of a longitudinal cross-section of another example of an injection device according to FIG. 25.
Figure 30:
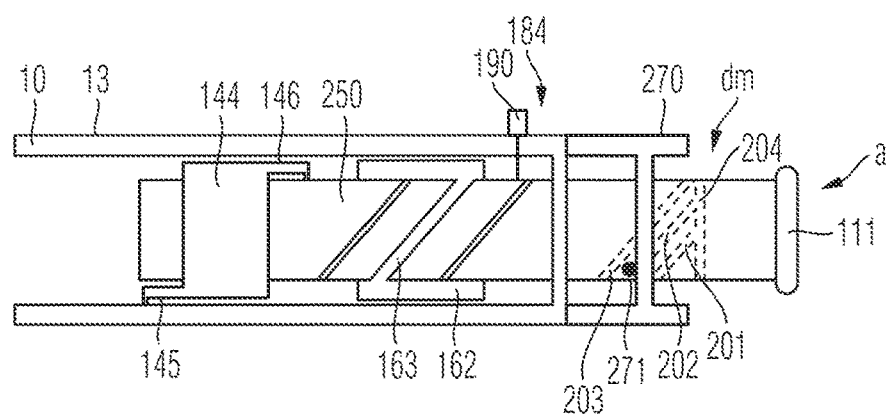
FIG. 30 shows the injection device of FIG. 29 with the dose tracker in the maximum dose positional state.

In FIGS. 29 and 30 another example of an injection device 1 is illustrated. Identical or components compared to the example of FIGS. 25 to 28 are denoted with identical reference numbers. Similar components compared to the example of FIGS. 25 to 28 are denoted with respective reference numbers that are increased by 100.

In comparison to the example of FIGS. 27 and 28 the example of FIGS. 29 and 30 comprises an insert 162 that is fixed to the housing 10. The insert 162 is typically fixed to a sidewall 13 of the housing 10. The insert 162 is a threaded insert. The insert 162 comprises a radially inwardly extending protrusion 163. The protrusion 163 may comprise a helical shape. It may be in threaded engagement with an outer thread or with a helical groove 181 on the outside surface of the dose tracker 250. Also here, the dose tracker 250 may coincide with a number sleeve 180. The preselector 270 is of sleeve-like shape. It is rotationally supported at or near a proximal end of the housing 10. The preselector 270 is axially or longitudinally fixed to the housing 10.

The preselector 270 comprises a preselector stop feature 271. The dose tracker 250 comprises a correspondingly shaped tracking stop feature 251. Compared to the example of FIGS. 27 and 28 it is the tracking stop feature 251 that comprises a first tracking stop feature 151 comprising a first groove 201, a second tracking stop feature 152 comprising a second groove 202 and a third tracking stop feature 153 comprising a third groove 203. The grooves 201, 202, 203 are connected by a connecting groove 204 in the same way as described above in connection with FIGS. 25 to 28. The preselector stop feature 171 comprises a radial protrusion 176 that is in sliding engagement with one of the grooves 201, 202, 203, 204.

Figure 28A:
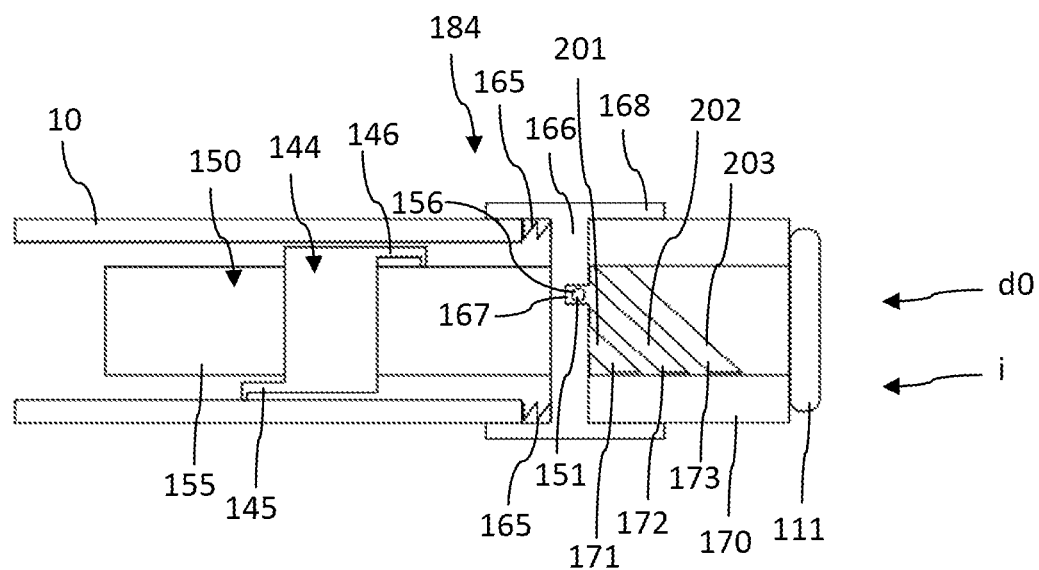
FIG. 28a shows a longitudinal cross-section of a modification of the device according to FIG. 26.
Figure 28B:
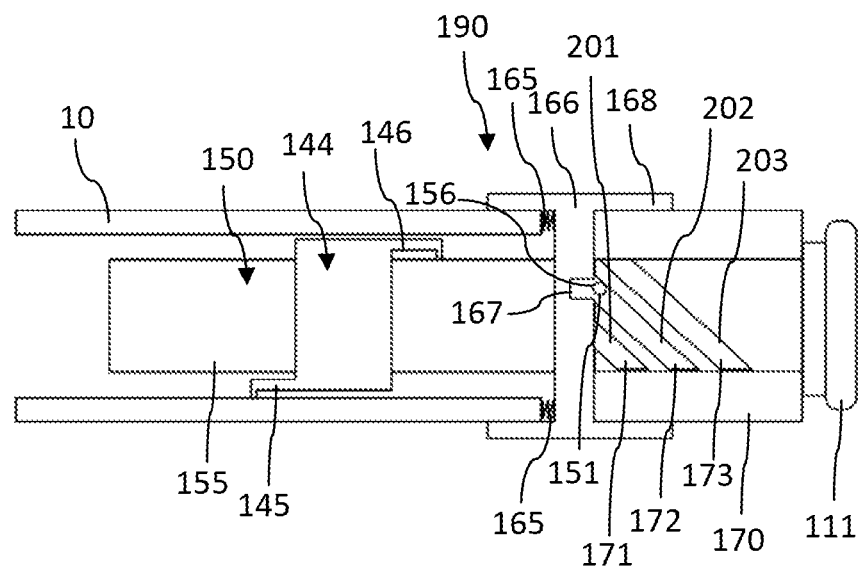
FIG. 28b shows a longitudinal cross-section of the device of FIG. 28a with the clutch and the preselector shifted in distal direction.

In FIGS. 28a and 28b a modification of the device as illustrated in FIGS. 25 to 28 is illustrated. Here, the injection device is equipped with a supplemental clutch 166 having a recess 167 to engage with the protrusion 156 and hence with the tracking stop feature 151 of the dose tracker 150. The supplemental clutch 166 may comprise a clutch sleeve. The supplemental clutch 166 may comprise a tubular shaped body with a tubular-shaped sidewall 168. The clutch 166 is attached to the housing 10. It may be located on an outside surface of the housing 10. It may be displaceable in longitudinal direction relative to the housing 10. The clutch 166 is rotationally fixed to the housing 10. The clutch 166 may be in a splined engagement with the housing 10. Hence, the clutch 166 is hindered to rotate relative to the housing 10. The clutch 166 may be in a longitudinally sliding and rotation inhibiting engagement with the housing 10.

In the zero dose positional state d0 of the dose tracker 150 as illustrated in FIG. 28a the tracking stop feature 151 of the dose tracker 150 and hence the protrusion 156 is located inside the recess 167 of the clutch 166. The recess 167 comprises a tangential or circumferential width that substantially matches with the respective size or width of the protrusion 156. The width or size of the recess 167 may be slightly larger than the size of the protrusion so as to enable a smooth insertion of the protrusion 156 into the recess 167. The recess 167 is open towards the proximal direction 3.

The clutch 166 is axially displaceable in distal direction 2 against the action of a spring 165. One end of the spring 165 is engaged with the clutch 166 and the opposite end of the spring 165 is engaged with the housing 10. The spring 165 may comprise a compression spring. It may be configured to urge or to drive the clutch 166 in and towards the proximal direction 3. As long as the protrusion 156 is located inside the recess 167 the mutual engagement of the protrusion 156 and the recess 167 hinders the dose tracker 150 from rotating under the action of the spring 144.

The position of the recess 167 matches and overlaps with the position of the protrusion 156 as the dose tracker 150 is in the zero dose positional state d0. By depressing the clutch 166 in distal direction the recess 167 is moved in distal direction accordingly. As a consequence, the protrusion 156 is no longer retained inside the recess 167 and the dose tracker 150 becomes free to rotate under the action of the spring 144.

The preselector 170 is axially engaged with the clutch 166. It is fixed to the clutch 166 in axial or longitudinal direction. Any movement of the clutch 166 in longitudinal or axial direction equally transfers to a respective movement of the preselector 170. The preselector 170 is rotatable relative to the clutch 166. In any of its rotational states, the preselector 170 is rotationally fixable to the clutch and hence to the housing 10. The preselector 170 may be in a kind of a snap-fit engagement or ratchet engagement with the housing 10 or with the clutch 166. This allows and supports a dedicated rotation of the preselector 170 with the longitudinal axis of the injection device as an axis of rotation, so as to bring one of the preselector stop features 171, 172, 173 in axial or longitudinal alignment with the tracking stop feature 151 as the tracking stop feature is in the zero dose positional state. The rotation of the preselector 170 relative to the housing 10 and/or relative to the clutch 166 may be accompanied by an audible click sound or haptic feedback.

When in the zero dose positional state d0 the preselector 170 is rotatable relative to the housing 10 as well as relative to the clutch 166 in order to preselect a dose of a particular size. For instance and as illustrated in FIG. 28a the second preselector stop feature 172 and hence the groove 202, in particular the distal end of the preselector stop feature 172 and the distal end of the groove 202, are brought in longitudinal alignment with the recess 167 and hence with the protrusion 156 or tracking stop feature 151 located therein.

Since the preselector 170 is axially connected to the clutch 166, a distally directed displacement of the clutch 166 equally transfers to a respective distally directed displacement of the preselector 170; and vice versa. As a consequence, the tracking stop feature 151 and hence the protrusion 156 slides out of the recess 167 and enters the preselector stop feature 172, i.e. the groove 202. Through this axial displacement of the preselector 170 relative to the housing 10 the protrusion 156 enters the groove 202. The protrusion 156 is then allowed to slide along the helical path provided by the groove 202. In this way the entire dose tracker 150 becomes subject to a proximally directed screwing motion relative to the housing 10 as it is free to rotate under the action of the spring 144 as described above in connection with FIGS. 25 to 28.

At the end of a dose delivery procedure during which the dose tracker 150 is moved in distal direction 2 and during which the dose tracker 150 returns into the zero dose positional state d0 the tracking stop feature 151 and hence the protrusion 156 re-enters the recess 167. As the dose dispensing or injection procedure terminates the mutual engagement of the tracking stop feature 151 or protrusion 156 with the recess 167 hinders the dose tracker 150 from rotating.

In the example of FIGS. 28a and 28b the release member 190 may be replaced by the clutch 166. Here, the clutch 166 may provide both, an interlock 184 as well as a release member 190. In the proximal position as indicated in FIG. 28a the clutch 166 provides an interlock 184 configured to prevent a rotation of the dose tracker 150 relative to the housing 10. In the distal position as indicated in FIG. 28b the clutch 166 provides a release member 190 disengaging the interlock 184, thus allowing and supporting a rotation of the dose tracker 150 relative to the housing 10.

The clutch 166 as illustrated in FIGS. 28a and 28b may be integrally formed with the clutch 160 as illustrated in FIG. 24. The clutch 166 may be a portion of the clutch 160. In further examples the clutch 166 and the clutch 160 may be separate parts.

In the initial position i as illustrated in FIG. 29 the preselector stop feature 271 is slidably engaged with the connecting groove 204. A rotation of the preselector 270 relative to the housing 10 provides an alignment of the preselector stop feature 271 with one of the grooves 201, 202, 203. After a release of the dose tracker 250 by actuating the release member 190 the dose tracker 250 starts to rotate according to the threaded engagement with the insert 162 relative to the housing 10 and hence relative to the preselector 170, which is rotationally fixed to the housing 10 in the respective preselection positional state.

As illustrated in FIG. 30 the preselector stop feature 171, in particular a radially inwardly extending protrusion 176 as provided on an inside facing sidewall of the sleeve-shaped preselector 170 slides along the groove 202 until it reaches a second end of the groove 202 provided with a stop face for the preselector stop feature 171. In this maximum dose positional state dm any further proximally directed displacement of the dose tracker 150 is blocked through the mutual engagement of the protrusion 176 with the second end of the groove 202. The mode of operation of the device according to FIGS. 29 and 30 is comparable if not identical to the mode of operation as described in connection with the device according to FIGS. 25 to 28.

Figure 31:
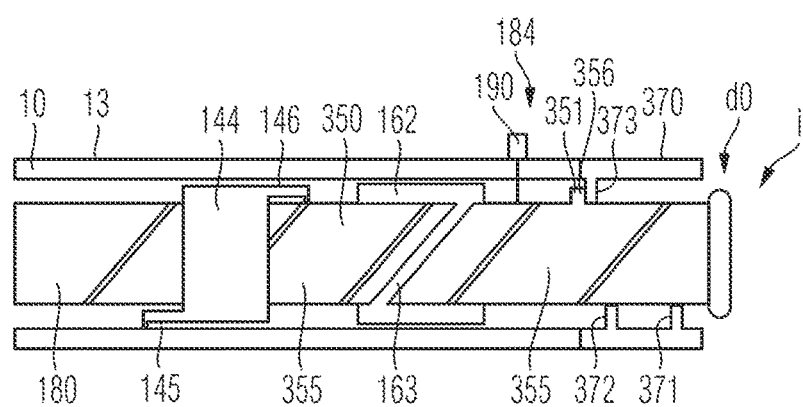
FIG. 31 shows a further example of an injection device with the dose tracker in the zero dose positional state.
Figure 32:
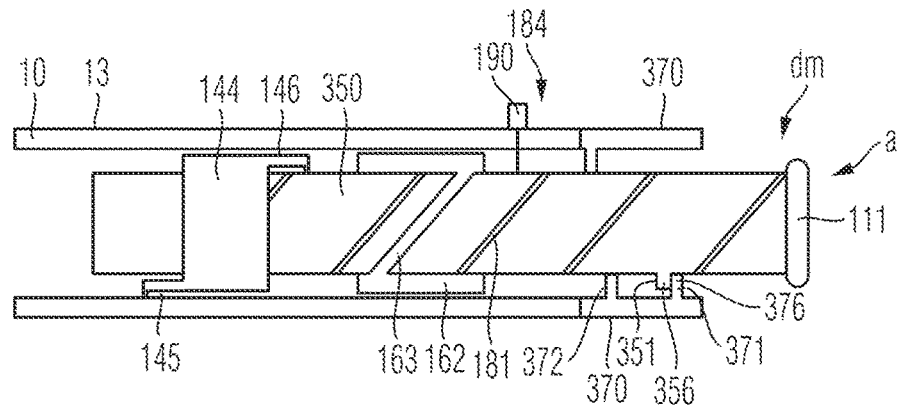
FIG. 32 shows the device according to FIG. 31 with the dose tracker in the maximum dose positional state.
Figure 33:
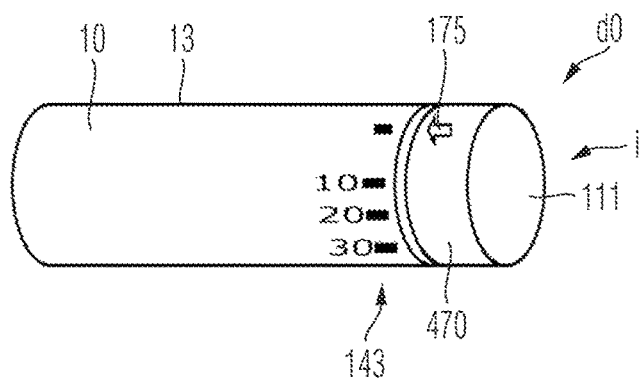
FIG. 33 is a further illustration of an injection device, wherein the preselector is translationally locked to the dose tracker.
Figure 34:
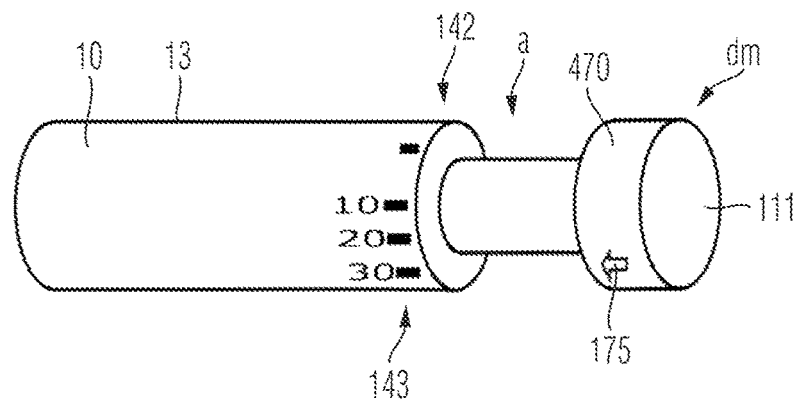
FIG. 34 shows the injection device according to FIG. 33 with the dose tracker in the maximum dose positional state.

The further example of FIGS. 31 and 32 is somehow similar to the example as described in connection with FIGS. 29 and 30. Also here the dose tracker 350 comprises a tracking stop feature 351. The dose tracker 350 comprises a tracking sleeve 355 that is in threaded engagement with the insert 162. Also here, the preselector 370 is of sleeve-like shape. It is also longitudinally or axially fixed to the housing 10, in particular to a sidewall 13 thereof. The preselector 370 is stationary supported on the housing 10 or relative to the housing between at least two preselection positional states p1, p2.

The preselector 370 comprises a first preselector stop feature 371, which is implemented as a radial protrusion 276 protruding radially inwardly from a sidewall of the preselector 270. The correspondingly shaped tracking stop feature 351 of the dose tracker 350 is provided on an outside surface portion of the tracking sleeve 355. The tracking stop feature 351 comprises a radially outwardly extending protrusion 356. For setting of a dose and for transferring the dose tracker 350 from the initial position i or from the zero dose positional state d0 to the activation position a or to the maximum dose positional state dm the dose tracker 350 rotates in accordance to the threaded engagement with the housing 10.

The preselection positional state of the preselector 370, hence the orientation of the preselector 370 with regard to a rotation axis thereof defines the positional state, hence the longitudinal position and/or an orientation of the dose tracker 350 relative to the housing 10 at least when the tracking stop feature 351 abuts with the preselector stop feature 371. As illustrated in FIGS. 31 and 32 the preselector 370 may comprise numerous preselector stop features 371, 372 and 373, hence a first preselector stop feature 371, a second preselector stop feature 372 and a third preselector stop feature 373. The various preselector stop features 371, 372, 373 all comprise a radially inwardly extending protrusion 376. The various preselector stop features 371, 372, 373 are located at a predefined positions at an inside facing sidewall portion of the preselector 370. The first and the second preselector stop features 371, 372 may be located at least one of axially and tangentially offset relative to each other.

The preselector stop features 371, 372, 373 are located at a predefined and different axial and/or longitudinal positions along the elongation or along the inner circumference of the preselector 370. The preselector stop features 371, 372, 373 may comprise a flange protruding radially inwardly from the sidewall of the preselector 370. The tangential or circumferential extension of the flange may be larger than the tangential or circumferential extent of the correspondingly shaped tracking stop feature 351. The tangential or circumferential extension of the preselector stop features 371, 372, 373 is shorter than 180°, shorter than 90° or shorter than 45° with respect to the inner circumference of the preselector 370.

In this way and depending on the rotational state of the preselector 370 the tracking stop feature 351 may pass by at least one of the preselector stop features 373 and 372 on its way towards the maximum dose positional state. When reaching the maximum dose positional state the tracking stop feature 351 axially and/or tangentially engages with that one of the preselector stop features, which, due to the positional state p1, p2 of the preselector 370 is in alignment with the tracking stop feature 351.

With the further example according to FIG. 33 to FIG. 36 the preselector 470 is permanently translationally fixed to the dose tracker 450. The preselector 470 is rotatable relative to the dose tracker 450. As already described above in connection with FIG. 29 to FIG. 32 the dose tracker 450 is threadedly engaged with the housing 10, e.g. via the threaded insert 162. Also here, a spring 144 in form of a torsion spring 147 is provided in order to provide an automated displacement of the dose tracker 450 from the initial position i towards and into the activation position a.

In the initial position i the dose tracker 450 is positionally locked to the housing 10 by means of the interlock 184 and the release member 190. In the illustrated example the preselector 470 comprises a sleeve having an inside facing surface that faces towards the outside facing surface of the sidewall 13 of the housing 10. Hence, the preselector 470 comprises a cup-shaped receptacle to receive a proximal end 142 of the housing 10. Other configurations are also conceivable, wherein at least a distal end of the preselector 470 is insertable into the sleeve-shaped housing 10.

Figure 36:
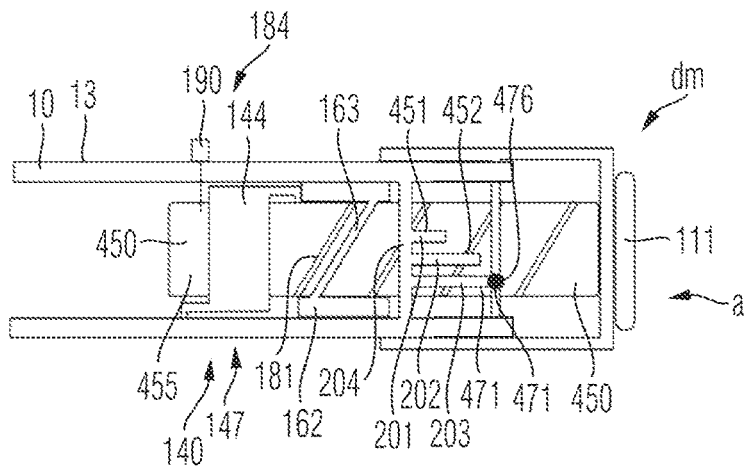
FIG. 36 shows a longitudinal cross-section of the device according to FIG. 34.

In the example as shown in FIGS. 15 and 36 the preselector stop feature 471 provided on the preselector 470 comprises a radially inwardly extending protrusion 476 to engage with the tracking stop feature 451. In contrast to the examples as described above the tracking stop feature 451 is provided on the sidewall 13 of the housing 10. The tracking stop feature 451 is provided on an outside surface of the sidewall 13. There is provided a first tracking stop feature 451, a second tracking stop feature 452 and a third tracking stop feature 453. The first tracking stop feature 451 comprises a first groove 201, the second tracking stop feature 452 comprises a second groove 202 and the third tracking stop feature comprises a third groove 203. All three grooves 201, 202, 203 merge into a connecting groove 204 with a first end. The grooves 201, 202, 204 comprise different elongations. The grooves 201, 202, 203 extend parallel to each other. The second ends of the grooves 201, 202, 203 are located at a longitudinal offset relative to each other. At their second ends the grooves 201, 202, 203 each comprise a stop face to abut or to engage with a correspondingly shaped stop face of the protrusion 476 of the preselector stop feature 471.

In this way the elongation of the grooves 201, 202, 203 define the maximum dose positional dm of the dose tracker 450. Depending on the positional state of the preselector 470 one of the grooves 201, 202, 203 aligns with the tracking stop feature 451 thereby defining the maximum distance the dose tracker 450 can move towards the proximal direction 3 when the interlock 184 is released. The tracking stop feature 451 is provided on or in an outside facing surface portion of the sidewall 13 of the housing 10.

Figure 35:
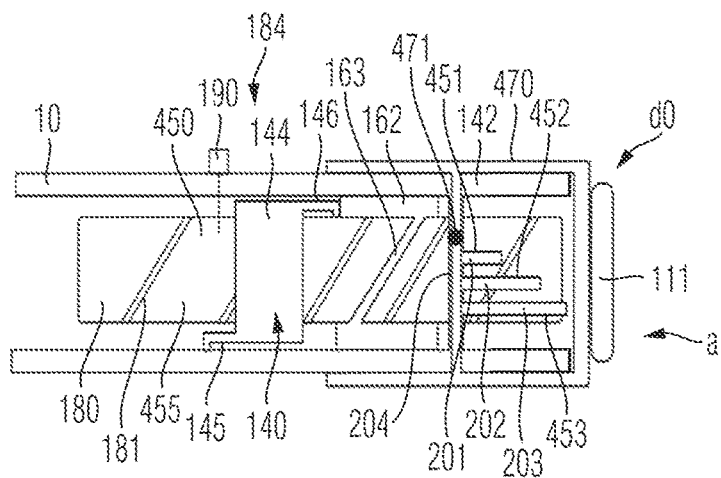
FIG. 35 shows a longitudinal cross-section through the device according to FIG. 33.

The preselector stop feature 471 protruding radially inwardly from an inside facing section of the sidewall of the preselector 470 is in permanent engagement with at least one of the grooves 201, 202, 203, 204. In the zero dose positional state d0 is illustrated in FIG. 35 the preselector stop feature 471, hence the radial protrusion 476, is located inside the connecting groove 204. By rotating the preselector 470 relative to the housing 10 the preselector stop feature 471 will be aligned with one of the grooves 201, 202, 203. Thereafter and upon releasing of the dose tracker 450 by actuation of the release member 190 the spring 144 induces a rotation of the dose tracker 450, which according to the threaded engagement with the housing 10 is subject to a helical motion relative to the housing 10.

The grooves 201, 202, 203 extend parallel to the elongation of the housing 10. They extend e.g. perpendicular to the elongation of the connecting groove 204. Since the preselector 470 is freely rotatable relative to the dose tracker 450 but remains axially and longitudinally locked and constrained to the dose tracker 450, the preselector stop feature 471 starts to slide along the selected groove 203 as soon as the dose tracker is subject to a longitudinal movement relative to the housing 10.

The engagement of the preselector stop feature 471 with the groove 203 also prevents a rotation of the preselector 470 relative to the housing 10 during a dose setting motion of the dose tracker 450. When reaching the maximum dose positional state dm, the preselector stop feature 470 gets in abutment with the second end of the groove 203 by way of which a further proximally directed displacement of the preselector 470 is impeded. Due to the permanent longitudinal interlock or engagement between the preselector 470 and the dose tracker 450 any further rotation of the dose tracker 450 is impeded and prevented.

Since the dose tracker 450 is threadedly engaged with the housing 10 any further rotation thereof would require a further displacement in longitudinal direction relative to the housing 10. This is effectively blocked an impeded when the dose tracker 450 is in the maximum dose positional state dm. In the maximum dose positional state dm as illustrated in FIG. 36 the trigger 111 can be depressed in order to induce a dose dispensing procedure as described above.

Generally, the preselector 470 may be fixed in the preselection positional states at discrete positions relative to the housing or relative to the dose tracker 450. The supported preselection states may correspond to consecutive and complete revolutions of the dose tracker 450. In the present example the dose tracker 450 comprises two or even three tracking stop features 451, 452, 453 to engage with the preselector stop feature 471. Alternatively, also the preselector 470 may comprise two or more preselector stop features to engage with the tracking stop feature 451, 452, 453. In this way the maximum dose positional state could be assigned with every half or every third revolution of the dose tracker 450 relative to the housing 10. Furthermore it is conceivable, that two or more tracking stop features 451, 452, 453 simultaneously engage with correspondingly shaped two or more preselector stop features 471. In this way the mechanical interaction and robustness of the abutment between the dose tracker 450 and the preselector 470 can be enhanced and increased.

Figure 37:
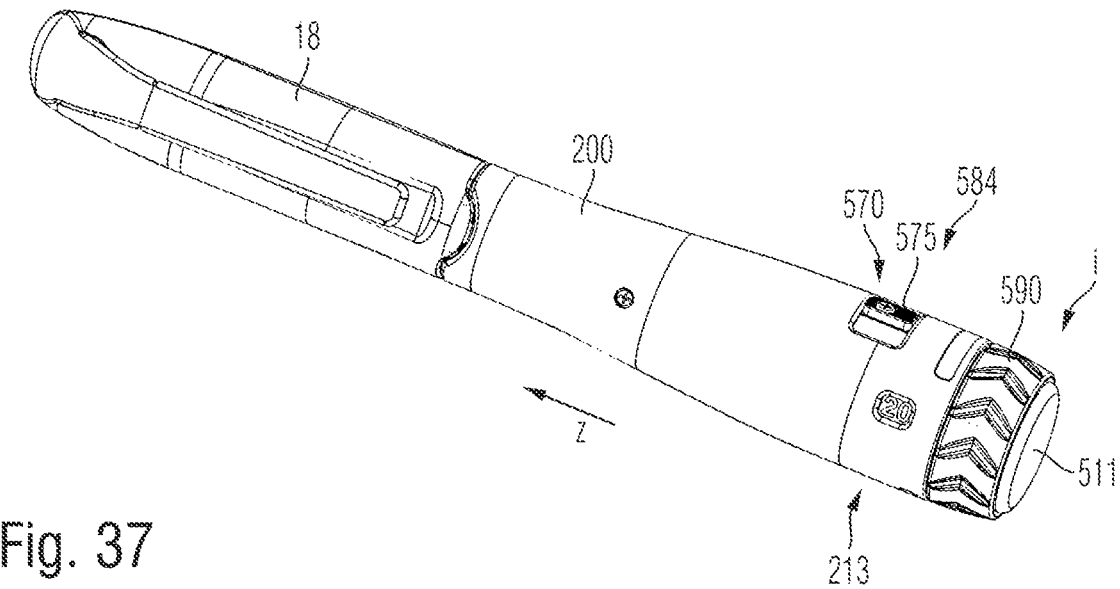
FIG. 37 is a perspective view of a further example of an injection device comprising a dose tracker and a preselector.
Figure 38:
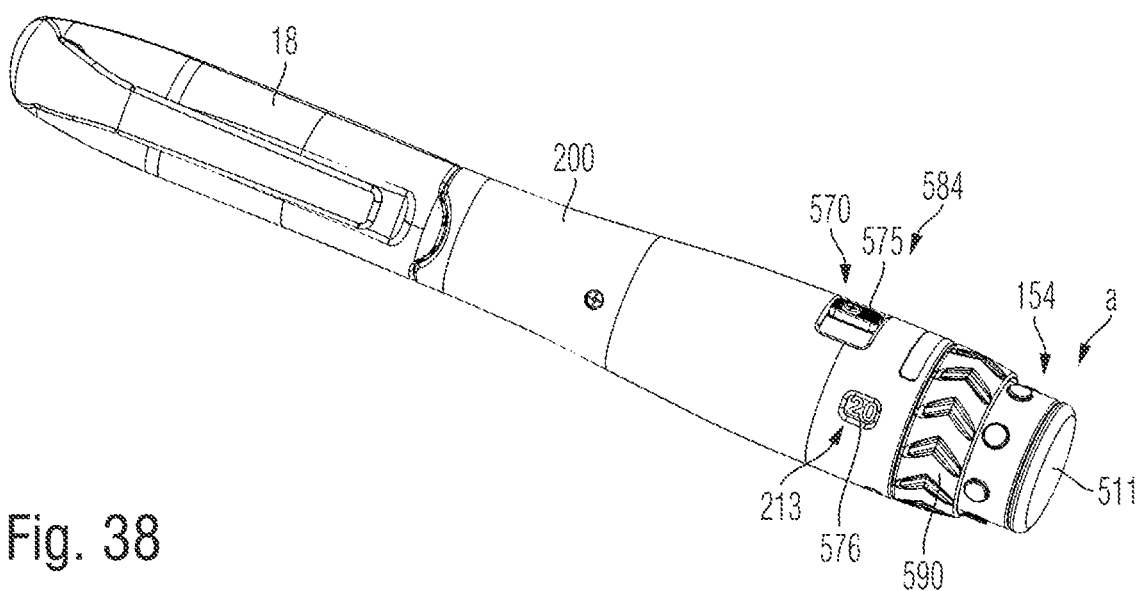
FIG. 38 shows the injection device according to FIG. 37 with the dose tracker in the activation position.

In the further example of an injection device according to FIG. 37 to FIG. 47 the injection device 1 as illustrated in FIG. 24 serves as a basis. The injection device 24 as shown in FIG. 37 comprises some additional features as will be explained below in order to provide an enhanced functionality of the injection device 1 as described above.

Figure 40:
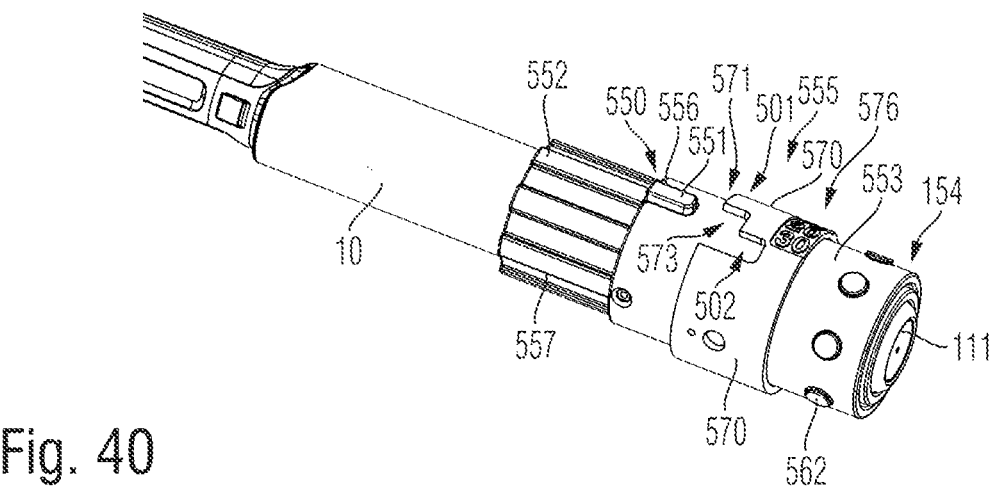
FIG. 40 shows the injection device according to FIG. 39 with the preselector.

As illustrated, there is provided an outer housing 200 encapsulating or accommodating the entirety of the housing 10 of the injection device 1. On the outside of the housing 10 there is provided the dose tracker 550. The dose tracker 550 as illustrated in FIG. 40 comprises two components, namely a distal part 552 and a proximal part 553. The distal part 552 and the proximal part 553 may be provided as a single-pieced or as an integrally shaped dose tracker 550. Only for reasons of assembly of the injection device 1 the dose tracker 550 is separated into two separate components.

The distal part 552 and the proximal part 553 are permanently and rigidly connected to each other. They are locked with regards to the longitudinal direction (z) as well as with regard to a rotation relative to the housing 10. A longitudinal displacement or rotational displacement of one of the distal part 552 and the proximal part 553 equally transfers to the other one of the distal part 552 at the proximal part 553.

In the present example the distal part 552 comprises an at least one or more elongated ribs 557 extending in longitudinal direction. The ribs 557 provide a keyed and longitudinally sliding engagement with the outer housing 200. The outer housing 200 may comprise a correspondingly shaped longitudinal groove 107 in which the rib or ribs 557 are slidably guided. The dose tracker 550 is rotationally locked to the outer housing 200 but is translationally displaceable relative to the housing 100 in longitudinal or axial direction (z). The dose tracker 550 also comprises a tracking sleeve 555 and a tracking stop feature 551.

Figure 46:
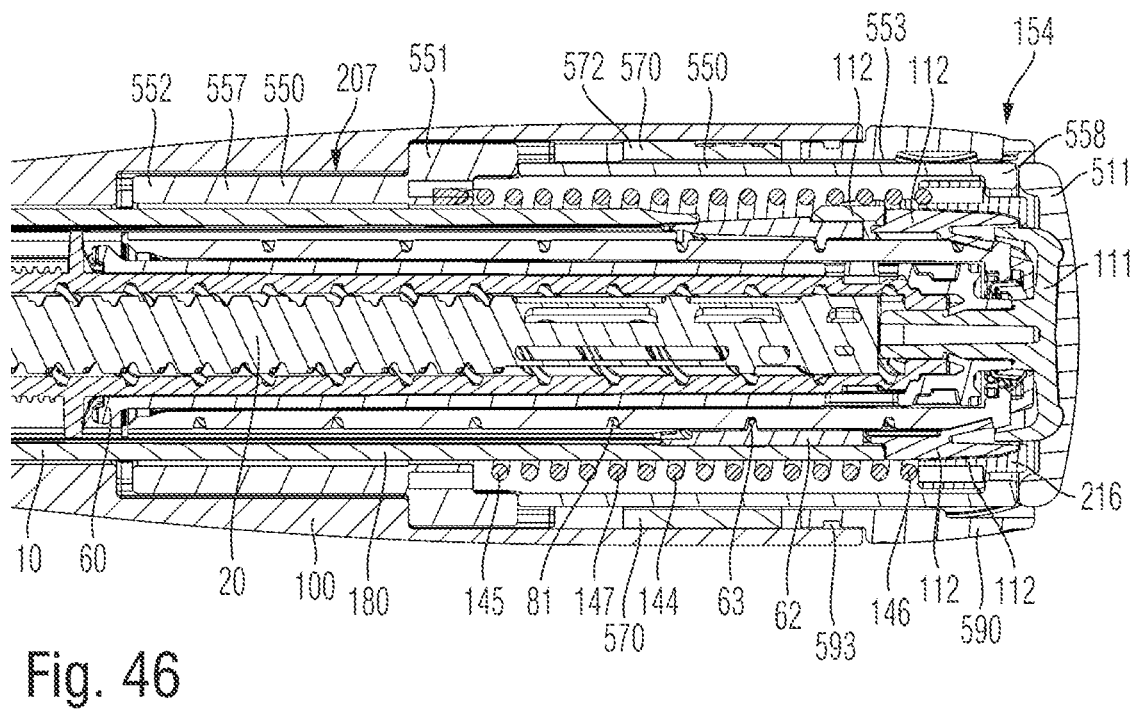
FIG. 46 is a longitudinal cross-section through the device according to FIG. 37.
Figure 47:
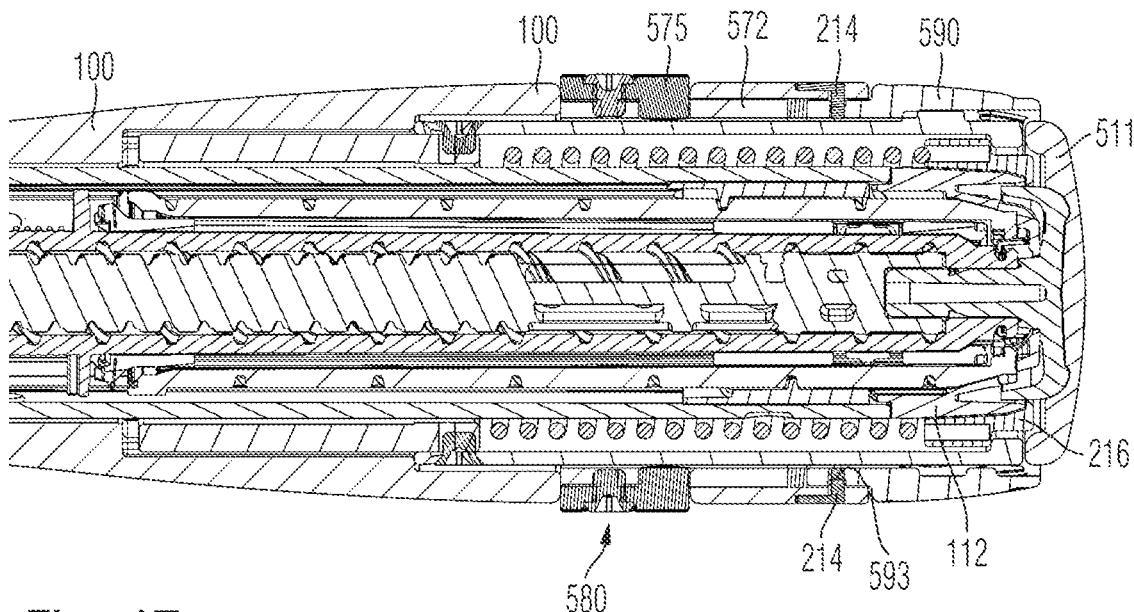
FIG. 47 is illustrative of a further longitudinal cross-section through the device of FIG. 37 rotated by 90° with regards to a longitudinal axis of the injection device.

As further illustrated in FIG. 40, there is provided a preselector 570 with a preselector stop feature 571. The preselector 570 comprises a sleeve rotationally supported on an outside facing surface of the dose tracker 550. Typically, the distal part 552 and the proximal part 553 of the tracking sleeve 555 are of tubular shape. As illustrated in FIGS. 40, 46, and 47 a proximal portion of the distal part 552 is received in a receptacle at a distal portion of the proximal part 553. In the overlapping region the distal part 552 of the proximal part 553 are mutually engaged and permanently interlocked.

The preselector 570 comprises an annular ring or a sleeve with a preselector stop feature 571. As illustrated in FIG. 40 the preselector stop feature 571 comprises numerous axial recesses in a proximal side of the preselector 570. The recesses may form slots of different axial length or of different elongation. A distal end or distal edge of the sleeve of the preselector may form a first preselector stop feature 471. The recess 501 may form a second preselector stop feature 572 and the further recess 502 may form a third preselector stop feature 573. The recesses 501, 502 comprise different elongations in longitudinal direction as illustrated in FIG. 40. Both recesses 501, 502 are open towards the distal end and hence towards the tracking stop feature 551. The recesses 501, 502 are located tangentially or circumferentially adjacent and next to each other.

Depending on the rotational position of the preselector 570 either the first recess 501 or the second recess 502 longitudinally aligns with the tracking stop feature 551. Since the dose tracker 550 and hence the tracking stop feature 551 thereof can only slide in longitudinal or axial direction relative to the housing and since the preselector 570 is axially or longitudinally fixed to the outer housing 200 the distance between the tracking stop feature 551 and a proximal end of the recesses 501, 502 defines a maximum displacement path for the dose tracker 550 for setting of a dose. Depending on the rotational state, hence depending on the preselection positional state p1, p2 of the preselector 570 the maximum displacement path for the dose tracker 550 can be modified on demand.

The recesses 501, 502 or slots are configured to receive and to engage the tracking stop feature 551 protruding radially outwardly from an outside surface of the tracking sleeve 555. In the present example the tracking stop feature 551 comprises a radially outwardly extending protrusion 556 integrally formed with the distal part 552 and protruding radially outwardly through a correspondingly shaped recess at a sidewall of the proximal part 553. It may likewise be integrally formed with the proximal part 553.

The radial extension of the protrusion 556 matches with the radial extension or radial position of the preselector stop feature 571. The preselector 570 is rotatable between at least two preselection positional states as described above. In any of the preselection positional states the preselector 570 is rotationally locked to the outer housing 200. The preselector 570 is also permanently longitudinally locked to the housing 10. For instance, a proximal end 572 or edge of the preselector 570 may be in axial abutment with the outer housing 200 or with another component of the injection device, e.g. with the release member 590 that is axially fixed to the outer housing 200. In this way the preselector 570 is locked to the outer housing 200 with regard to the longitudinal or axial direction.

The injection device 1 is further provided with an interlock 584. The interlock comprises a locking feature 575 extending through a recess or a through opening of the preselector 570. The locking feature 575 may comprise a spring biased actuator that is depressible in radial direction for temporarily releasing the preselector from the outer housing 200. The locking feature 575 may comprise a screw or the like fastening element that requires a correspondingly shaped tool for temporarily releasing the locking feature 575 and hence the preselector 570 from the outer housing 200 in order to enable a sliding motion or rotation of the preselector 570 relative to the outer housing 200. Depending on the selected preselection positional state of the preselector 578 a maximum dose positional state dm for the dose tracker 550 can be defined.

If the preselector 570 is in a first preselection positional state p1, in which the first recess 501 longitudinally aligns with the tracking stop feature 551 the maximum distance the dose tracker 550 is longitudinally displaceable relative to the outer housing 200 is shorter compared to a configuration in which the preselector 570 is in the second preselection positional state p2, in which the second recess 502 is longitudinally aligned with the tracking stop feature 551.

As further illustrated in FIG. 40 there are provided numerous preselection indications 576 on an outside surface portion of the preselector 570. One preselection indication 576 always aligns with a preselection window 213 provided in the outer housing 200. As illustrated in FIGS. 37 and 46 number 20 shows up in the preselection window 213 indicating to the user that a preselection of 20 units of the medicament has been pre-selected. Dialing or displacing the preselector 570 e.g. with the second recess 502 in alignment with the tracking stop feature 551 may reveal a larger number, e.g. number 30 in the preselection window 213.

Figure 41:
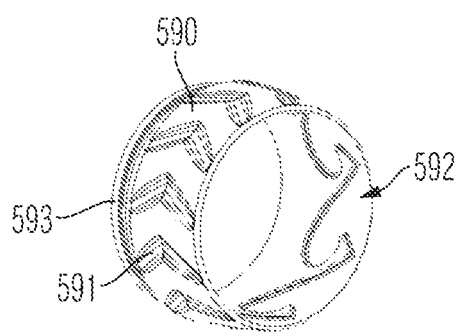
FIG. 41 is an isolated illustration of a release member.
Figure 42:
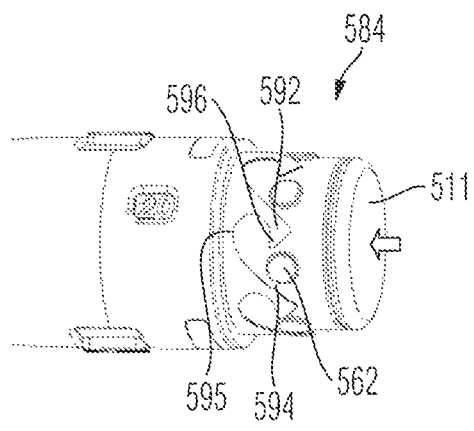
FIG. 42 shows an interaction between the dose tracker and the release member before reaching the end of a dispensing procedure.
Figure 43:
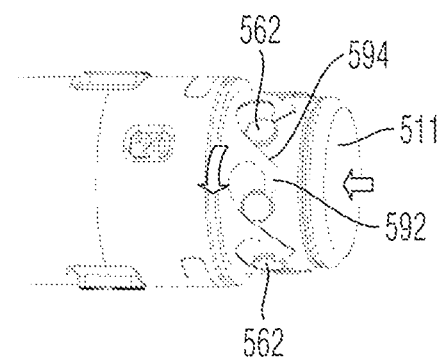
FIG. 43 is an illustration in accordance to FIG. 42 with the dose tracker moved even closer to the zero dose positional state.

The interaction between the release member 590 and the dose tracker 550 is illustrated in connection with FIG. 41 to FIG. 45. The release member 590 comprises an annular ring 591 comprising numerous catch elements 592 at an inside facing portion thereof as illustrated in FIG. 41. The release member 590 comprises an annular groove 593 near a proximal end of the annular ring 591. The groove 593 is positively engaged with a radially inwardly extending fastener 214 at the outer housing 200 as illustrated in FIG. 47. The fastener 214 comprises a radially inwardly extending protrusion positively engaged with the groove 593. In this way the release member 590 is freely rotatable relative to the outer housing 200 but is permanently locked to the outer housing 200 in longitudinal direction.

In the sequence of FIGS. 42 to 45 only the catch elements 592 and the proximal portion of the annular ring 591 are illustrated. An outer section of the annular ring 591 is cut away or faded away for illustration purpose in order to reveal the mutual engagement of the various catch elements 592 with radially outwardly extending protrusions 562 provided on an outside surface portion of the dose tracker 550. As illustrated, the protrusions 562 are of a pin-shaped structure. They extend radially outwardly near a proximal end of the proximal part 553. The catch elements 592 and the protrusions 562 are regularly and equidistantly arranged along the outer circumference of the dose tracker 550 and along the inner circumference of the annular ring 591, respectively.

The catch elements 592 extend at a predefined angle relative to the longitudinal direction. Each catch element 592 comprises a rather straight shaped beveled section 594 extending in distal direction into a curved section 595. The curved section 595 further extends into an undercut section 596. The curved section 595 extends from the beveled section 594 into the undercut section 596. The curved section 595 may even overlap with the undercut section 596. A free end of the undercut section 596 is located at a predefined tangential or circumferential distance from the beveled section 594. As the protrusion 562 is displaced in distal direction relative to the release member 590 it get gets in contact with the beveled section 594 and slides along the beveled section 594 until it reaches the curved section 595 as illustrated by a comparison of FIG. 43 and FIG. 44.

The curved section 595 is shaped and describes at least half of a circle or three-quarter of a circle. It describes a circumference of a circle of about 270°. A bottom of the curved section 595 forms the distal end of the catching element 592. Due to the curved section 595 the button thereof is in longitudinal overlapping configuration with the undercut section 596. As the protrusion 562 is displaced in distal direction and returned towards the zero dose positional state 50 the release member 590 is subject to a rotation in accordance to the extension and slope of the beveled section 594 and the curved section 595, respectively. As the protrusion 562 reaches the bottom of the curved section 595 it has tangentially entered a free space between the undercut section 596 and the curved section 595.

Figure 44:
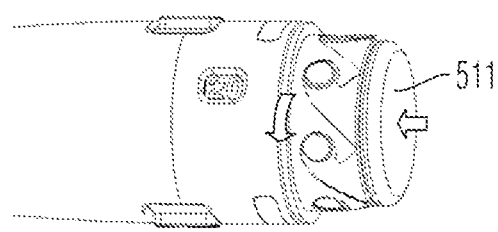
FIG. 44 shows the interaction of the release member and the dose tracker when reaching the zero dose positional state and FIG. 45 shows the mutual interaction of the release member and the dose tracker 40 and the dose tracker in the zero dose positional state.

Releasing of the trigger 511 in the configuration as shown in FIG. 44 may enable a small spring-driven proximally directed displacement of the dose tracker 550. But then the protrusion 562 gets in abutment with the undercut section 596, thereby impeding any further displacement of the dose tracker 550 relative to the release member 590 and hence relative to the outer housing 200 in proximal direction 3.

For release of the dose tracker 550 the release member 590 has to be rotated in a clockwise direction. In this way, the undercut section 596 induces a slight but distinct initial distal displacement of the dose tracker 550 before the protrusion 562 enters a free space between the undercut section 596 and the beveled section 594 of the catch element 592. Due to the regular arrangement of a plurality of catch elements 592 and protrusions 562 the protrusions 562 and catch elements 592 mutually engage and disengage simultaneously. Once the protrusions 562 to have disengaged from the catch elements 592 the dose tracker 550 is free to slide in proximal direction relative to the outer housing 200.

Figure 45:
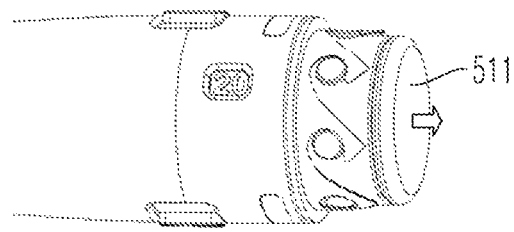

The annular ring 591 and hence the release member 590 may be also spring biased, e.g. by a further torsion spring not further illustrated here. In this way, the release member 590 could be kept in an interlocked configuration as shown in FIG. 45. A releasing motion of the release member 519 may that have to be conducted against the action of such a return spring.

Figure 39:
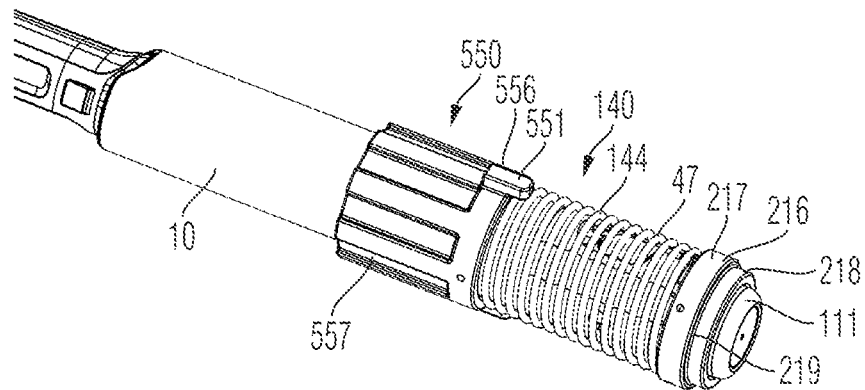
FIG. 39 shows the device according to FIGS. 37 and 38 without the outer housing.

As illustrated in FIG. 39 in connection with FIG. 46 or FIG. 47 there is also provided a spring 144 implemented as a torsion spring 147. The spring 144 has a first end 45 permanently connected to the dose tracker 550, in particular to its distal part 552. Since the dose tracker 550 is rotationally fixed to the outer housing 200 the first end 45 of the spring 144 is effectively connected to the outer housing 200 and hence to the housing 10. In other words the first end 145 of the spring 144 is indirectly connected or coupled to the housing 10.

The opposite second end 146 of the spring 144 is connected to the dose dial 112 or to a separate sleeve-shaped fastener 216 as for instance illustrated in FIG. 39. The fastener 216 is annular shaped and comprises a ring structure. The fastener 216 is permanently locked or attached to the dose dial 112 provided at the proximal end of the injection device 1. The fastener 216 may be adhesively attached to the dose dial 112. The second end 146 of the spring 144 is connected to the fastener 216 in a torque proof way. Liberating the dose setting mechanism, e.g. by actuating the release member 590 enables a rotation of the number sleeve 180 and a respective rotation of the dose dial 112. As illustrated further the fastener 216 comprises a rim 217 and a recessed portion 218 on the outside surface of the fastener 216. The rim 217 extends into the recessed portion 118 via a radial step 119 or shoulder.

As illustrated in FIG. 28 the dose tracker 550, in particular the proximal part 553 comprises a radially inwardly extending ledge or rim 558 that is in axial abutment with the step 219. Insofar the rim 217 is in axial abutment with the rim 558. As the spring 144 induces a dose incrementing rotation of the fastener 216 and hence of the dose dial 112 the number sleeve 180 starts to rotate relative to the housing 10. Due to the threaded engagement between the insert 162 and the number sleeve 180 the number sleeve 180 and hence the dose dial 112 as well as the fastener 216 become subject to a proximally directed displacement relative to the outer housing 200. This proximal displacement of the fastener 216 is equally transferred to the dose tracker 550 due to the mutual axial abutment and engagement between the rim 217 and the rim 558.

A spring driven rotation of the number sleeve 180 therefore transfers to a longitudinal sliding and proximal displacement of the dose tracker 550 until the tracking stop feature 551 thereof engages with the preselector stop feature 571. As illustrated in FIGS. 46 and 47 there is provided a separate trigger 511 that covers the trigger 111 of the injection device 1. The trigger 511 is provided and configured to cover the trigger 111. The trigger 511 comprises a larger cross-section compared to the cross-section of the trigger 111. The trigger 511 may be adhesively attached to the trigger 111. The trigger 511 is configured to cover a proximal end of the outer housing 200.

Figure 48:
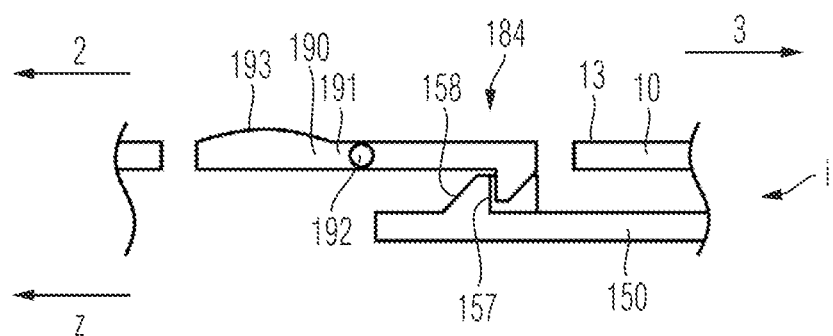
FIG. 48 is exemplary of the interaction between an interlock and a release member in an initial configuration.
Figure 49:
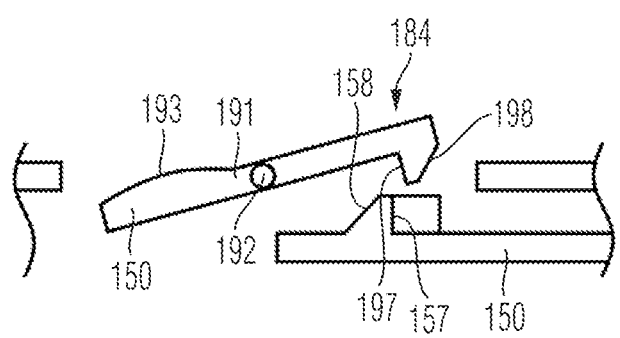
FIG. 49 shows the arrangement of FIG. 48 with the interlock released.

In FIGS. 48 and 49 a more detailed exemplary implementation of an interlock 184 and a release member 190 is illustrated. Here, the interlock 184 comprises a first locking feature provided on the dose tracker 150 and further comprises a second locking feature provided on the release member 190. The first locking feature is presently implemented as a catch 157 protruding radially outwardly from the dose tracker 150. The catch 157 may be integrally formed with the dose tracker 150. The release member 190 comprises a correspondingly shaped catch 197 protruding radially inwardly from the release member 190. The catch 197 may be also integrally formed with the release member 190.

The release member 190 is configured as a pivotable lever 191. The lever 191 is pivotally supported on a pivot axis 192. The pivot axis extends in tangential or circumferential direction with regard to the overall geometry of the housing 10. The lever 191 may flush with the outside surface of the sidewall 13 of the housing 10 in the initial configuration i as shown in FIG. 48.

The lever 191 comprises the catch 197 and a depressible end portion at an opposite end. The depressible end portion and the catch 197 are provided on opposite ends of the lever 191. By depressing the depressible end radially inwardly the opposite end and hence the catch 197 is raised or lifted radially outwardly thus disengaging from the catch 157 of the dose tracker 150 as illustrated in FIG. 49. The release member 190 may be further provided with a return spring, presently not illustrated. The return spring may be arranged at the pivot axis 192 in order to return the release member 190 into the initial configuration as shown in FIG. 48, in which the catch 197 of the release member 190 is in axial abutment and in engagement with the correspondingly shaped catch 157 of the dose tracker 150.

The catch 157 comprises an axial abutment face facing in proximal direction. The catch 197 comprises a correspondingly shaped axial abutment surface facing in distal direction. In the initial configuration as illustrated in FIG. 48 the two abutment faces are in axial abutment thus inhibiting a proximally directed displacement of the dose tracker 150.

In one embodiment the release member 190 may comprise a radially outwardly bulged portion 193 that is configured to become depressed by the user of the device. The radially raised or bulged portion 193 slightly protrudes from the outside surface of the sidewall 13 of the housing 10. Insofar it provides a haptic feedback to the user that this respective bulged portion 193 is configured for a radially inwardly directed depression. Once the user depresses the bulged portion 193 the oppositely located end section of the lever 191 is raised so that the mutually corresponding abutment faces 157, 197 get out of engagement. As the dose tracker 150 and hence the interlock 184 is liberated, the dose tracker 150 is free to rotate or to move proximally in longitudinal direction under the effect of the spring 140 as described above, e.g. in connection with FIGS. 25 to 28.

The catch 157 further comprises a beveled section 158. The catch 197 also comprises a correspondingly shaped beveled section 198. The beveled section 158 of the dose tracker 150 faces in distal direction 2 whereas the beveled section 198 of the release member 190 faces in proximal direction 3. During dose delivery and hence at the end of a dose dispensing procedure the dose tracker 150 is subject to a distally directed displacement, hence to the left in FIGS. 48 and 49. As the catch 157 approaches the initial configuration or initial axial position as indicated in FIG. 48, the beveled section 158 slides along the beveled section 198. Such a sliding motion is accompanied by the release member 198 becoming lifted radially outwardly so that the outermost and inner most radial tips of the catches 157, 197 mutually pass by until the axial abutment faces 157, 197 return into an engagement configuration as shown in FIG. 48.

If the release member 190 or its lever 191 biased by a spring, the catch 197 is raised or lifted radially outwardly against the action of the respective spring. As soon as the abutment faces 197, 157 get in alignment the lever 191 snaps into the initial configuration as illustrated in FIG. 48 under the action of the spring.

Figure 50:
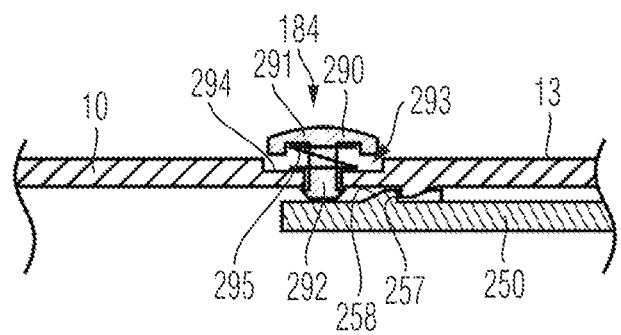
FIG. 50 shows another example of an interaction between an interlock and a release member in an initial or interlocked configuration and FIG. 51 shows the arrangement of FIG. 50 with the interlock released.
Figure 51:
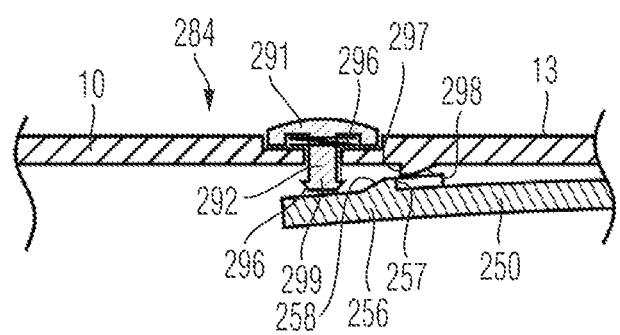

In FIGS. 50 and 51 a further conceivable implementation of an interlock 284 and a release member 290 is illustrated. Here, the dose tracker 250 comprises an elastic portion 256. The elastic portion 256 may axially protrude from the dose tracker 250. Alternatively, it may be integrated into the sidewall of the dose tracker 250. It may be separated from a sidewall of the dose tracker along a u-shaped slit. Here, the dose tracker 250 comprises a catch 257 correspondingly shaped with a catch 297 provided at an inside facing portion of the sidewall 13 of the housing 10. The catch 257 comprises an axial abutment face as described above that faces in proximal direction 3. The correspondingly shaped catch 297 of the housing 10 comprises a distally facing abutment face to engage with or to abut with the abutment face 257.

The catch 257 and the well as the catch 297 both comprise a beveled section 258, 298 that enable and induce a slight radially inwardly directed elastic deformation of the elastic portion 256 as the dose tracker 250 returns into the initial configuration as illustrated in FIG. 50.

The interlock 284 is formed by the mutually corresponding catches 257, 297 of the dose tracker 250 and the housing 10. In order to release the interlock 284 there is provided a release member 290 in form of a depressible button 291. The release member 290 comprises a somewhat planar-shaped or slightly bulged button 291 integrally formed with a longitudinally extending stem 292. The stem 292 extends radially inwardly and intersect a recess or through opening in the sidewall 13 of the housing 10. The button 291 slightly protrudes from the outside surface of the sidewall 13 of the housing 10. It is radially displaceably supported on the housing 10 against the action of a spring 295. The spring 295 is located in a recess 293 on the outside surface of the sidewall 13. The recess 293 comprises a bottom 294 that is recessed compared to the outside surface of the sidewall 13. The bottom 294 provides a support for the spring 295. An opposite end of the spring 295 is in abutment with an underside of the button 291.

An inner free end 299 of the stem 292 protrudes radially inwardly from an inside surface of the sidewall 13. The free end 299 is provided with lateral protrusions 296 that are separated by distance that is larger than the inner diameter of the recess of the sidewall 13 through which the stem 292 extends. In this way, the stem 292 and the entire button 291 is hindered from getting pushed out of the housing 10 under the action of the spring 295.

In an initial configuration as illustrated in FIG. 50 the free end 299 of the stem 292 axially overlaps with the elastic portion 256 of the dose tracker 250. By depressing the release member 290 and hence the button 291 radially inwardly, the stem 292 advances downward in the illustration of FIG. 50 and FIG. 51. Since the free end 299 is in abutment with an outside surface portion of the elastic portion 256 such a depression leads to a local and radially inwardly directed deformation of the elastic portion 256. The elastic deformation is large enough to bring the catches 297, 298 out of engagement so as to liberate a proximally directed displacement of the dose tracker 250.

The examples of FIGS. 48 to 51 are only exemplary for an interlock 184, 284 and a release member 190, 290 and can be generally implemented with any of the examples as illustrated in FIG. 1 to FIG. 47.

| List of reference numbers | | | |
|---|---|---|---|
| 1 | injection device | 36a | tooth |
| 2 | distal direction | 38 | protrusion |
| 3 | proximal direction | 40 | spring |
| 4 | first direction | 43 | inner thread |
| 5 | second direction | 44 | threaded insert |
| 6 | cartridge | 45 | sleeve section |
| 7 | piston | 46 | proximal face |
| 8 | drive mechanism | 47 | socket section |
| 9 | dose setting mechanism | 48 | shoulder portion |
| 10 | housing | 50 | clutch |
| 11 | preselection window | 51 | sleeve section |
| 12 | dose indicating window | 52 | thread |
| 13 | sidewall | 53 | ratchet member |
| 14 | cartridge holder | 54 | ratchet member |
| 15– | needle assembly | 55 | engaging section |
| 16 | inner needle cap | 56 | engaging section |
| 17 | outer needle cap | 57 | distal face |
| 18 | protective cap | 58 | proximal face |
| 19 | recess | 60 | dose tracker |
| 20 | piston rod | 61 | dose button |
| 21 | groove | 61a | support face |
| 22 | pressure foot | 62 | threaded section |
| 23 | thread | 63 | tracking stop feature |
| 25 | barrel | 63a | stop face |
| 26 | seal | 64 | leg |
| 28 | socket | 65 | leg |
| 30 | driver | 66 | dose size indicator |
| 31 | sleeve section | 67 | distal face |
| 32 | flange | 68 | interlock member |
| 33 | bore | 68a | arm |
| 34 | toothed section | 68b | engaging structure |
| 34a | tooth | 69 | interlock member |
| 35 | axial face | 69a | arm |
| 36 | toothed section | 69b | engaging structure |
| 71 | sleeve section | 111 | trigger |
| 72 | recess | 112 | dose dial |

-continued

List of reference numbers

| | | | |
|---|---|---|---|
| 73 | stop feature | 113 | dosage window |
| 73a | stop face | 120 | piston rod |
| 74a | stop face | 121 | bearing |
| 75 | stop feature | 122 | first thread |
| 75a | stop face | 123 | pressure foot |
| 76 | protrusion | 124 | second thread |
| 77 | preselection indication | 130 | driver |
| 78 | through opening | 131 | threaded section |
| 80 | spring | 132 | flange |
| 81 | distal end | 133 | flange |
| 82 | proximal end | 135 | last dose limiting member |
| 83 | compression spring | 140 | spring |
| 84 | interlock | 141 | distal end |
| 86 | retainer | 142 | proximal end |
| 90 | support | 143 | preselection indication |
| 91 | body | 144 | spring |
| 92 | strut section | 145 | first end |
| 93 | strut section | 146 | second end |
| 94 | distal face | 147 | torsion spring |
| 95 | flange section | 150 | dose tracker |
| 96 | toothed section | 151 | tracking stop feature |
| 97 | flange section | 152 | tracking stop feature |
| 98 | recess | 153 | tracking stop feature |
| 99 | recess | 154 | proximal end |
| 100 | release member | 153 | proximal end |
| 101 | release member | 155 | tracking sleeve |
| 102 | release button | 156 | protrusion |
| 103 | release button | 157 | catch |
| 104 | flange section | 158 | catch |
| 106 | resilient arm | 160 | clutch |
| 107 | resilient arm | 162 | insert |
| 108 | connecting piece | 163 | protrusion |
| 109 | engaging structure | 164 | stem |
| 165 | spring | 257 | catch |
| 166 | clutch | 258 | catch |
| 167 | recess | 270 | preselector |
| 168 | sidewall | 271 | preselector stop feature |
| 170 | preselector | 276 | protrusion |
| 171 | preselector stop feature | 290 | release member |
| 172 | preselector stop feature | 292 | stem |
| 173 | preselector stop feature | 293 | recess |
| 175 | preselection indication | 294 | bottom |
| 180 | number sleeve | 295 | spring |
| 18 | groove | 296 | protrusion |
| 184 | interlock | 297 | catch |
| 190 | release member | 298 | catch |
| 191 | lever | 299 | free end |
| 192 | pivot axis | 350 | dose tracker |
| 193 | bulged portion | 351 | tracking stop feature |
| 197 | catch | 355 | tracking sleeve |
| 198 | catch | 356 | protrusion |
| 200 | outer housing | 370 | preselector |
| 201 | groove | 371 | preselector stop feature |
| 202 | groove | 372 | preselector stop feature |
| 203 | groove | 373 | preselector stop feature |
| 204 | connecting groove | 376 | protrusion |
| 207 | groove | 450 | dose tracker |
| 213 | preselection window | 451 | tracking stop feature |
| 214 | fastener | 452 | tracking stop feature |
| 216 | fastener | 453 | tracking stop feature |
| 217 | rim | 455 | tracking sleeve |
| 218 | recessed portion | 470 | preselector |
| 219 | step | 471 | preselector stop feature |
| 250 | dose tracker | 476 | protrusion |
| 251 | tracking stop feature | 501 | recess |
| 252 | tracking stop feature | 502 | recess |
| 253 | tracking stop feature | 511 | trigger |
| 255 | tracking sleeve | 550 | dose tracking member |
| 256 | elastic portion | 551 | tracking stop feature |
| 552 | distal part | | |
| 553 | proximal part | | |
| 555 | tracking sleeve | | |
| 556 | protrusion | | |
| 557 | rib | | |
| 558 | rim | | |
| 562 | protrusion | | |
| 570 | preselector | | |

-continued

List of reference numbers

| | | |
|---|---|---|
| 571 | preselector stop feature | |
| 572 | preselector stop feature | |
| 573 | preselector stop feature | |
| 572 | proximal end | |
| 575 | locking feature | |
| 576 | preselection indication | |
| 584 | interlock | |
| 590 | release member | |
| 591 | annular ring | |
| 592 | catch element | |
| 593 | groove | |
| 594 | beveled section | |
| 595 | curved section | |
| 596 | undercut section | |
| p1 | preselection positional state | |
| p2 | preselection positional state | |
| d0 | zero dose positional state | |
| dm | maximum dose positional state | |
| i | initial position | |
| a | activation position | |

The invention claimed is:

1. An injection device for setting and injecting a dose of a medicament, the injection device comprising:
an elongated housing extending along a longitudinal axis;
a piston rod to operably engage with a piston of a cartridge filled with the medicament;
a dose tracker selectively operably engageable with the piston rod, wherein the dose tracker is longitudinally displaceable relative to the housing from an initial position in a proximal direction towards a first activation position during setting of the dose and wherein the dose tracker is longitudinally displaceable relative to the housing in a distal direction from the first activation position towards the initial position during dispensing of the dose;
a spring to urge the dose tracker in the proximal direction relative to the housing;
an interlock to lock the dose tracker in the initial position relative to the housing;
a release member to release the interlock;
at least one first tracking stop feature provided on one of the dose tracker and the housing, wherein the at least one first tracking stop feature is configured to block a longitudinal displacement of the dose tracker relative to the housing when the dose tracker reaches the first activation position; and
a preselector separate from the release member and comprising at least one first preselector stop feature to engage with the at least one first tracking stop feature, wherein the preselector is at least one of translationally and rotationally displaceable relative to the housing between at least two preselection positional states.

2. The injection device according to claim 1, wherein the preselector is lockable to at least one of the housing and the dose tracker in any of the at least two preselection positional states.

3. The injection device according to claim 1, wherein the preselector is rotationally supported on or in at least one of the housing and the dose tracker,
a) wherein the preselector comprises at least one second preselector stop feature being at least one of tangentially and longitudinally offset from the at least one first preselector stop feature, or b) wherein at least one of the dose tracker and the housing comprises at least one second tracking stop feature being at least one of tangentially and longitudinally offset from the at least one first tracking stop feature.

4. The injection device according to claim 3, wherein the at least one first preselector stop feature comprises a first stop face configured to abut with a second stop face of the at least one first tracking stop feature.

5. The injection device according to claim 4, wherein the at least one second preselector stop feature comprises a third stop face longitudinally offset from the first stop face of the at least one first preselector stop feature.

6. The injection device according to claim 1, wherein one of the at least one first tracking stop feature and the at least one first preselector stop feature comprises a first radial protrusion and wherein the other one of the at least one first tracking stop feature and the at least one first preselector stop feature comprises at least one of
a) a second radial protrusion configured to abut with the first radial protrusion; and
b) a groove configured to slidably receive the first radial protrusion.

7. The injection device according to claim 1, further comprising a trigger integrally formed or longitudinally engaged with the dose tracker, wherein at least one of the trigger and a proximal end of the dose tracker protrudes from a proximal end of the housing when the dose tracker is in the first activation position.

8. The injection device according to claim 7, wherein a longitudinal distance between the initial position and the first activation position of the dose tracker correlates with the size of the dose.

9. The injection device according to claim 1, wherein the spring has a first end operably connected to the housing and has a second end operably connected to the dose tracker, wherein the spring comprises a cylindrically shaped compression spring or a helically wound torsion spring, and wherein the spring encloses at least a portion of the dose tracker or wherein the spring is arranged inside a hollow portion of the dose tracker.

10. The injection device according to claim 1, wherein the release member comprises an annular ring rotationally supported at a proximal end of the housing, wherein one of an inside surface of the annular ring and an outside surface of the dose tracker comprises at least one catch element to engage with a protrusion on the other one of the inside surface of the annular ring and the outside surface of the dose tracker.

11. The injection device according to claim 1, wherein the release member comprises a release button located in a recess of a sidewall of the housing and depressible into the housing for releasing the dose tracker.

12. The injection device according to claim 1, wherein the interlock comprises a first engaging structure connected to or integral with the dose tracker and a second engaging structure connected to or integral with the release member and wherein the first engaging structure and the second engaging structure are positively engaged with regard to the longitudinal direction when the at least one release member is in an initial position and when the dose tracker is in the initial position, wherein the first and the second engaging structures are disengaged when the at least first one release member is depressed.

13. The injection device according to claim 1, further comprising the cartridge comprising a barrel filled with the medicament and sealed by the piston that is axially displaceable relative to the barrel by the piston rod.

14. The injection device according to claim 1, wherein preselected doses of different sizes of the medicament can be defined by moving the preselector relative to the housing.

15. The injection device according to claim 1, wherein the preselector is fixed or locked to the housing during setting of the dose and during dispensing of the dose of the medicament.

* * * * *